(12) United States Patent
Waisman

(10) Patent No.: US 8,304,400 B2
(45) Date of Patent: Nov. 6, 2012

(54) COMPOSITIONS AND METHODS FOR INHIBITING TUMOR GROWTH AND METASTASIS

(76) Inventor: David M. Waisman, Calgary (CA)

( * ) Notice: Subject to any disclaimer, the term of this patent is extended or adjusted under 35 U.S.C. 154(b) by 0 days.

(21) Appl. No.: 12/775,670

(22) Filed: May 7, 2010

(65) Prior Publication Data

US 2011/0172287 A1    Jul. 14, 2011

Related U.S. Application Data

(60) Division of application No. 11/621,629, filed on Jan. 10, 2007, now abandoned, which is a division of application No. 10/735,577, filed on Dec. 12, 2003, now abandoned, which is a continuation-in-part of application No. 10/304,287, filed on Nov. 26, 2002, now Pat. No. 7,250,271.

(60) Provisional application No. 60/433,140, filed on Dec. 13, 2002, provisional application No. 60/333,866, filed on Nov. 28, 2001.

(51) Int. Cl.
*A61K 31/70* (2006.01)
*C07H 21/02* (2006.01)
*C07H 21/04* (2006.01)

(52) U.S. Cl. ............... 514/44 A; 536/24.1; 536/24.5

(58) Field of Classification Search ............... 514/44; 536/24.5
See application file for complete search history.

(56) References Cited

U.S. PATENT DOCUMENTS

| | | | |
|---|---|---|---|
| 4,462,980 A | 7/1984 | Diedrichsen et al. |
| 5,639,725 A | 6/1997 | O'Reilly et al. |
| 5,801,012 A | 9/1998 | Soff et al. |
| 5,837,682 A | 11/1998 | Folkman et al. |
| 5,945,403 A | 8/1999 | Folkman et al. |
| 5,972,896 A | 10/1999 | Davidson |
| 6,024,688 A | 2/2000 | Folkman et al. |
| 6,794,363 B2 | 9/2004 | Bejanin |
| 6,841,539 B1 | 1/2005 | Mehta et al. |
| 7,250,271 B2 | 7/2007 | Waisman et al. |
| 7,420,036 B2 | 9/2008 | Waisman et al. |
| 7,626,008 B2 | 12/2009 | Waisman et al. |
| 2004/0142897 A1 | 7/2004 | Waisman |
| 2007/0231899 A1 | 10/2007 | Waisman |

FOREIGN PATENT DOCUMENTS

| | | |
|---|---|---|
| CA | 2426543 A1 | 9/2007 |
| CA | 2514873 A1 | 1/2012 |
| EP | 1337548 B1 | 7/2008 |
| WO | 90/13640 A1 | 11/1990 |
| WO | 99/00420 A1 | 1/1999 |
| WO | 99/16889 | 4/1999 |

(Continued)

OTHER PUBLICATIONS

Hammond et al. (Nature Reviews Genetics 2001, vol. 2:110-119).*

(Continued)

*Primary Examiner* — Terra Cotta Gibbs

(57) ABSTRACT

Disclosed are compositions and methods useful in the reduction of p11 protein activity in cancer cells. P11 protein is demonstrated to affect plasmin production and activity, MMP activity, plasminogen activation, antiangiogenic plasmin fragment production, cell invasion, tumor development and metastasis. Compositions that modulate levels of p11 either up or down are demonstrated to be effective in reducing tumor development. Also disclosed are cancer treatment methods that employ compositions that modulate p11 activity and clonal cell lines and assays useful for the identification of compositions that modulate p11 activity.

14 Claims, 37 Drawing Sheets

FOREIGN PATENT DOCUMENTS

| WO | 02/17857 A2 | 3/2002 |
|---|---|---|
| WO | 02/44328 | 6/2002 |
| WO | WO0244328 | 6/2002 |
| WO | WO03045323 A2 | 6/2003 |
| WO | WO2004054517 A2 | 7/2004 |

OTHER PUBLICATIONS

Ballagamba et al,. "Tyrosine phosphorylatin of annexin II tetramer is stimulated by membrane binding", Journal of Biological Chemistry, 1997, pp. 3195-3199, vol. 272, No. 6.

Brooks et al., "Ca2+-dependent and phospholipid-independent binding of annexin 2 and annexin 5", Journal of Biochemistry, 2002, pp. 895-900, vol. 367, Pt 3.

Cao et al., "Kringle domains of human angiostain. Characterization of the anti-proliferative activity on endothelial cells". Journal of Biological Chemistry, 1996. pp. 29461-29467, vol. 271, No. 46.

Caplan et al., "Regulation of Annexin A2 by Reversible Glutathionylation", Journal of Biological Chemistry, 2004, pp. 7740-7750, vol. 279, No. 9.

Choi et al., "p11 regulates extracellular plasmin production and invasiveness of HT1080 fibrosarcoma cells", FASEB Journal, 2003, pp. 235-246, vol. 17, No. 2.

Choi et al., "Regulation of Plasmin-Dependent Fibrin Clot Lysis by Annexin II Heterotetramer", Journal of Biological Chemistry, 2001, pp. 25212-25221, vol. 276, No. 27.

Choi et al., "Annexin II Tetramer Inhibits Plasmin-Dependent Fibrinolysis", Biochemistry, 1998, pp. 648-655, vol. 37.

Falcone et al., "Macrophage formation of angiostatin during inflammation. A byproduct of the activation of plasminogen", Journal of Biological Chemistry, 1998, pp. 31480-31485, vol. 273, No. 47.

Filipenko et al., "Annexin A2 is a Novel RNA Binding Protein", Journal of Biological Chemistry, 2004, pp. 8723-8731, vol. 279, No. 10.

Filipenko et al., "The C Terminus of Annexin II Mediates Binding to F-Actin", Journal of Biological Chemistry, 2001, pp. 5310-5315, vol. 276, No. 7.

Filipenko et al., "Characterization of Ca2+-binding Sites of Annexin II Tetramer", Journal of Biological Chemistry, 2000, pp. 38877-38884, vol. 275, No. 49.

Fitzpatrick et al., "Fucoidan Dependent Conformatinal Changes in Annexin II Tetramer", Biochemistry, 2000, pp. 2140-2148, vol. 39.

Fitzpatrick et al., "Regulation of Plasmin Activity by Annexin II Tetramer", Biochemistry, 2000, pp. 1021-1028, vol. 39.

Fogg et al., "The p11 Subunit Annexin II Heterotetramer is Regulated by Basic Carboxypeptidase", Biochemistry, 2002, pp. 4953-4961, vol. 41.

Gately et al., "The mechanism of cancer-mediated conversion of plasminogen to the angiogenesis inhibitor angiostatin", Proceedings of the National Academy of Sciences, 1997, pp. 10868-10872, vol. 94, No. 20.

Johnsson et al., "Alkylation of cysteine 82 of p11 abolishes the complex formation with the tyrosine-protein kinase substrate p36 (annexin 2, calpactin 1, lipocortin 2)", Journal of Biological Chemistry, 1990, pp. 14464-14468, vol. 265, No. 24.

Kang, et al., "Characterization of Human Recombinant Annexin II Tetramer Purified from Bacteria: Role of N-Terminal Acetylation", Biochemistry, 1997, pp. 2041-2050, vol. 37.

Kassam et al., "Characterization of the heparin binding properties of annexin II tetramer", Journal of Biological Chemistry, 1997, pp. 15093-15100, vol. 272, No. 24.

Kassam et al., "The p11 Subunit of the Annexin II Tetramer Plays a Key role in the Stimulation of t-Pa-Dependent Plasminogen Activation", Biochemistry, 1998, pp. 16958-16966, vol. 37.

Kassam et al., "The Role of Annexin II Tetramer in the Activation of Plasminogen", Journal of Biological Chemistry, 1998, pp. 4790-4799, vol. 273, No. 8.

Kassam et al., "Purification and Characterization of A61", Journal of Biological Chemistry, 2001, pp. 8924-8933, vol. 276, No. 23.

Kwon et al., "p22 is a novel plasminogen fragment with antiangiogenic activity", Biochemistry, 2001, pp. 13246-13253, vol. 40, No. 44.

Kwon et al., "Identification of Annexin II Heterotetramer as a Plasmin Reductase", Journal of Biological Chemistry, 2002, pp. 10903-10911, vol. 277, No. 13.

Lay et al., "Phosphoglycerate Kinase Acts in Tumour Angiogenesis as a Disulphide Reductase", Nature, 2000, pp. 869-873, vol. 408.

MacLeod et al., "Phospholipid associated Annexin AS-S100A10 Heterotetramer and Its Subunits", Journal of Biological Chemistry, 2003, pp. 25577-25584, vol. 278, No. 28.

Soff, "Angiostatin and angiostatin-related proteins", Cancer and Metastasis Review, 2000, pp. 97-107, vol. 19, Nos. 1-2.

Stathakis et al., "Generation of Angiostatin by Reduction and Proteolysis of Plasmin", Journal of Biological Chemistry, 1997, pp. 20641-20645, vol. 272, No. 33.

Stathakis et al., "Angiostatin formation involves disulfide bond reduction and proteolysis in kringle 5 of plasmin", Journal of Biological Chemistry, 1999, pp. 8910-8916, vol. 274, No. 13.

Teratani et al., "Induced transcriptional expression of calcium-binding protein S100A1 and S100A10 genes in human renal cell carcinoma", Cancer Letters, 2002, pp. 71-77, vol. 175, No. 1.

Wu et al., "P11, a unique member of the S100 family of calcium-binding proteins, interacts with and inhibtts the activity of the 85-kDa cytosolic phospholiase A2", Journal of Biological Chemistry, 1997, pp. 17145-17153, vol. 272, No. 27.

Wu et al., Accession NM_002966, 2006.

Zhang et al., "RNA Interference mediated Silencing of S100A10 Gene Attenuates Plasmin Generation & Invasiveness of Colo 222", Journal of Biological Chemistry, 2004, pp. 2053-2062, vol. 279, No. 3.

Heidtmann et al., "Generation of angiostatin-like fragments from plasminogen by prostate-specific antigen" 1999, British Journal of Cancer, pp. 1269-1273, vol. 81, No. 8.

MacDonald et al., "The tumor-suppressing activity of angiostatin protein resides within kringles 1 to 3", 1999, Biochemical and Biophysical Research Communications, pp. 469-477, vol. 264, No. 2.

Menhart et al., "Construction, expression, and purification of recombinant kringle 1 of human plasminogen and analysis of its interaction with omega-amino acids", 1991, Biochemistry, pp. 1948-1957, vol. 30, No. 7.

Yao et al., "Dexamethasone alters arachidonate release from human epithelial cells by induction of p11 protein synthesis and inhibition of phospholipase A2 activity", 1999, Journal of Biological Chemistry, pp. 17202-17208, vol. 274, No. 24.

International Search Report for PCT/US02/37879 dated Oct. 24, 2005; 4 pages.

International Search Report for PCT/US03/40029 dated Oct. 12, 2006; 6 pages.

Office Action dated Aug. 8, 2008 from related U.S. Appl. 11/621,629, 24 pgs.

Office Action dated Nov. 9, 2009 from related U.S. Appl. No. 11/621,629, 21 pgs.

Lu et al., "Delivering siRNA in vivo for functional genomics and novel therapeutics", 2005, RNA Interference Technology, pp. 303-317.

Downward, "Science, medicine, and the future RNA interference", 2004, BJM, pp. 1245-1258, vol. 328.

Braasch et al., "Novel Antisense and Peptide Nucleic Acid Strategies for Controlling Gene Expression", Apr. 2002, Biochemistry, pp. 4503-4510, vol. 41(14).

Supplementary European Search Report dated Nov. 24, 2004 from related European Patent Application No. 01987119.3; 6 pages.

Taurog, J. et al., "HLA-B27 in Inbred and Non-Inbred Transgenic Mice," J. Immunol., 1988, pp. 4020-4023, vol. 141, No. 11.

Wall, R.J., "Transgenic Livestock Progress and Prospects for the Future," Theriogenology, 1996, pp. 57-68, vol. 45.

Office Action dated May 21, 2004 from related Canadian Patent Application No. 2,426,543; 4 pages.

Cameron, E. "Recent Advances in Transgenic Technology," Molec. Biol., 1997, pp. 253-265, vol. 7.

Decision on Reexamination dated Apr. 20, 2006 from related Chinese Patent Application No. 01819642.X, 1 page.

Examiner Interview Summary Record dated Jun. 14, 2006 from related U.S. Appl. No. 10/304,287; 1 page.

Final Office Action dated Jan. 25, 2008 from related U.S. Appl. No. 10/415,012; 10 pages.

Final Office Action dated Oct. 20, 2006 from related U.S. Appl. No. 10/304,287; 7 pages.

Hammer, R. et al., "Spontaneous Inflammatory Disease in Transgenic Rats Expressing HLA-B27 and Human β2m: An Animal Model of HLA-B27-Associated Human Disorders," 1990, Cell, vol. 63, 1099-1112.

Houdebine, L-M., "Production of pharmaceutical proteins from transgenic animals," J. Biotech., 1994, pp. 269-287, vol. 34.

International Preliminary Examination Report dated Mar. 22, 2007 for related International Patent Application No. PCT/US01/044515, 18 pages.

International Search Report dated Nov. 29, 2002 for related International Patent Application No. PCT/US01/044515, 2 pages.

Mullins, J.J. et al., "Fulminant hypertension in transgenic rats harbouring the mouse Ren-2 gene," Nature, 1990, pp. 541-544, vol. 344.

Mullins, J. et al., "Transgenesis in Nonmurine Species," Hypertension, 1993, pp. 630-633, vol. 22.

Mullins, L. et al., "Perspectives Series: Molecular Medicine in Genetically Engineered Animals," J. Clin. Invest., 1996, pp. S37-S40, vol. 98.

Mullins, J.J. et al., "Expression of the DBA/2J Ren-2 gene in the adrenal gland of transgenic mice," EMBO J., 1989, pp. 4065-4072, vol. 8, No. 13.

Niemann, H., "Transgenic farm animals get off the ground," Transg. Res., 1997, pp. 73-75, vol. 7.

NCBI Accession No. NP_000292.1, Mar. 19, 1999, 5 pages.

NCBI Accession No. AAA36451, Apr. 27, 1993, 3 pages.

Notice of Allowance dated Feb. 6, 2009 from related Chinese Patent Application No. 01819642.X; 2 pages.

Notice of Allowance dated Apr. 19, 2007 from related U.S. Appl. No. 10/304,287; 5 pages.

Notice of Allowance dated Aug. 31, 2009 from related European Patent Application No. 03813462.3; 6 pages.

Notice of Allowance dated Jul. 27, 2009 from related U.S. Appl. No. 12/183,896; 4 pages.

Notice of Allowance dated May 2, 2008 from related U.S. Appl. No. 10/415,012; 4 pages.

Notice of Allowance dated Feb. 15, 2007 from related Canadian Patent Application No. 2,426,543; 1 page.

Notice of Allowance dated Nov. 8, 2007 from related European Patent Application No. 01987119.3; 3 pages.

Notice of Allowance dated Sep. 3, 2011 from related Canadian Patent Application No. 2,514,873; 1 page.

Office Action dated Aug. 24, 2005 from related U.S. Appl. No. 10/304,287; 14 pages.

Office Action dated Aug. 26, 2005 from related European Patent Application No. 01987119.3; 4 pages.

Office Action dated Aug. 4, 2009 from related Canadian Patent Application No. 2,514,873; 5 pages.

Office Action dated Oct. 5, 2005 from related New Zealand Patent Application No. 526065; 2 pages.

Office Action dated Feb. 12, 2009 from related European Patent Application No. 03813462.3; 4 pages.

Office Action dated Feb. 20, 2009 from related U.S. Appl. No. 12/183,896; 13 pages.

Office Action dated Jan. 27, 2011 from related Canadian Patent Application No. 2,514,873; 1 pages.

Decision on Rejection dated Nov. 18, 2005 from related Chinese Patent Application No. 01819642.X; 4 pages.

Office Action dated Jan. 7, 2005 from related Chinese Patent Application No. 01819642.X; 6 pages (with English translation, 6 pages).

Office Action dated Jul. 12, 2006 from related U.S. Appl. No. 10/735,577; 14 pages.

Office Action dated Jul. 9, 2008 from related European Patent Application No. 03813462.3; 4 pages.

Office Action dated Jun. 15, 2007 from related U.S. Appl. No. 10/415,012; 13 pages.

Office Action dated Mar. 1, 2005 from related Canadian Patent Application No. 2,426,543; 2 pages.

Office Action dated Mar. 22, 2006 from related U.S. Appl. No. 10/304,287; 7 pages.

Office Action dated Mar. 3, 2006 from related European Patent Application No. 01987119.3; 5 pages.

Office Action dated May 15, 2006 from related Canadian Patent Application No. 2,426,543; 2 pages.

Office Action dated Nov. 30, 2006 from related European Patent Application No. 01987119.3; 4 pages.

Office Action dated Oct. 3, 2005 from related U.S. Appl. No. 10/735,577; 14 pages.

Office Action dated Oct. 4, 2005 from related Canadian Patent Application No. 2,426,543; 2 pages.

Office Action dated Sep. 9, 2003 from related Canadian Patent Application No. 2,426,543; 4 pages.

Office Action dated Nov. 23, 2006 from related Canadian Patent Application No. 2,426,543; 1 page.

Office Action dated Sep. 12, 2008 from related Chinese Patent Application No. 01819642.X; 3 pages (with English translation, 6 pages).

Overbeek, "Factors affecting transgenic animal production," Transgenic Animal Technology, 1994, pp. 96-98.

Partial European Search Report dated Jun. 9, 2004 from related European Patent Application No. 01987119.3; 4 pages.

Petersen, T. et al., Characterization of the gene for human plasminogen, a key proenzyme in the fibrinolytic system, J. Biol. Chem., Apr. 15, 1990, pp. 6104-6111, vol. 265, No. 11.

Supplementary European Search Report dated Feb. 12, 2008 from related European Patent Application No. 03813462.3; 3 pages.

* cited by examiner

Figure 1
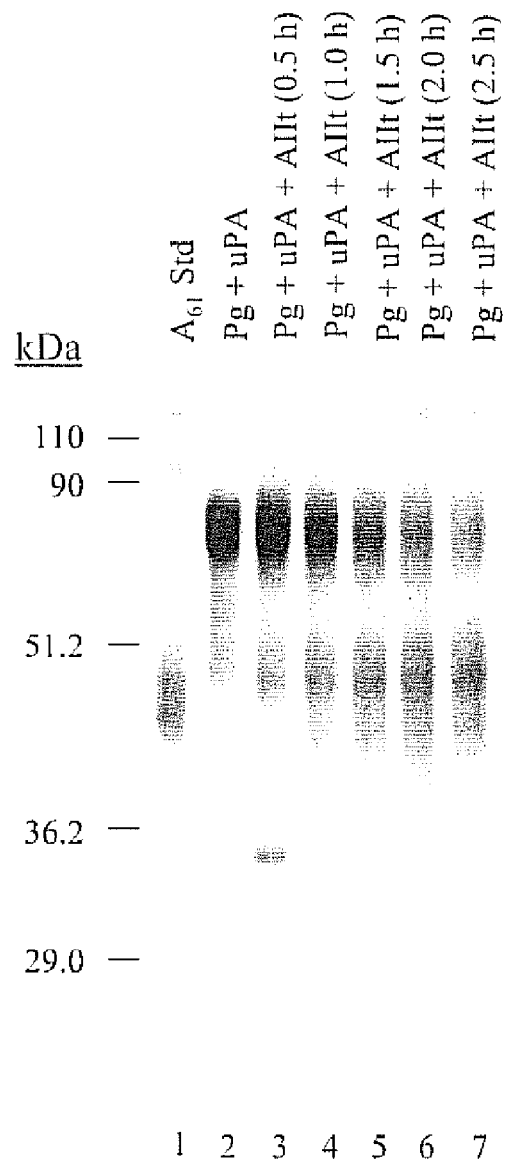
Coomassie Blue staining
Fig. 1C
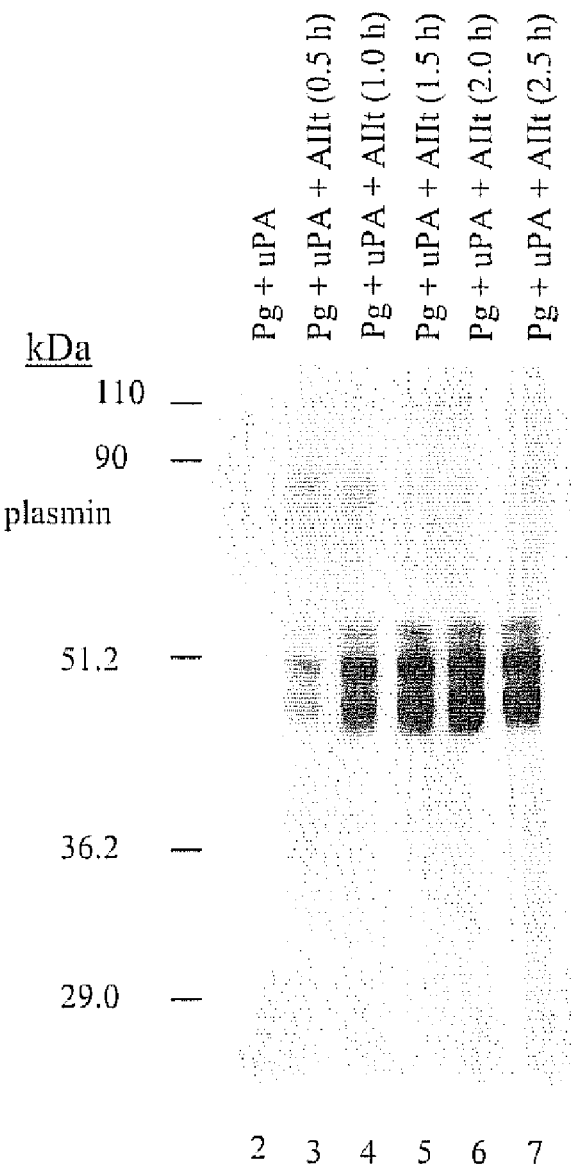
Streptavidin-HRP blot
Fig. 1D

Figure 2-B
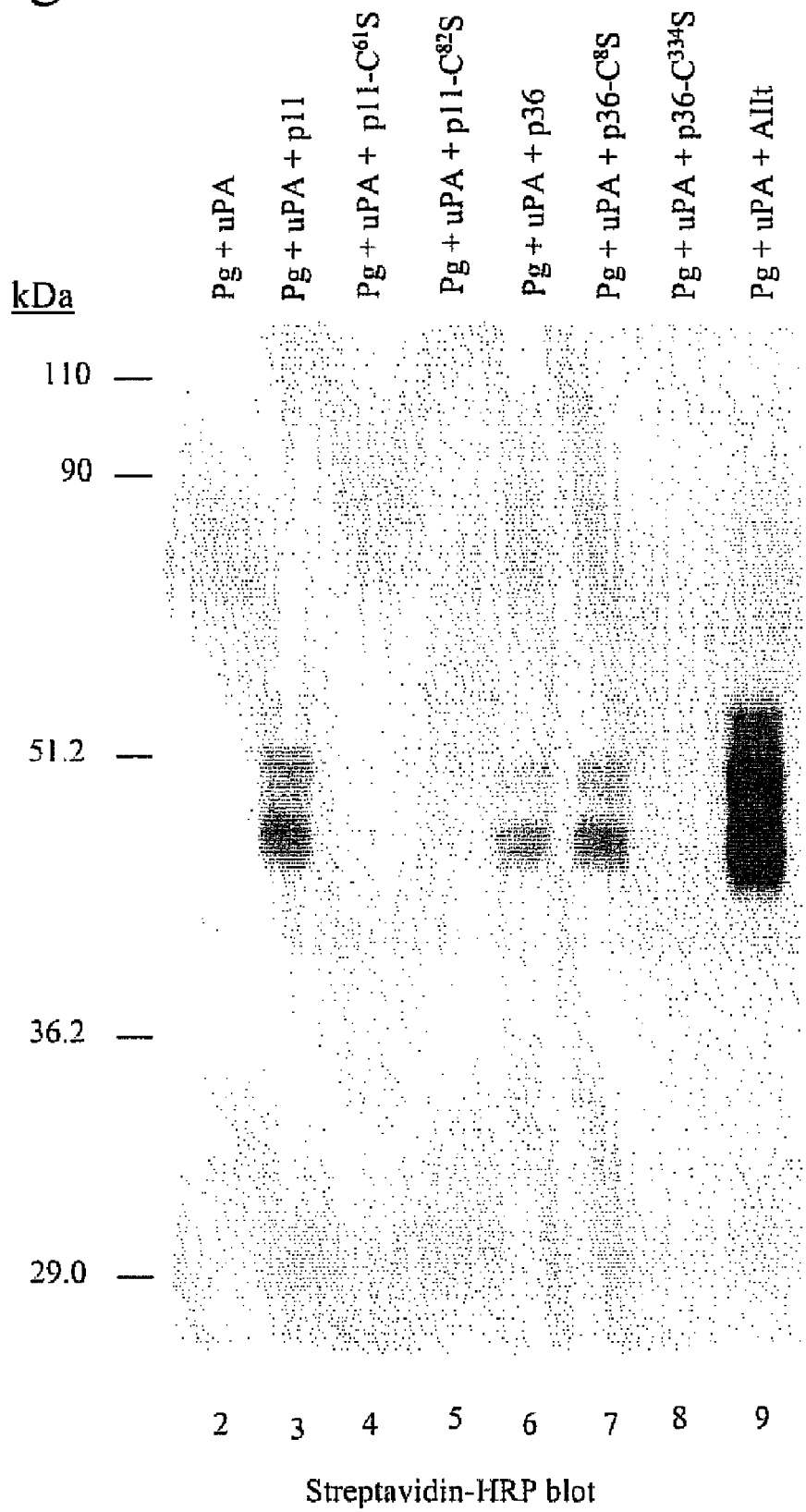
Streptavidin-HRP blot

Streptavidin-HRP blot

Streptavidin-HRP blot

Streptavidin-HRP blot

D

E

A

B

C

Figure 18
Fig 18A
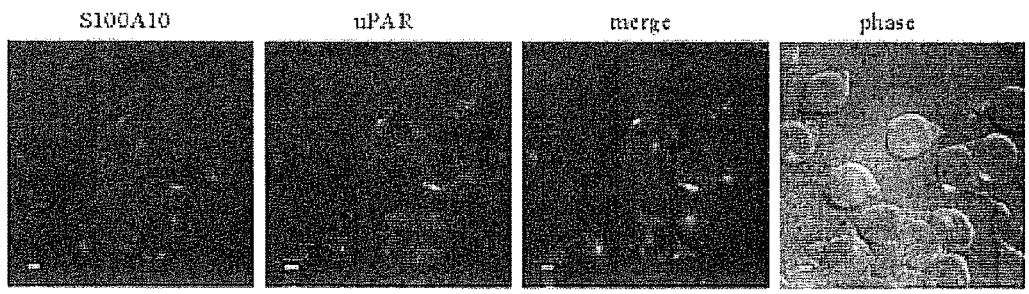
Fig. 18B
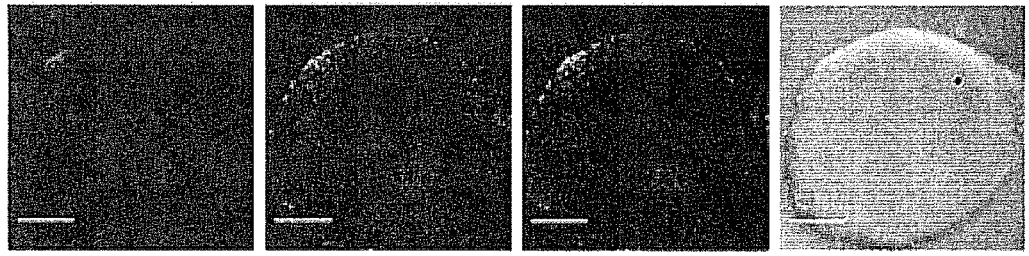
Bar: 10μm
Fig 18C
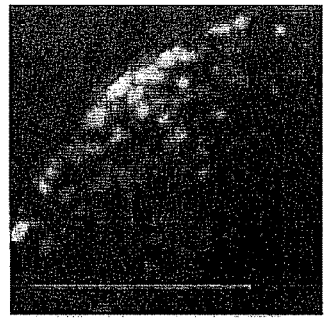
Bar: 10μm
Fig 18D
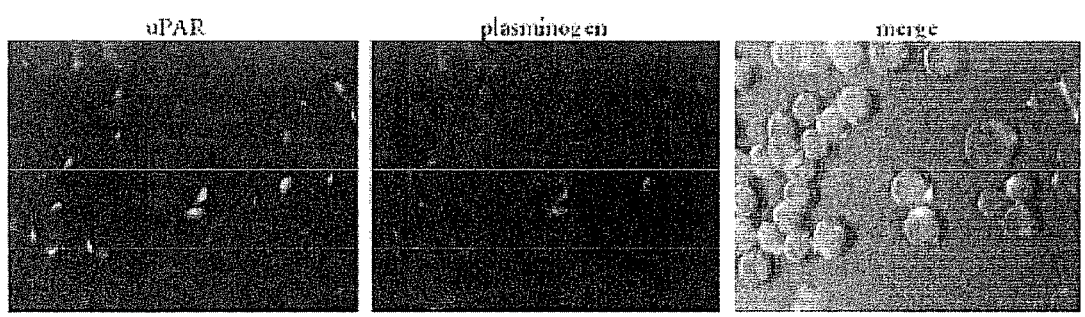

Figure 19
Fig 19A
Vector control: S100A10 / Annexin A2
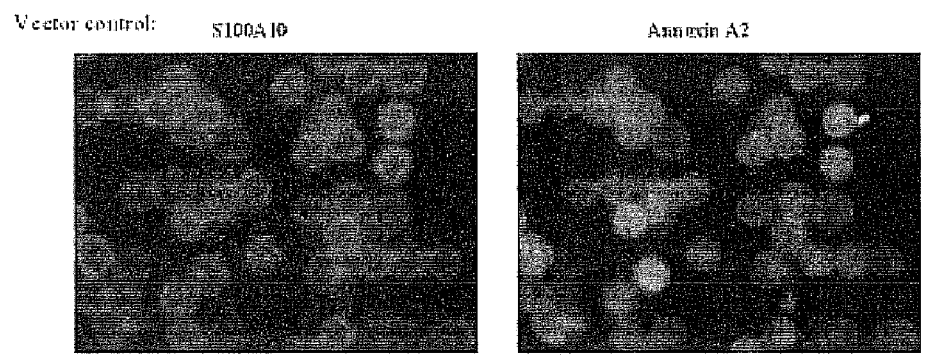
Fig 19B
RNAi:
Fig 19C
*Non-permeabilized*   RNAi   RNAi+S100A10   Vector control
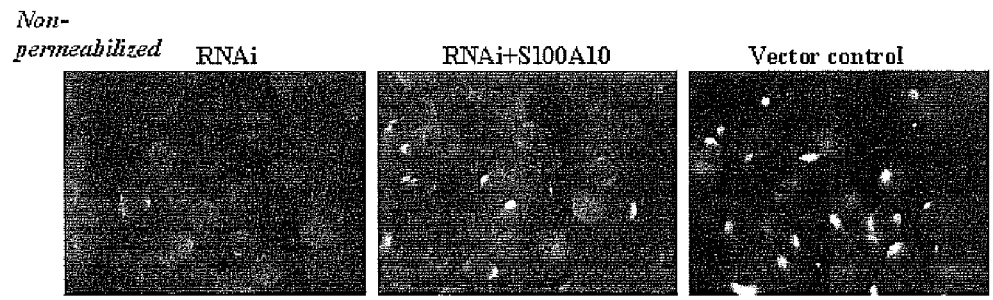
Fig 19D   *Permeabilized*
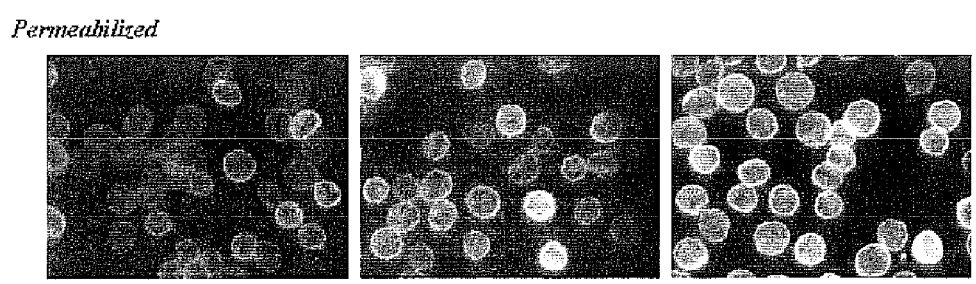

Figure 20
Fig 20A
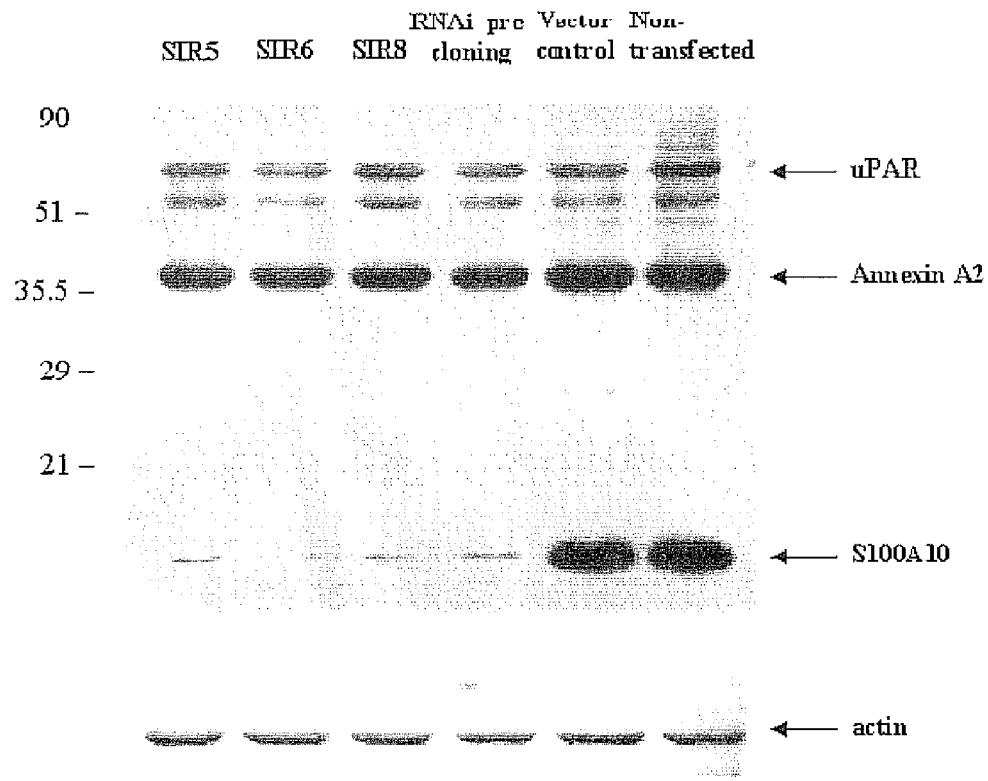
Fig 20B
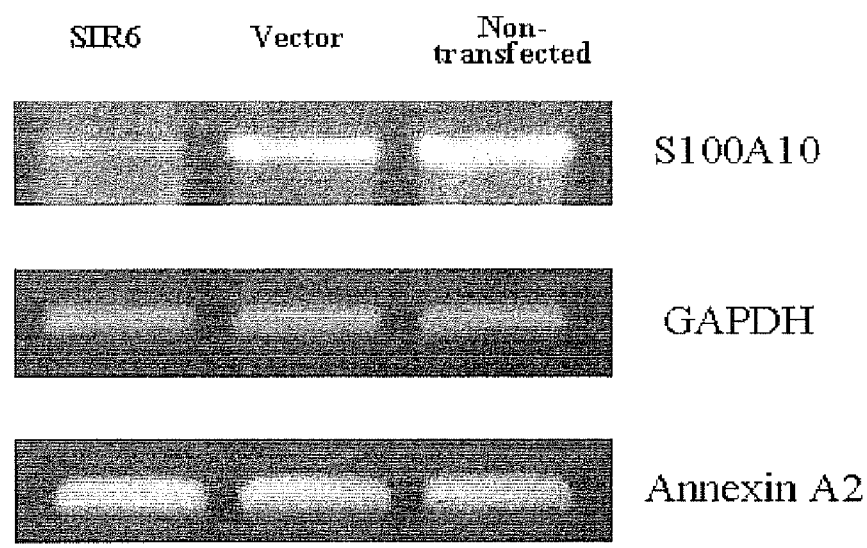

Figure 21
Fig 21A
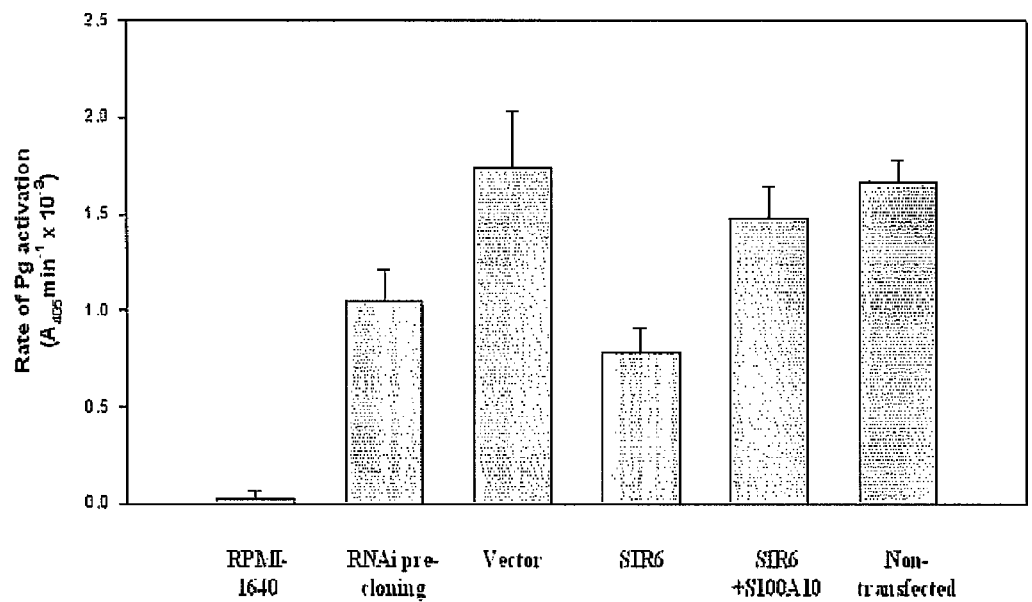
Fig 21B
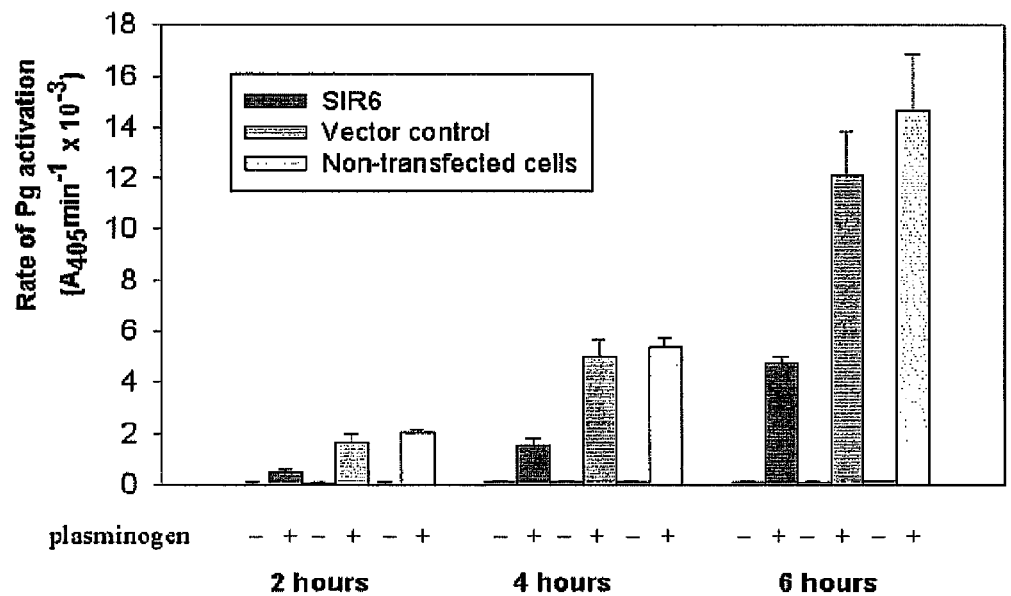

Figure 22
Fig 22A
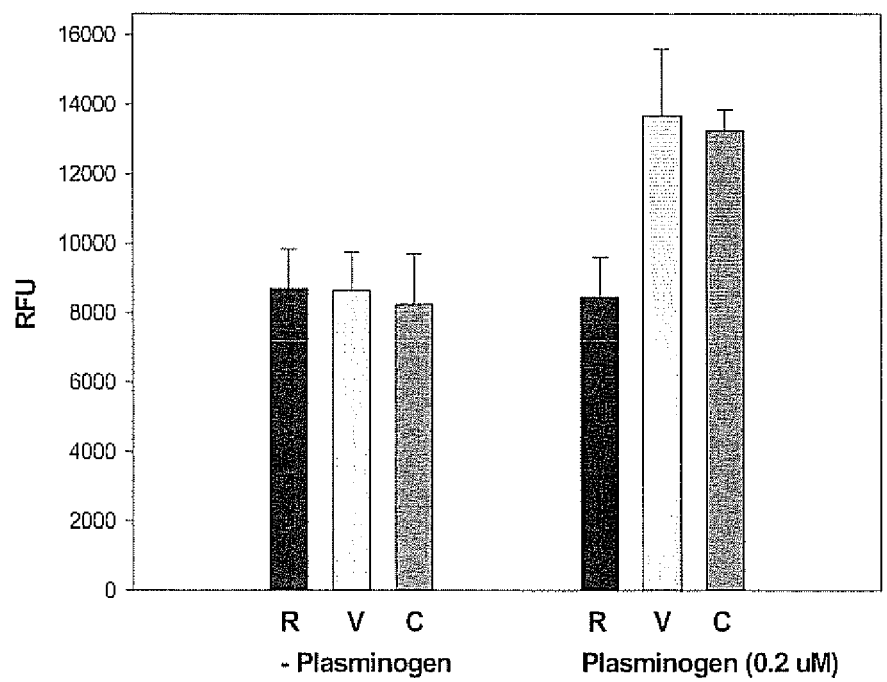
Fig 22B
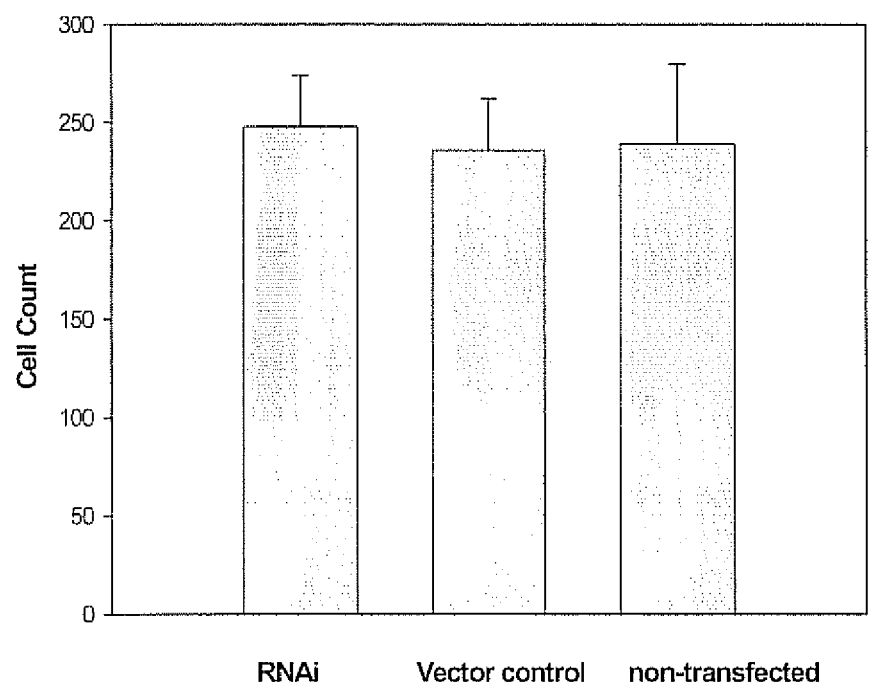

CCL-222 + HFF

CCL-222+HFF+Pg

COMPOSITIONS AND METHODS FOR INHIBITING TUMOR GROWTH AND METASTASIS

CROSS REFERENCE TO RELATED APPLICATIONS

This application is a divisional of U.S. patent application Ser. No. 11/621,629, filed on Jan. 10, 2007, now abandoned, which is a divisional of U.S. patent application Ser. No. 10/735,577, now abandoned, filed on Dec. 12, 2003, which claims benefit of priority to U.S. Provisional Patent Application 60/433,140, filed Dec. 13, 2002, and is a continuation-in-part of U.S. patent application Ser. No. 10/304,287, filed on Nov. 26, 2002, which issued as U.S. Pat. No. 7,250,271 on Jul. 31, 2007, and which claims priority to U.S. Provisional Patent Application 60/333,866, filed Nov. 28, 2001, which is now abandoned.

GOVERNMENT SUPPORT

This work was supported in part by a grant from the National Institutes of Health (CA78639). The United States Government has certain rights in this invention.

SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821 (f).

BACKGROUND OF THE INVENTION

1. Field of the Invention

This invention is directed to methods of modulating the activity of a p11 protein, which is shown to be involved in the regulation of tumor cell invasion, tumor growth and tumor metastasis. Disclosed are antisense polynucleotides, sense polynucleotides, siRNAs and other compositions, which modulate the activity of p11. It is disclosed herein that p11 is involved in the production of plasmin, the degradation of the extracellular matrix ("ECM"), the invasion of cells, including tumor cells, into the ECM, the growth of tumors, and the establishment of metastatic tumor foci.

2. Description of the Related Art

Anti-angiogenic Plasminogen Fragments ("AAPFs")

Annexin II heterotetramer ("AIIt") is a $Ca^{2+}$-binding protein complex that binds t-PA, plasminogen and plasmin and stimulates both the formation and autoproteolysis of plasmin at the cell surface (Kassam et al. (1998[a]) *J. Biol. Chem.* 273, 4790-4799; Kassam et al. (1998[b]) *Biochemistry* 37, 16958-16966; Fitzpatrick et al. (2000) *Biochemistry* 39, 1021-1028; reviewed in Kang et al. (1999) *Trends. Cardiovasc. Med.* 9, 92-102). The protein consists of two copies of an annexin II 36 kDa subunit (p36) called annexin II A2 and two copies of an 11 kDa subunit (p11) called S100A10. It is known in the art that the carboxyl-terminal lysines of the p11 subunit plays a key role in plasminogen binding and activation (Kassam et al, 1998(b)).

Angiostatin was originally identified in the urine of mice bearing Lewis lung carcinoma (LLC) as a 38 kDa proteolytically-derived fragment of plasminogen which encompassed the first four kringle domains of plasminogen ($Lys^{78}$-$Ala^{440}$ according to SEQ ID NO:1). Angiostatin was shown to be a potent antiangiogenic protein that inhibited the growth of human and murine carcinomas and also induced dormancy in their metastases. Angiostatin was also characterized as a specific antiangiogenic protein that blocked microvascular endothelial cell proliferation but not the proliferation of non-endothelial cells (O'Reilly et al. (1994) Cold Spring Harb Symp Quant Biol 59, 471-482).

Angiostatin is a member of a family of anti-angiogenic plasminogen fragments ("AAPFs"). Physiologically relevant AAPFs include a 38 kDa AAPF isolated from the conditioned media of tumor-infiltrating macrophages (Dong et al. (1997) Cell 88, 801-810), a 43 kDa and 38 kDa AAPF identified in the conditioned media of Chinese hamster ovary and HT1080 fibrosarcoma cells and a 48 kDa AAPF present in macrophage conditioned media (Falcone et al. (1998) J. Biol. Chem. 273, 31480-31485). Other AAPFs include a 43 kDa and a 38 kDa AAPF isolated from the conditioned media of human prostate carcinoma PC-3 cells (Gately et al. (1996) Cancer Res. 56, 4887-4890; Gately et al. (1997) PNAS USA 94, 10868-10872) and AAPFs of 66, 60 and 57 kDa detected in the conditioned media of HT1080 and Chinese hamster ovary cells (Stathakis et al. (1999) J Biol Chem 274, 8910-8916). Since the carboxyl-terminus of most of these AAPFs was not determined, the exact primary sequence of most of the AAPFs is unknown.

Two distinct pathways have been identified for the formation of AAPFs. First, certain proteinases can directly cleave plasminogen into AAPFs. These proteinases include metalloelastase, gelatinase B (MMP-9), stromelysin-1 (MMP-3), matrilysin (MMP-7), cathepsin D and prostate-specific antigen (Patterson, B. C. and Sang, Q. A. (1997) J Biol Chem 272, 28823-28825; Cornelius et al. (1998) J. Immunol. 161, 6845-6852; Lijnen et al. (1998) Biochemistry 37, 4699-4702; Morikawa et al. (2000) J. Biol. Chem.; Heidtmann et al. (1999) Br. J. Cancer 81, 1269-1273). The source of these proteinases may be tumor-infiltrating macrophages (Dong et al., 1997) or the cancer cells themselves. For example, the conversion of plasminogen to angiostatin by macrophages is dependent on the release of metalloelastase from these cells. In comparison, Lewis lung carcinoma cells release MMP-2 which also cleaves plasminogen to angiostatin (O'Reilly et al. (1999) J Biol Chem 274, 29568-29571). Second, AAPFs are also generated by a three step mechanism which involves the conversion of plasminogen to plasmin by urokinase-type plasminogen activator ("uPA"), the autoproteolytic cleavage of plasmin and the release of the resultant plasmin fragment by cleavage of disulfide bonds. The cleavage of the plasmin disulfide bonds can be accomplished by free sulfhydryl group donors (FSD) such as glutathione or by hydroxyl ions at alkaline pH (Gately et al., 1996; Gately et al., 1997; Wu et al. (1987) PNAS USA 84, 8793-8795; Kassam et al. (2001) J Biol. Chem. 276, 8924-8933). Alternatively, the plasmin disulfide bonds can be cleaved enzymatically by a plasmin reductase such as phosphoglycerate kinase (Stathakis et al. (1997) J Biol Chem 272, 20641-20645; Lay et al. (2000) Nature 408, 869-873).

In co-pending patent application PCT/US01/44515 (published as WO0244328 A) and Kassam et al. (2001) J Biol Chem. 276, 8924-8933, which are incorporated herein by reference, it was shown by the inventor that the primary AAPF present in mouse and human blood has a molecular weight of 61 kDa. This AAPF, called $A_{61}$, was produced in a cell-free system consisting of u-PA and plasminogen. $A_{61}$ was shown to be a novel four-kringle containing plasminogen fragment consisting of the amino acid sequence, $Lys^{78}$-$Lys^{468}$ (SEQ ID NO:1) (Kassam et al., 2001). The release of $A_{61}$ from plasmin required cleavage of the $Lys^{468}$-$Gly^{469}$ (SEQ ID NO:1) bond by plasmin autoproteolysis and also cleavage of the Cys$^{462}$-Cys$^{541}$ (SEQ ID NO:1) disulfide bond. Since A$_{61}$ was generated in a cell-free system from plasmin at alkaline pH in the absence of sulfhydryl donors, it was concluded that cleavage of the Cys$^{462}$-Cys$^{541}$ disulfide was catalyzed by hydroxyl ions in vitro. In contrast, at physiological pH, it was observed that the conversion of plasminogen to A$_{61}$ was very slow. These results contrasted with the observation that at physiological pH, HT1080 fibrosarcoma and bovine capillary endothelial (BCE) cells stimulated the rapid formation of A$_{61}$. Heretofore, the mechanism by which these cells stimulated plasmin reduction and the release of A$_{61}$ from plasmin was unclear.

Metastasis

Tumor cells are capable of escaping the constraints imposed by neighboring cells, invading the surrounding tissue and metastasizing to distant sites. This invasive property of tumor cells is dependent on the activation of proteases at the cell surface. It is generally accepted in the art that a critical factor in tumor cell invasiveness and metastasis is plasminogen activation. Plasminogen activation by cancer cells is initiated by the release of the plasminogen activator, urokinase-type plasminogen activator ("uPA") which catalyzes the proteolytic conversion of the inactive zymogen plasminogen to the active broad-spectrum protease, plasmin, which is capable of catalyzing the degradation of proteins of the basement membrane and extracellular matrix such as laminin and fibronectin (Andreasen et al., 1997, Int J Cancer 72:1-22; Tapiovaara et al., 1996, Adv Cancer Res 69:101-133)). In addition, plasmin activates several matrix-degrading metalloproteases (MMPs) (Linjen et al., 1998, Thromb. Haemost 79:1171-1176; Mazzieri et al., 1997, EMBO J. 16:2319-2332). Thus, the generation of plasmin at the cell surface is an important event in the destruction of basement membrane and extracellular matrix that is necessary for the invasion of tumor cells into tissue (Rabbani and Mazar, 2001, Surg Oncol Clin N Am 10:393-416; Mustjoki et al., 1999, APMIS 107: 144-149).

The presence of specific receptors for both uPA and plasminogen at the cell surface is responsible for the spatial and temporal regulation of the conversion of plasminogen to plasmin (Plow et al., 1986, J Cell Biol 103:2411-2420; Stephens et al., 1989, J Cell Biol 108:1987-1995). The cell-surface receptor for uPA, urokinase-type plasminogen activator receptor ("uPAR"), acts as a scaffold for the conversion of the zymogen, pro-uPA to the catalytically active form, uPA. Subsequently, the cell surface localized uPA converts the receptor-bound plasminogen to plasmin. Binding of plasminogen to its cell surface receptors is thought to be rate-limiting for efficient activation of plasminogen by uPA (Stephens et al., 1989; Namiranian et al., 1995, Biochem J 309:977-982).

Prior to the instant invention, the identity of cellular receptors for plasminogen, which participate in uPA-dependent plasminogen activation, had not been established. It is known in the art that plasminogen binds to cells with low affinity (K$_d$=0.3-2 μM) and high capacity (10$^4$-10$^7$ binding sites per cell). The plasminogen binding sites on cells are heterogeneous in nature and both proteins and non-proteins such as glycosaminoglycans and gangliosides participate in plasminogen binding. A series of studies established the paradigm that only a small subset of cellular plasminogen receptors, those that possess a carboxy-terminal lysine residue, participate in cell surface plasminogen activation (reviewed in Felez, J., 1998, Fibrinolysis & Proteolysis 12:183-189). Candidate plasminogen receptors possessing carboxy-terminal lysines include p11 (Kassam et al., 1998, Biochemistry 37:16958-16966; Kassam et al., 1998, J Biol Chem 273: 4790-4799; Fitzpatrick et al., 2000, Biochemistry 39:1021-1028), cytokeratin-8 (Hembrough et al., 1995, J Cell Sci 108:1071-1082; Hembrough et al., 1996, J Biol Chem 271: 25684-25691; Kralovich et al., 1998, J Protein Chem 17:845-854), TIP49a (Hawley et al., 2001, J Biol Chem 276:179-186), and α-enolase (Miles at al., 1991, Biochemistry 30:1682-1691; Redlitz and Plow, 1995, Baillieres Clin Haematol 8:313-327; Pancholi, V., 2001, Cell Mol Life Sci 58:902-920).

Mainly characterized as an intracellular protein, p11 (also known in the art as, and used interchangeably with "S100A10") is continuously expressed on the surface of different types of cells along with its binding partner, annexin II (or annexin II A2, a.k.a. p36) (Kassam et al., 1998b; Yeatman et al., 1993, Clin Exp Metastasis 11:37-44; Mai et al., 2000, J Biol Chem 275:12806-12812). Despite an abundance of in vitro kinetic data (reviewed in Kang et al., 1999, Trands Cardiovasc Med 9:92-102; Choi et al., in press, and Filipenko, 2002 18275, id), the issue of whether p11 plays an important role in the regulation of cellular plasmin generation or activity has not been addressed. Interestingly, the p11 message was observed to be upregulated in human renal cell carcinoma and gastric adenocarcinoma (Teratani, et al., 2002, Cancer Lett 175:71-77; EI-Rifai et al., 2002, Cancer Research 62:6823-6826), although a role for p11 in the development of cancer has not yet been determined or inferred in these or other publically available references to date. However, copending U.S. application Ser. No. 10/304,287 (filed on 26 Nov. 2002), which is incorporated herein by reference, teaches that p11 has plasmin reductase activity and is therefore useful in the production of antiangiogenic plasmin fragments ("AAPFs").

SUMMARY OF THE INVENTION

AIIt Compositions and Methods

According to the present invention, it was discovered that an annexin II heterotetramer or its subunits stimulates the conversion of plasminogen to A$_{61}$ in vitro. It was also discovered that an annexin II heterotetramer or its subunits (p36, p11) possesses an intrinsic plasmin reductase activity, and that the cysteinyl residues of both subunits of the annexin II heterotetramer (i.e., p36 and p11) participate in the reduction of plasmin. Preferred Annexins include annexin II (p36) and AIIt. The invention is also drawn to inhibitors of AIIt activity, which diminish A$_{61}$ production by cells. Preferred inhibitors of AIIt activity include antisense nucleotides, which downregulate expression of AIIt on the surface of cells.

The present invention is drawn to a method of producing an anti-angiogenesis plasmin fragment comprising contacting a plasminogen polypeptide with a plasminogen activator and a plasmin reductase, wherein a reduced plasmin protein is produced. The anti-angiogenesis plasmin fragment, which has anti-angiogenesis activity, is released from the reduced plasmin protein. Preferably but not exclusively, the plasminogen activator is a urokinase-type plasminogen activator, a plasmin reductase is an annexin II heterotetramer, annexin II p36 subunit, or p11 and the anti-angiogenesis plasmin fragment is an A$_{61}$ corresponding to SEQ ID NO:7 or SEQ ID NO:8.

In another embodiment, the present invention is drawn to a method of producing an anti-angiogenesis plasmin fragment comprising contacting a plasmin protein with a plasmin reductase, wherein the anti-angiogenesis plasmin fragment, which has anti-angiogenesis activity, is released from a reduced plasmin protein. Preferably but not exclusively, the plasmin reductase is an annexin II heterotetramer, annexin II p36 subunit, or p11, and the anti-angiogenesis plasmin fragment is an $A_{61}$ corresponding to SEQ ID NO:7 or SEQ ID NO:8.

In another embodiment, the present invention is drawn to a method of inhibiting the formation of an $A_{61}$ anti-angiogenesis fragment comprising contacting a cell with a polynucleotide, wherein (a) the polynucleotide encodes a p11 antisense polynucleotide, which enters the cell inhibits the expression of p11 on the surface of the cell, and (b) expression of p11 is required for efficient production of the $A_{61}$ anti-angiogenesis fragment.

In another embodiment, the present invention is drawn to a method of increasing the formation of an $A_{61}$ anti-angiogenesis fragment comprising contacting a cell with a polynucleotide, wherein (a) the polynucleotide encodes a p11 sense polynucleotide, which enters the cell increases the expression of p11 subunits on the surface of the cell, and (b) expression of p11 is required for efficient production of the $A_{61}$ anti-angiogenesis fragment.

p11 Modulation

To determine the role of p11 in plasmin formation, plasminogen activation, cell invasiveness, tumor growth and metastasis, human cancer cells were contacted with a composition that modulates p11 activity (e.g., antisense or sense p11 cDNA, or p11-specific siRNA). The effects of the changes in the expression of the p11 in those human cancer cells subsequent to treatment with the p11-modulating composition were determined. According to the instant invention, it was discovered that p11 accounts for about 80-90% of the plasmin generating capacity of the human cancer cells. More importantly, these changes in p11-regulated plasmin-generation correlated with changes in cellular invasiveness, metastatic potential of tumor cells and tumor growth. Furthermore, it was discovered that when p11 levels are reduced in a cell, such as for example by treatment of the cell with a p11-specific siRNA, (a) the plasmin generating activity of the cell is significantly reduced, (b) the specific binding of plasminogen to the cell is significantly reduced, (c) the invasiveness of the cell (e.g., for cancer cell types) is significantly reduced or eliminated, (d) the expression and activity of various matrix metalloproteinases ("MMPs") are reduced or otherwise modulated, and (e) the level of annexin A2 (a.k.a. p36) in the cell is not significantly affected, relative to similar cells in which the levels of expression of p11 are not reduced.

In view of these discoveries, the present invention is directed to compositions that modulate (either up or down) the activity of p11 of a cell. Compositions include, but are not limited to antisense p11 polynucleotides, sense p11 polynucleotides, small interfering RNAs ("siRNA") specific to p11, inhibitory antibodies to p11, p11-receptor blocking peptides, p11 antagonists, p11 agonists, and soluble fragments of the p11 protein receptor. A preferred antisense p11 polynucleotide comprises a sequence as set forth in any one of SEQ ID NO:13, SEQ ID NO:14, SEQ ID NO:15, or SEQ ID NO:16. A preferred sense p11 polynucleotide comprises a sequence as set forth in SEQ ID NO:17, or a fragment thereof (i.e., which encodes the open reading frame of p11). siRNAs are described by SEQ ID NOs:18-144. Preferred siRNAs are described by SEQ ID Nos:18-24. A more preferred p11-specific siRNA comprises SEQ ID NO:22 and SEQ ID NO:24.

In another embodiment, the invention is directed to methods of modulating the activity of p11 in a cell comprising administering to the cell an effective amount of a composition that modulates the activity of p11. Preferred cells are human cancer cells, such as HT1080 fibrosarcoma cells and Colo 222 colorectal cancer cells.

In other embodiments, the invention is directed to (a) methods for reducing the development of cancer in patients in need thereof, (b) methods for inhibiting the growth of tumors in patients in need thereof, and (c) methods for inhibiting tumor cell invasion, comprising administering to a cell an effective amount of a composition that modulates the activity of p11. Preferred cells are human cancer cells.

Other embodiments of this invention are directed to (a) clonal cell lines useful toward the identification of compositions that modulate p11 activity, (b) methods of making these clonal cell lines and (c) methods of using these clonal cell lines in the identification of compositions that modulate p11 activity. Preferred methods of making clonal cell lines involve characterizing the expression levels in these cells of one or more proteins that are involved in the plasminogen activation pathway. Preferred methods of using these clonal cell lines in the identification of p11 modulators comprise contacting the clonal cells with a prospective composition, then assessing the activity of p11. A preferred activity of p11 is plasminogen activation of the cells. In another embodiment, the invention is directed to a cell line that has altered expression of p11. Preferably, the cell line comprises a siRNA that affects expression of p11. More preferably, the cell line is a SIR6 cell line (infra).

p11 in a Proteolytic Hub

The inventor has also discovered that the p11 protein colocalizes to a region of the cell membrane, called a proteolytic hub, which comprises uPAR or EMMPRIN. Thus, in another embodiment, the invention is directed to methods of regulating the activity, structure and formation of a proteolytic hub on a cell mambrane comprising the step of modulating p11, p36 or AIIt expression or activity.

BRIEF DESCRIPTION OF THE DRAWINGS

FIG. 18. Colocalization of S100A10, uPAR, and plasminogen on the CCL-222 cell surface. Cells grown on glass coverslips were fixed with 4% Paraformaldehyde (PFA) and stained for both S100A10 and uPAR using anti-S100A10 monoclonal antibody and anti-uPAR polyclonal antibody, as described in the FIG. 1 legend. Immunofluorescence photomicrographs detailing the extracellular expression of S100A10 and uPAR are compared at low (2A, D) and higher (2B, C) magnification using confocal microscopy. C, a patch of p11/uPAR immunofluorescence consisting of a 0.3 m thick optical section, was analyzed by confocal microscopy and illustrates the colocalization of S100A10 and uPAR. D, non-permeabilized CCL-222 colorectal cells were treated with anti-plasminogen monoclonal and anti-uPAR polyclonal antibodies followed by Alexa-labeled (green) and Cy3-labeled (red) secondary antibodies. uPAR and plasminogen colocalize on CCL-222 cell surface. Scale bar represents 10 μm.

FIG. 20. Specificity of S100A10 gene knock-down. A, S100A10, annexin A2 and uPAR expression in several pSUPER-S100A10 transfected clonal cell lines was compared. Of the three established cell lines, clone SIR6 showed the lowest total cellular levels of S100A10. S100A10 mRNA levels were also examined by RT-PCR in clone SIR6. As shown in B, S100A10 mRNA levels of SIR6 cells were reduced as compared to the pSUPER-Con cells or parental cells. Furthermore, annexin A2 mRNA levels were unchanged in all cell lines.

FIG. 22. Role of S100A10 in cellular invasiveness. A, CCL-222 parental cells (C), SIR6 (R) and pSUPER-Con transfectant (V) were incubated in the absence or presence of 0.2 μM plasminogen. Cell invasiveness was examined with Matrigel-coated invasion chambers. Invasive cells were lysed and stained with CyQuant GR dye. B, cell migration was assessed with Boyden chamber inserts. Migratory cells were fixed with 4% PFA and stained with crystal violet. For quantification, the cells were counted in 10 random fields under a light microscope (400x).

DETAILED DESCRIPTION OF THE INVENTION

Figures 1A, 1B:
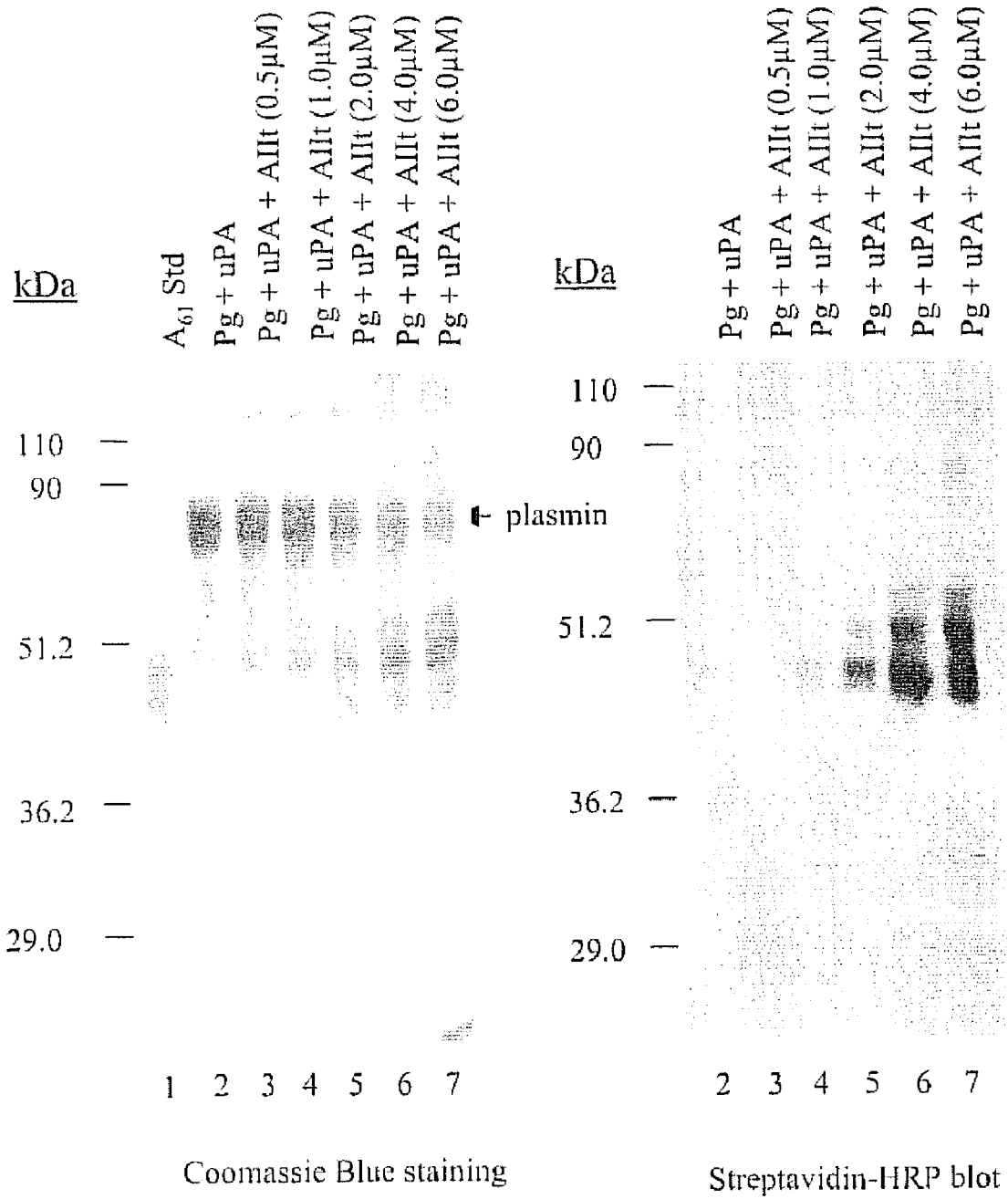
FIG. 1 illustrates the stimulation of conversion of plasminogen to $A_{61}$ by AIIt. (A,B) AIIt dose-dependent generation of $A_{61}$. [Glu]-plasminogen (4 µM) was incubated with u-PA (0.075 µM) and various concentrations of AIIt, then subjected to non-reduced SDS-PAGE followed by Coomassie blue staining (A). Portions of the reaction mixtures were incubated with MPB (100 µM), reduced glutathione (200 µM), iodoacetamide (400 µM), L-lysine-Sepharose, and then subjected to non-reduced SDS-PAGE followed by Western blot with streptavidin-HRP (B). (C,D) Time-course generation of $A_{61}$. [Glu]-plasminogen (4 µM) was incubated with u-PA (0.075 µM) and AIIt (4 µM) for various times at 37°. The results are shown as Coomassie blue staining (C) and Western blot with streptavidin-HRP (D).

Unless defined otherwise, all technical and scientific terms used herein have the same meaning as commonly understood by one of ordinary skill in the art to which this invention belongs. Although any methods or materials similar or equivalent to those described herein can be used in the practice or testing of the present invention, the preferred methods and materials are described. For the purposes of the present invention, the following terms are defined below.

The phrase "anti-angiogenesis plasmin fragment" ("AAPF"), as used herein, means a polypeptide fragment of plasminogen or plasmin, which inhibits the recruitment or growth of blood vessels, or the recruitment or growth of endothelial cells, wherein the plasminogen or plasmin may be from any species of metazoan. For example, AAPFs include, p22 and $A_{61}$ (WO0244328 A and Kassam et al., 2001), a 38 kDa AAPF isolated from the conditioned media of tumor-infiltrating macrophages (Dong et al., 1997), a 43 kDa and 38 kDa AAPF identified in the conditioned media of Chinese hamster ovary and HT1080 fibrosarcoma cells, a 48 kDa AAPF present in macrophage conditioned media (Falcone et al., 1998), a 43 kDa and a 38 kDa AAPF isolated from the conditioned media of human prostate carcinoma PC-3 cells (Gately et al., 1996, 1997) and AAPFs of 66, 60 and 57 kDa detected in the conditioned media of HT1080 and Chinese hamster ovary cells (Stathakis et al., 1999). Preferred AAPFs include $A_{61}$.

The term "plasmin protein" means any plasmin protein, which includes active plasmin polypeptide, proteolyzed plasmin, and reduced plasmin, from any species. A preferred plasmin protein has an N-terminal lysine, which corresponds to $Lys^{78}$ of plasminogen.

The phrase "plasminogen activator" means an enzyme that catalyzes the proteolysis of a plasminogen polypeptide to produce an active plasmin protein. Preferred plasminogen activators include urokinase-type plasminogen activators (uPA), streptokinase and tissue-type plasminogen activators (tPA).

The phrase "plasmin reductase" means an agent, preferably a protein, which is capable of catalyzing the reduction of disulfide bridges of a plasminogen polypeptide or plasmin protein. Preferred plasmin reductases include annexin II heterotetramer (used interchangeably with "annexin II tetramer" or "AIIt"), annexin II p36 subunit ("p36"), S100A10 subunit ("p11"), thioredoxin and protein disulfide isomerase.

The phrase "anti-angiogenesis activity" means the ability of a substance to (a) inhibit endothelial cell proliferation or migration, (b) kill proliferating endothelial cells, or (c) inhibit the formation of new blood vessels in a tissue. Preferred substances are peptides such as $A_{61}$. Preferred $A_{61}$ polypeptides have a sequence as set forth in SEQ ID NO:7 or SEQ ID NO:8.

The term "angiogenesis" means the formation of new blood vessels in a tissue, the stimulation of endothelial cells to proliferate, or the promotion of survival of proliferating endothelial cells.

The phrase "p11 antisense polynucleotide" means a single stranded RNA molecule, which is complementary to a p11 RNA that can be translated to produce a p11 polypeptide, or a fragment thereof. Functionally, a p11 antisense polynucleotide is capable of decreasing the expression of p11 protein in a cell. A preferred p11 antisense polynucleotide may be a DNA or RNA as set forth in SEQ ID NO:5, SEQ ID NO:13, SEQ ID NO:14, SEQ ID NO:15, SEQ ID NO:16, or any of SEQ ID NO:145-160. The inventors also envision that a siRNA (small interfering RNA) comprising a p11 sequence (e.g., SEQ ID NOs:18-144), which in experiments presented herein below demonstrating the effectiveness in decreasing the expression of p11 in a cell, may be useful in stimulating angiogenesis in a tissue, such as in myopathological heart tissue.

The phrase "p11 sense polynucleotide" means a single stranded RNA molecule, which is can be translated to produce a p11 polypeptide, or a fragment thereof. Functionally, a p11 antisense polynucleotide is capable of increasing the expression of p11 protein in a cell. A preferred p11 sense polynucleotide may be a DNA or RNA as set forth in SEQ ID NO:6. The terms "p11", "p11 polypeptide", "p11 protein", "p11 subunit", "annexin II p11", "annexin II p11 subunit", "S100A10", and "S100A10 subunit" are equivalent and are used interchangeably throughout the instant specification and claims.

The term "vector" refers to a polynucleotide that enables the expression of a constituent polynucleotide in a cell, wherein expression means the transcription of DNA into a RNA. Preferred vectors include retroviral vectors, such as pLin for the expression of antisense polynucleotides, and vectors that enable the continuous or stable expression of siRNAs, such as pSUPER.

As used herein, the phrase "modulation (or modulating) the activity of p11" means any change, either increasing (up) or decreasing (down), in any cellular activity associated with p11, relative to the p11 activity of a similar cell, which had not been affected by a composition that modulates the activity of a p11 protein. For example, modulation may be effected by a change in the expression of a gene encoding p11, the transcription of a p11 gene or cDNA into a RNA, the translation of a p11 RNA into protein, the post-translational modification of a p11 protein, the cellular or extracellular localization of a p11 protein, the amount of p11 localized in or on the cell membrane or inside the cell, the allosteric regulation of p11, or in the plasminogen-activating activity of p11.

As used herein, the phrase "p11 activity" or "activity of p11" refers to any direct biochemical activity of p11 or indirect activity associated with p11. These activities include localization of plasminogen to the cell membrane or surface, plasminogen binding, activation of plasminogen, conversion of plasminogen to plasmin, proteolysis of plasmin, generation of antiangiogenic plasmin fragments, release of proteolytic activity from cells into the extracellular space or matrix, proteolysis of extracellular matrix (including basement membrane) proteins, proteolysis of gelatin, cell invasion through barriers such as Matrigel™ or extracellular matrices, proteolytic activation of plasminogen activators (such as uPA, tPA), the formation of metastatic tumor foci, and the development of cancer or growth of tumors.

As used herein, the phrase "cancer development" refers to the initiation of tumor formation in a patient, the growth of tumors in a patient, or the spread of tumors throughout a patient. Tumors comprise cancer cells. Preferred patients are mammals, which include humans and mice.

As used herein, the phrase "tumor growth" refers generally to the rate of growth of a tumor mass in a subject. Preferred subjects are human patients.

As used herein, the phrase "cell invasion" refers to the ability of a cell to migrate through a physiological barrier or to proteolyze components of an extracellular matrix. Preferred physiological barriers include basement membranes and other extracellular matrices, which are well known in the art. Cell invasion is correlated to the secretion or excretion of proteolytic enzymes from a cell. Preferred proteolytic enzymes include plasmin and MMPs.

As used herein, the phrase "clonal cell line" refers to an in vitro or ex vivo culture of cells that are clonally related. Preferred clonal cell lines have well characterized profiles of protein expression, wherein the proteins are directly or indirectly involved in plasminogen activation. Preferred proteins include, p11, uPA, tPA, uPAR, PAI-1 and PAI-2. Non-limiting examples of clonal cell lines include CCL-222 colorectal cells and genetically modified derivatives thereof, and HT1080 fibrosarcoma cells and genetically modified derivatives thereof.

Annexin II Heterotetramer, p36 and p11

The inventors have discovered that an annexin II heterotetramer or its subunits (p36, p11), contains an intrinsic plasmin reductase activity and is useful in the generation of the antiangiogenic plasminogen fragment, $A_{61}$, which is a four-kringle containing plasminogen fragment comprising the amino acid sequence $Lys^{78}$-$Lys^{468}$, wherein the numbering of $Lys^{78}$-$Lys^{468}$ is based upon the numbering of SEQ ID NO:1. It is also disclosed that cells transduced with a vector encoding a p11 antisense RNA ("antisense p11") show reduced extracellular AIIt and $A_{61}$ production, demonstrating the utility of AIIt as an antiangiogenic agent and in the formation of other antiangiogenic agents.

Figure 8:
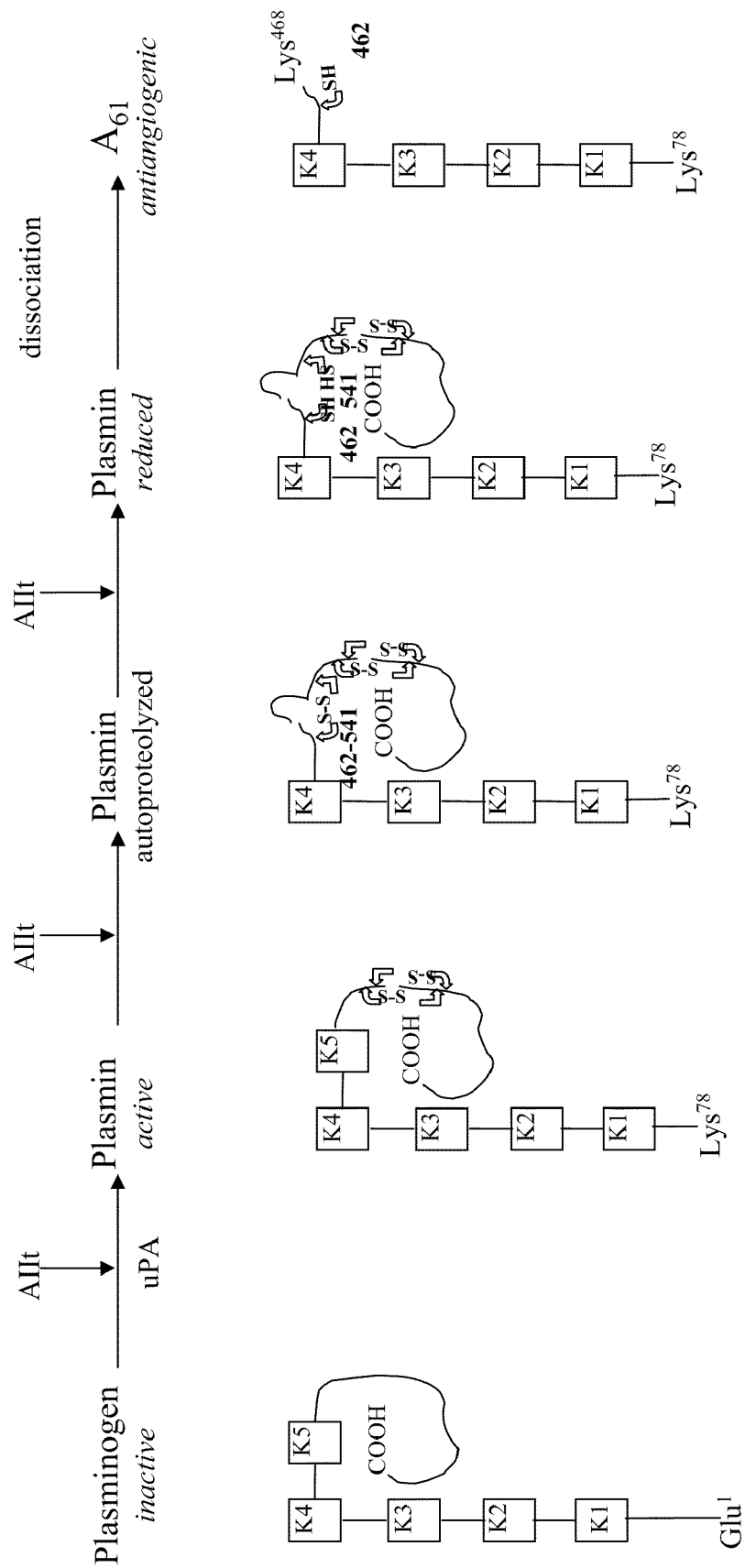
FIG. 8 diagrammatically illustrates the mechanism of $A_{61}$ formation. K represents the kringle domain of plasminogen. S—S indicates the disulfide bond and SH represents the free thiol generated. Plasmin catalyzes the cleavage of the $Lys^{77}$-$Lys^{78}$ and $Lys^{468}$-$Gly^{469}$ bonds of plasminogen.

While not intending to be bound by theory, the inventors postulate that plasminogen is converted to $A_{61}$ in a three-step process (FIG. 8). First, u-PA cleaves the $Arg^{561}$-$Val^{562}$ of plasminogen (SEQ ID NO:1) resulting in the formation of plasmin. Second, plasmin autoproteolysis results in the cleavage of the $Lys^{77}$-$Lys^{78}$ and $Lys^{468}$-$Gly^{469}$ bond. A minor cleavage site at $Arg^{471}$-$Gly^{472}$ has also been shown to be present (minor A61 fragment depicted in SEQ ID NO:8). However, the presence of a $Cys_{462}$-$Cys_{541}$ disulfide prevents release of $A_{61}$ ($Lys^{78}$-$Lys^{468}$).) Third, AIIt catalyzes the reduction of the $Cys^{462}$-$Cys^{541}$ disulfide which allows the release of $A_{61}$ (SEQ ID NO:7, major form) from the rest of the molecule. Since AIIt does not reduce catalytically inactive plasmin, one skilled in the art may conclude that plasmin autoproteolysis must occur before plasmin reduction, suggesting that autoproteolyzed plasmin is the substrate for AIIt's plasmin reductase activity.

It is herein disclosed that plasmin autoproteolysis precedes plasmin reduction and that plasmin reduction is accelerated by AIIt. The AIIt present at the surface of certain cells participates in the conversion of plasminogen to $A_{61}$ and loss of extracellular AIIt results in the inhibition of cell-generated $A_{61}$. AIIt likely functions as a catalyst, since large amounts of plasminogen are converted to $A_{61}$ by AIIt expressing cells. This suggests that in order for AIIt to continually reduce plasmin it must proceed through cycles of oxidation by plasmin and reduction by unknown reducing equivalents. The mechanism by which oxidized extracellular AIIt is reduced is unknown at this time.

It is further disclosed that both the p36 and p11 subunits of AIIt possess plasmin reductase activity. In the case of the p36 subunit the $Cys^{334}$ residue (the cysteine at position number 334 according to SEQ ID NO:2) is essential for plasmin reductase activity. In the case of the p11 subunit both $Cys^{61}$ and $Cys^{82}$ (according to SEQ ID NO:3) are capable of participating in plasmin reduction. Although speculative, the simplest explanation for these observations is that plasmin and autoproteolyzed plasmin can bind to AIIt but the unique conformational change induced by the binding of autoproteolyzed plasmin to AIIt may result in an increased accessibility of cysteinyl residues of AIIt, which participate in reduction of autoproteolyzed plasmin. Since, according to the examples presented below, $Cys^{334}$ of p36 was not labeled with the thiol specific reagent MPB, $Cys^{334}$ of p36 is likely shielded from the solvent. Furthermore, a p36 mutant, which comprises a Cys to Ser substitution at position 334, is inactive in terms of plasmin reductase activity. It is therefore reasonable for one skilled in the art to suspect that $Cys^{334}$ may be shielded and only accessible for reduction of plasmin upon binding of autoproteolyzed plasmin to AIIt.

Protein disulfide reductases typically contain the Cys-X-X-Cys motif in their active sites. Members of this family of proteins include thioredoxin, protein disulfide isomerase, fibronectin, von Willebrand factor and platelet integrin $\alpha_{IIb}\beta_3$ (Terada et al. (1995) J Biol Chem 270, 20410-20416; Soderberg et al. (2000) Cancer Res. 60, 2281-2289; Lahav et al. (2000) FEBS Lett. 475, 89-92; Langenbach, K. J. and Sottile, J. (1999) J Biol Chem 274, 7032-7038; Essex, D. W. and Li, M. (1999) Br. J. Haematol. 104, 448-454; Mayadas, T. N. and Wagner, D. D. (1992) PNAS USA 89, 3531-3535; O'Neill et al. (2000) J Biol Chem 275, 36984-36990). Typically these proteins share the general property of catalyzing the reduction of insulin disulfides. In contrast, AIIt does not contain the Cys-X-X-Cys motif and does not catalyze the reduction of insulin disulfides. This suggests that the intrinsic plasmin reductase activity of AIIt is due to a novel mechanism of disulfide reduction.

The Role of p11 in Cancer

The inventors have discovered that p11, a plasminogen binding protein, is involved in tumor cell invasion, tumor growth and metastasis. It is herein disclosed that the reduction of levels of p11 protein in a tumor cell, which is achievable in myriad ways by one skilled in the art, causes a concomitant reduction in (a) plasminogen activation, (b) plasmin production, (c) extracellular matrix ("ECM") degradation or proteolysis, (d) expression and activity of MMPs, (e) cell invasion through physiological barriers, such as basement membranes or other ECMs, (f) formation of metastatic foci and (g) tumor growth or size. It is further disclosed herein and in copending U.S. patent application Ser. No. 10/304,287 and copending international application PCT/US02/37879 that increasing the levels of p11 facilitates the production of antiangiogenic plasmin fragments ("AAPFs"), which function in vivo to reduce tumor growth. Thus, modulating the activity of p11, either up or down relative to baseline levels, leads to the reduction in tumor development in vivo.

Based upon this surprising discovery, the present invention is directed also to compositions and methods that modulate the activity of p11, which include antisense p11 polynucleotides, sense p11 polynucleotides, small interfering RNAs ("siRNAs") specific to p11, inhibitory antibodies to p11, p11-receptor blocking peptides, p11 antagonists (peptides, peptidomimetics and non-peptidomimetics), p11 receptor agonists (peptides, peptidomimetics and non-peptidomimetics), and soluble fragments of the p11 protein receptor, which bind to p11 and prevent it from engaging its naturally-occurring receptor. The present invention is also drawn to methods of inhibiting tumor growth in a vertebrate animal, including a patient suffering from cancer or at risk of developing cancer, comprising administering to a cell a therapeutically effective amount of a composition that modulates the activity of p11. The present invention is also drawn to methods of decreasing tumor cell invasiveness by administering to a cell a composition that modulates the activity of p11. As is shown in the examples provided herewith (infra), the administration to a human cancer cell of a vector comprising a p11 antisense polynucleotide, wherein the vector enters the cell and allows for the synthesis of a p11 antisense polynucleotide that effectively reduces p11 activity in that cell, causes the cell to have reduced invasiveness. Preferred p11 antisense polynucleotides comprise any sequence as set forth in SEQ ID NO:13, SEQ ID NO:14, SEQ ID NO:15, SEQ ID NO:16, and SEQ ID NOs: 145-160. Also shown is the administration of a sense p11 composition (SEQ ID NO:17 or a fragment thereof, which consists of the p11 open reading frame), which inhibits the development of tumors in vivo upon administration to cancer cells (FIG. 16B).

Various siRNAs that are envisioned to be useful in the modulation of p11 activity include those sequences set forth in SEQ ID NO:25 through SEQ ID NO:144. Preferred siRNAs comprise sequences as set forth in SEQ ID NOs:18-24 (SEQ ID NO:18 represents the "sense" strand of the first siRNA, SEQ ID NO:19 represents the "antisense" strand of the first siRNA, SEQ ID NO:20 represents the "sense" strand of the second siRNA, SEQ ID NO:21 represents the "antisense" strand of the second siRNA, SEQ ID NO:22 represents the "sense" strand of the third siRNA, SEQ ID NO:24 represents the "antisense" strand of the third siRNA; SEQ ID NO:23 is useful as a hairpin structure for the production of any of the aforementioned siRNAs in a cell). Most preferably, the siRNA comprises a sequence set forth in SEQ ID NO:22 and SEQ ID NO:24.

The vector may be viral or non-viral, nucleic acid-based or non-nucleic acid-based. The vector enables the expression of a sense p11 polynucleotide, an antisense p11 polynucleotide or a small interfering RNA ("siRNA") molecule. Preferred vectors include pLin and pSUPER, however, the skilled artisan in the practice of this invention will readily recognize that myriad vectors and control elements may be used to express and drive expression of those polynucleotides that modulate p11 activity. Vectors and other vehicles for the delivery of polynucleotides to cells are well known in the art. Preferred vectors for delivering siRNAs are those vectors that enable stable expression of siRNAs, such as the pSUPER vector, for example. Expression of siRNAs is driven preferably by a promoter, such as for example a histone H1 promoter, which is constitutive in its expression. Viral vectors include at least parvovirus, adenovirus, adeno-associated virus, retrovirus, lentivirus, and herpesvirus-based vectors. Non-viral vectors may be simple plasmids or linear nucleic acids comprising operator sequences, such as promoters, enhancers or silencers. Non-viral vectors may be compositions or methods for getting polynucleotides into cells, including at least physical methods such as gene gun and electroporation, and chemical methods such as cationic lipids or polymers (e.g., Lipofectamine™). Cells may be in vivo, as in a patient, ex vivo or in vitro.

The inventors envision that other compositions that modulate p11 activity ("modulators"), especially those modulators that inhibit p11 activity, would be a peptide, peptidomimetic or nonpeptidomimetic composition comprising a kringle or kringle-like structure with a thiol reagent. Such compositions are envisioned to irreversibly interact with the cys-82 of p11 (the thiol reagent) and also block the C-terminal lysine of p11 (the kringle moiety). Other compositions that are envisioned to be effective in modulating p11 activity include antibodies directed against the C-terminus of p11. Methods for generating polyclonal antibodies, monoclonal antibodies, or reactive fragments thereof are well known in the art.

Figure 16:
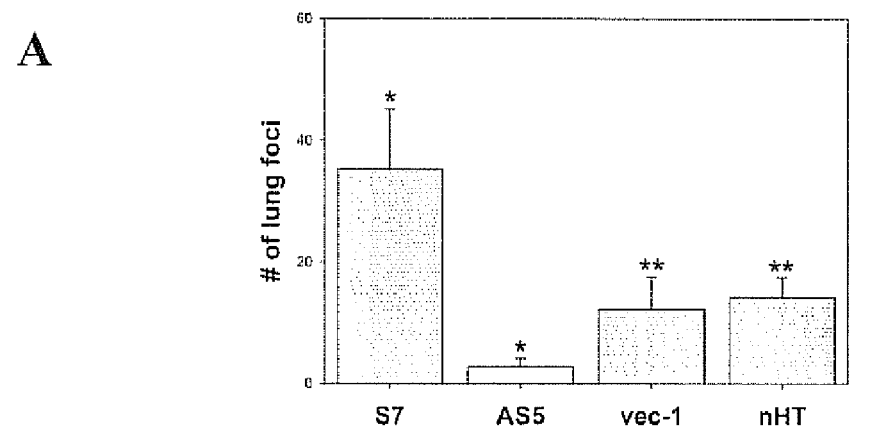
FIG. 16. Role of p11 in tumor formation and metastatic potential of cancer cells. The modulation of levels of p11, either up or down, relative to control cells, results in smaller tumors. A), Metastatic potential of S7 (p11 sense), AS5 (p11 antisense), and Vec-1 (vector alone, no p11 polynucleotides) cells was examined in SCID mice. Five weeks after tail vein injection, mice were sacrificed and lung metastatic foci were counted. B), HT1080 cells were injected intradermally and tumor size measured after 20 days. Thirteen mice were used in each group. C), tumors were dissected from mice after 20 days. 7/13 of p11-antisense and 1/13 p11-sense mice developed tumors.
Figure 16:
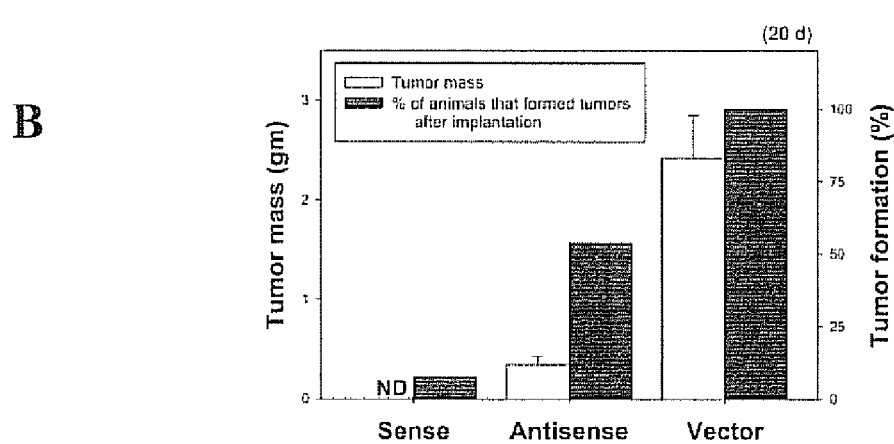
Figure 16:
Figure 16:

It is generally accepted in the art that reduced tumor cell invasiveness is correlated to reduced tumor growth and metastasis in vivo. Therefore, in additional embodiments, the present invention provides methods of treatment to inhibit the development of cancer, tumor growth or tumor metastasis in patients in need thereof. The methods comprise administering to the patient a composition that modulates the activity of p11. In this disclosure and in copending U.S. application Ser. No. 10/304,287, the inventor discloses that p11 participates in the production of antiangiogenic plasmin fragments ("AAPF"), which have been demonstrated to inhibit the growth or formation of tumors in vivo. Thus, application Ser. No. 10/304, 287 and the instant disclosure (supra) teach that an increase in p11 activity may lead to an increase in antiangiogenesis plasmin fragments, which are effective anti-tumor compositions. Additionally, the inventors have discovered that the administration of compounds which reduce the levels of p11 activity cause a reduction in cell invasion and a concomitant reduction in tumor growth and metastasis. Both of these observations, while on the surface seem to contradict one another, actually support the administration of compositions that modulate the activity of p11 either up or down relative to untreated cancer cells to patients in need of treatment for cancer. In other words, it appears as though a proper balance of p11 activity is required for optimal tumor growth. When the proper balance is disturbed, tumor growth is negatively affected. FIG. 16B demonstrates that increasing the activity of p11 in a cancer cell results in a reduction in the number of subjects (in this case mice) that form tumors after injection of cancer cells, relative to those subjects that received cancer cells that express unaltered levels of p11 activity. FIG. 16 also demonstrates that reducing the activity of p11 in a cancer cell (relative to unaltered or untreated cancer cells) results in reduced tumor growth, tumor development and tumor metastasis. Likewise, treatment of another cancer cell line with a specific siRNA, which reduces the expression and activity of p11, results in the reduction of cell invasion through ECM (FIG. 22). Thus, the modulation of p11 activity, either up or down, has a profound influence on tumor development.

The skilled artisan may reasonably expect that the subjects or patients, to which these methods are directed, can be any vertebrate animal. While the known primary structures of p11 are well conserved among vertebrates (e.g., chicken p11 is 89% identical and 97% similar to human p11, as determined by a standard Basic Local Alignment Search Tool (BLAST®) search conducted on the U.S. National Center for Biotechnology Information, National Library of Medicine, National Institutes of Health web site; see Table 1), such that the skilled artisan would reasonably expect p11 to have very similar biochemical properties among vertebrates (and likewise, compositions that modulate p11 activity), preferred patients are mammals; most preferred patients are humans having cancer or at risk for cancer. Nonetheless, the utility of the methods toward any vertebrate can be determined without undue experimentation by administering the composition that modulates the activity of p11 to a cultured cancer cell specific to the vertebrate in question and performing a simple cellular invasion assay, such as the Matrigel™-coated invasion chamber assay or QCM Cell Migration Assay™, as herein described. Reduced cellular invasion relative to untreated cells correlates with a functional composition. Alternatively, the utility of the composition in other vertebrates or cellular systems can also be assessed by evaluating any of the following parameters after administering the composition that modulates the activity of p11 to a cultured cancer cell, (a) plasminogen binding to the cell surface, (b) plasminogen activation, (c) plasmin production, (d) ECM proteolysis or (e) cell invasion. These methods are described herein and are also well known in the art.

TABLE 1

Comparison of vertebrate p11 primary protein sequences to a human p11 protein sequence, according to BLAST ® analysis using the NCBI/NLM/NIH BLAST search engine.

| Organism | GenBank Accession No. | Percent Identity | Percent Similarity |
|---|---|---|---|
| Human | NP 002957.1 | 100% | 100% |
| Pig | P04163 | 100% | 100% |
| Chicken | P27003 | 89% | 97% |
| Mouse | NP 033138.1 | 91% | 96% |
| *Xenopus* | P27004 | 61% | 82% |

The composition that modulates the activity of p11 may be administered to a vertebrate by any suitable route known in the art including, for example, intravenous, subcutaneous, intratumoral, intramuscular, transdermal, intrathecal, or intracerebral. Administration can be either rapid as by injection, or over a period of time as by slow infusion or administration of a slow release formulation.

It is contemplated that the compositions that modulate the activity of p11 are usually employed in the form of pharmaceutical preparations. Such preparations are made in a manner well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is also contemplated that certain formulations comprising the compositions that modulate the activity of p11 are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic, nucleic acid and other degradation and/or substances that promote absorption such as, for example, surface active agents. Compositions may be complexed with polyethylene glycol (i.e., PEGylated), albumin or the like to help promote stability in the bloodstream.

The compositions that modulate the activity of p11 are administered to vertebrates in an amount effective to decrease the growth or metastasis of a tumor within the vertebrate. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein, i.e., the p11 activity assays. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

As discussed above, the serine protease plasmin is one of the key proteases associated with the invasive program of cancer cells. Plasmin degrades various glycoproteins present in basement membranes and other extracellular matrices ("ECM") and activates tumor-cell- and tumor-associated cell-derived pro-collagenases and pro-gelatinases, thus providing the cell with the necessary enzymatic machinery to breakdown and invade normal surrounding tissue structures (reviewed in references Tapiovaara et al., 1996; Rabbani and Mazar, 2001; DeClerck et al., 1997, Adv Exp Med Biol 425: 89-97; Pepper, M. S., 2001 Thromb Haemost 86:346-355).

The urokinase plasminogen activator ("uPA"), which is a plasminogen activator secreted by human cancer cells and other cell types, is partly responsible for the cell surface activation of plasminogen (Stephens et al., 1989). uPA is localized at the cell surface through binding to its receptor, uPAR. Similarly, plasminogen binds to a heterogeneous group of receptors at the cell surface. Although the interaction between the cell surface receptors for uPA and plasminogen play a key role in the spatial and temporal regulation of plasmin generation, it is believed that the plasminogen receptors are rate-limiting for this reaction (Namiranian et al., 1995). Despite this critical role that plasminogen receptors play in the regulation of plasmin production, little progress has been made in the identification of the plasminogen receptor(s) that are directly involved in plasmin production.

A major difficulty in studying the role of plasminogen receptors in plasmin production has been the cell by cell, clone by clone variation of expression of the genes for the plasminogen activators and plasminogen activator inhibitors within art standard cell lines. An important advancement toward the study of plasminogen receptors has been the instant invention of clonal cell lines to study plasmin regulation. Each clonal cell line was extensively characterized and only cell lines with comparable protein levels of plasminogen activators, tPA and uPA, uPAR, and plasminogen activator inhibitors, PAI-1 and PAI-2 were further characterized. Therefore, any changes in plasmin generation that are observed could be correlated with changes in the levels of p11 in the clonal cell lines. Preferred clonal cell lines are human cancer cells, preferably clonal human HT1080 fibrosarcoma and CCL-222 colorectal adenocarcinoma cell lines. Thus, in another embodiment, the invention is directed to clonal cell lines useful in the determination or identification of compositions that modulate p11 activity. The clonal cell lines may be derived from any organism, preferably vertebrates, and characterized according to the activity of p11, tPA, uPA, uPAR, PAI-1 and PAI-2, as herein described. The clonal cell lines may be employed in screens for compositions that modulate p11 activity by assessing changes in plasminogen binding or activation, plasmin activity or cell invasiveness associated with the clonal cell lines upon the administration of prospective compositions that modulate p11 activity. Prospective compositions that modulate p11 activity may come from libraries of compounds, agents, peptides, polynucleotides or the like that are made de novo or are otherwise available to the skilled artisan.

Therefore, in yet another embodiment, the present invention is drawn to methods of identifying compositions that modulate the activity of p11, comprising administering a prospective composition to a clonal cell line, then assessing a change in the activity of p11 or any cellular activity associated with p11 of the clonal cell line. As mentioned above, those changes in activities include changes in the expression of p11 at the cell surface or anywhere else in the cell, the development of tumor foci, tumor growth, plasmin production, plasminogen activation, cell invasion and proteolysis. Assays for these activities are described herein and are also well-known in the art.

The following examples are included in the specification to help illustrate the invention and are not meant to limit the scope of the invention.

EXAMPLE 1

Stimulation of $A_{61}$ Production $A_{61}$ is an internal fragment of plasminogen that encompasses the sequence $Lys^{78}$-$Lys^{468}$ (SEQ ID NO:1). The release of $A_{61}$ from plasmin is facilitated by the reduction of the $Cys^{462}$-$Cys^{541}$ disulfide bond of plasmin. Therefore, the release of $A_{61}$ generates a free sulfhydryl residue at $Cys^{462}$. Since plasminogen and plasmin contain only disulfides, $A_{61}$ can be discriminated from these proteins on the basis of its reactivity with free sulfhydryl-reactive reagents such as 3-(N-maleimidylpropionyl)biocytin (MPB). The reaction of free-sulfhydryl-containing proteins with MPB results in the biotinylation of the protein which allows easy detection with streptavadin-HRP.

As shown in FIG. 1A (lane 2), the incubation of u-PA with plasminogen resulted in the generation of plasmin. As expected, the plasmin generated by this reaction did not contain a free cysteinyl residue and therefore did not react with MPB (FIG. 1B, lane 2). However, the addition of AIIt to the u-PA-plasminogen reaction resulted in the appearance of $A_{61}$ (which displays a single major band and two minor bands of about $M_r$ 50 K on non-reduced SDS-PAGE) and disappearance of plasmin (FIG. 1A). Furthermore, the $A_{61}$ generated in these reactions reacted with MPB, confirming the presence of a free sulfhydryl in $A_{61}$ (FIG. 1B).

AIIt stimulated the dose- and time-dependent conversion of plasminogen to $A_{61}$ (FIG. 1A-D). The maximal conversion of plasminogen to $A_{61}$ occurred at approximately equimolar concentrations of AIIt and plasminogen (FIG. 1A,B). At equimolar concentrations the half-maximal conversion of plasminogen to $A_{61}$ occurred between 30-60 min (FIG. 1C,D). Since AIIt stimulated the generation of $A_{61}$ in the absence of sulfhydryl donors, the data reasonably suggest that AIIt promoted the cleavage of a plasmin disulfide, presumably the $Cys^{462}$-$Cys^{541}$ disulfide, resulting in the release of $A_{61}$ from plasmin and the generation of a free cysteine ($Cys^{462}$) in $A_{61}$.

Figures 2, 2A:
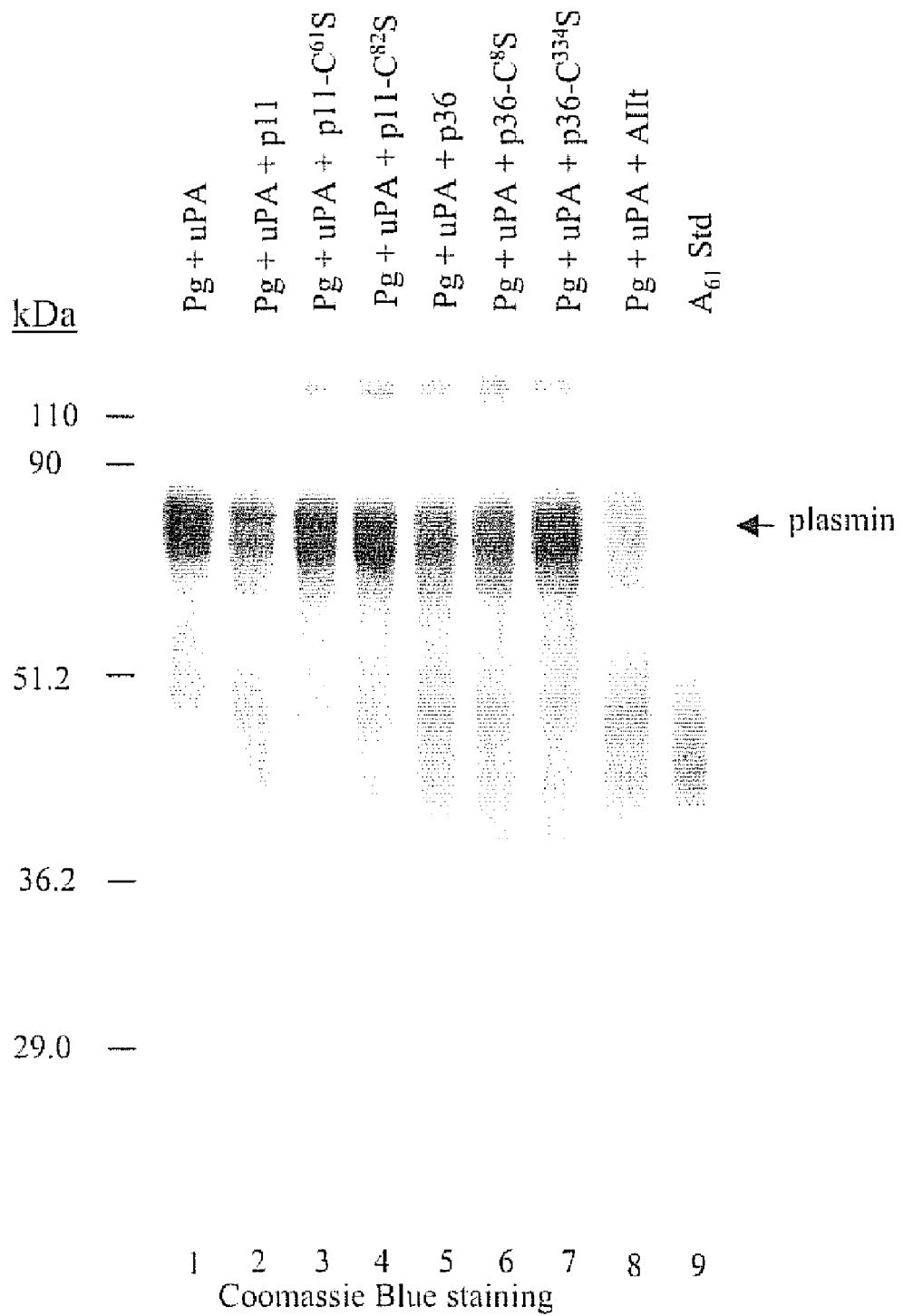
FIG. 2 Illustrates the role of p11 and p36 subunits in the plasmin reductase activity of AIIt. [Glu]-plasminogen (4 µM) was incubated with u-PA (0.075 µM) and various subunits of AIIt or AIIt (4 µM). The results are shown as Coomassie blue staining (A) and Western blot with streptavidin-HRP (B).

AIIt is composed of two copies of a p36 polypeptide subunit and two copies of a p11 polypeptide subunit. As shown in FIG. 2A,B the incubation of either the p36 or p11 subunit with u-PA and plasminogen stimulated the formation of $A_{61}$. However, AIIt appeared to be a more potent plasmin reductase than either subunit, suggesting that the interaction of the subunits potentiated the plasmin reductase activity of either subunit.

Theoretically, either the disulfides or cysteinyl residues of AIIt could participate in the reduction of plasmin. It is possible that upon plasminogen binding the disulfide of annexin II is reduced by the thiols of annexin II and the newly formed thiols participate in reduction of plasmin. Since the p11 subunit does not contain disulfides, it is reasonable to suspect that the thiols of this subunit were important for its plasmin reductase activity. p11 contains two cysteinyl residues: $Cys^{61}$ which plays a critical role in the binding of p36 and $Cys^{82}$ which is a free thiol (Johnsson and Weber, 1990, J Biol Chem 265:14464-14468). Two recombinant forms of this subunit were prepared, in which individual cysteinyl residues were mutated to serine. This conservative mutation results in the substitution of a thiol group for a hydroxyl group. As shown in FIG. 2B, substitution of either of these cysteine residues resulted in a loss of plasmin reductase activity of the p11 subunit. This suggests that both cysteinyl residues of p11 are required to sustain the plasmin reductase activity of the protein.

Human p36 contains two thiol-containing cysteines, $Cys^8$ and $Cys^{334}$. As shown in FIG. 2B, substitution of $Cys^{334}$, but not $Cys^8$, with serine blocked the plasmin reductase activity of p36. This result suggests that the $Cys^{334}$ thiol is critical for plasmin reductase activity of the p36 subunit.

Figure 3A:
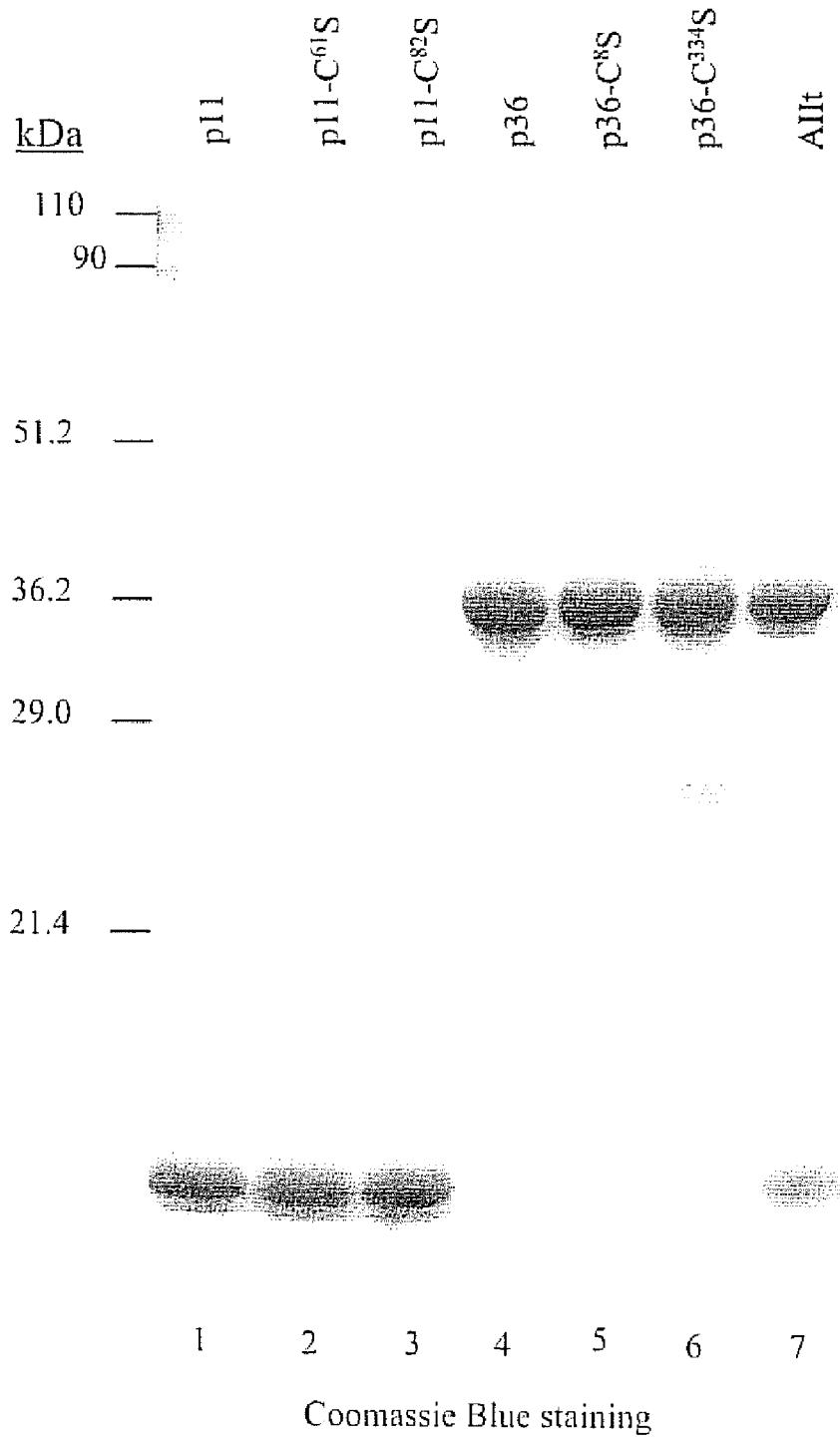
FIG. 3 illustrates the thiol reactivity of AIIt and its subunits. AIIt or its various subunits (2 µM) were incubated with MPB (100 µM), reduced glutathione and iodoacetamide, sequentially. The reaction mixtures were subjected to reduced SDS-PAGE followed by either Coomassie blue staining (A) or Western blot with streptavidin-HRP (B). (C) AIIt (18 µM) was incubated with iodoacetic acid (IAA, 10 mM) or MPB (200 µM). [Glu]-plasminogen (4 µM) was incubated with u-PA (0.075 µM) and the indicated AIIt (4 µM). The result shown is a Western blot with streptavidin-HRP.
Figure 3B:
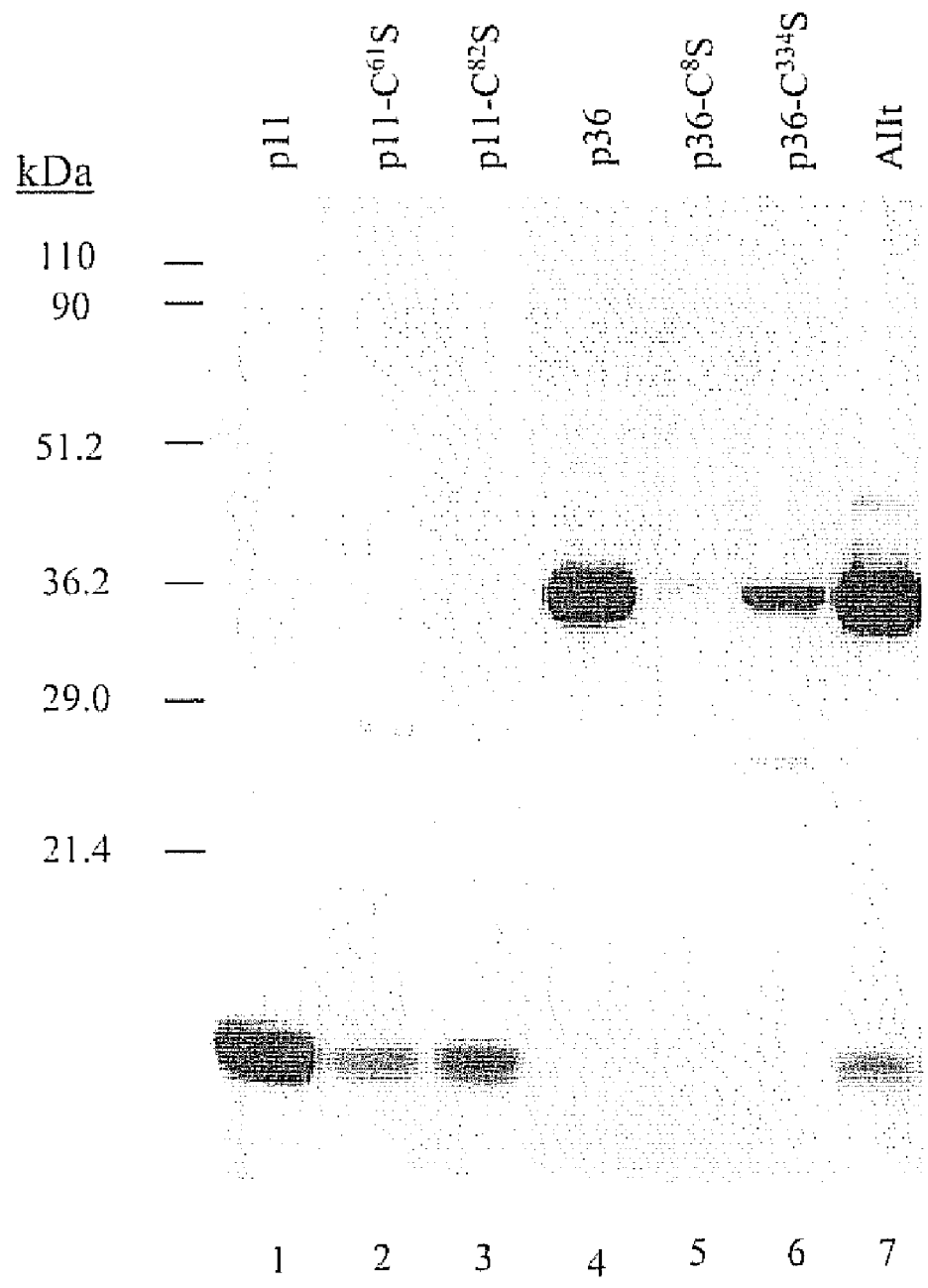

To identify the reactive thiols of AIIt and its subunits, AIIt, p36 and p11 were incubated with MPB and resolved with SDS-PAGE followed by Coomassie blue staining (FIG. 3A) or Western blot with streptavidin-HRP (FIG. 3B). As shown in FIG. 3B, the p11 subunit and both $Cys^{61}$Ser and $Cys^{82}$Ser p11 mutants were labeled with MPB. In contrast, although p36 and the $Cys^{334}$Ser p36 mutant were labeled with MPB, the $Cys^8$Ser mutant was not labeled. This suggests that the thiols of the isolated p11 are accessible to MPB whereas the $Cys^{334}$ of p36 is not accessible. Interestingly, both the p36 and p11 subunits within AIIt were labeled with MPB. However, preincubation of AIIt with iodoacetic acid or MPB resulted in only a small decrease in the plasmin reductase activity of AIIt (FIG. 3C). This suggests that the $Cys^{334}$ thiol of the p36 subunit of AIIt is inaccessible to the solvent.

Figure 4:
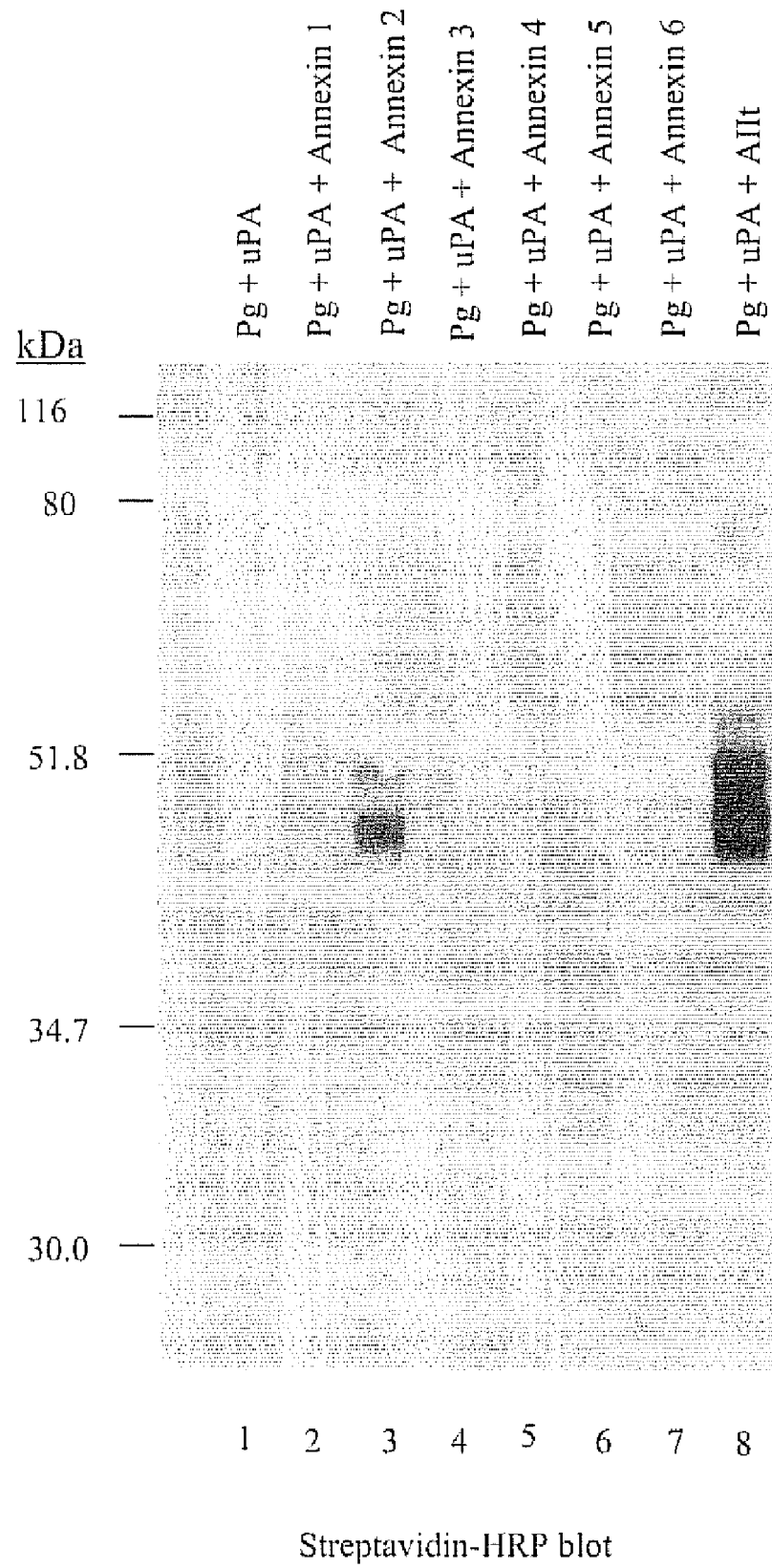
FIG. 4 illustrates the specificity of the plasmin reductase activity of AIIt. [Glu]-plasminogen (4 µM) was incubated with u-PA (0.075 μM) and the indicated annexin proteins (4 μM). The result shown is a Western blot with streptavidin-HRP.

Since the $Cys^{334}$ residue is highly conserved among many of the annexins, seven other annexins were examined for plasmin reductase activity. As shown in FIG. 4, only annexin II p36 subunit and AIIt possessed plasmin reductase activity. This result establishes that plasmin reductase activity is not a common feature of the annexins.

Figure 5:
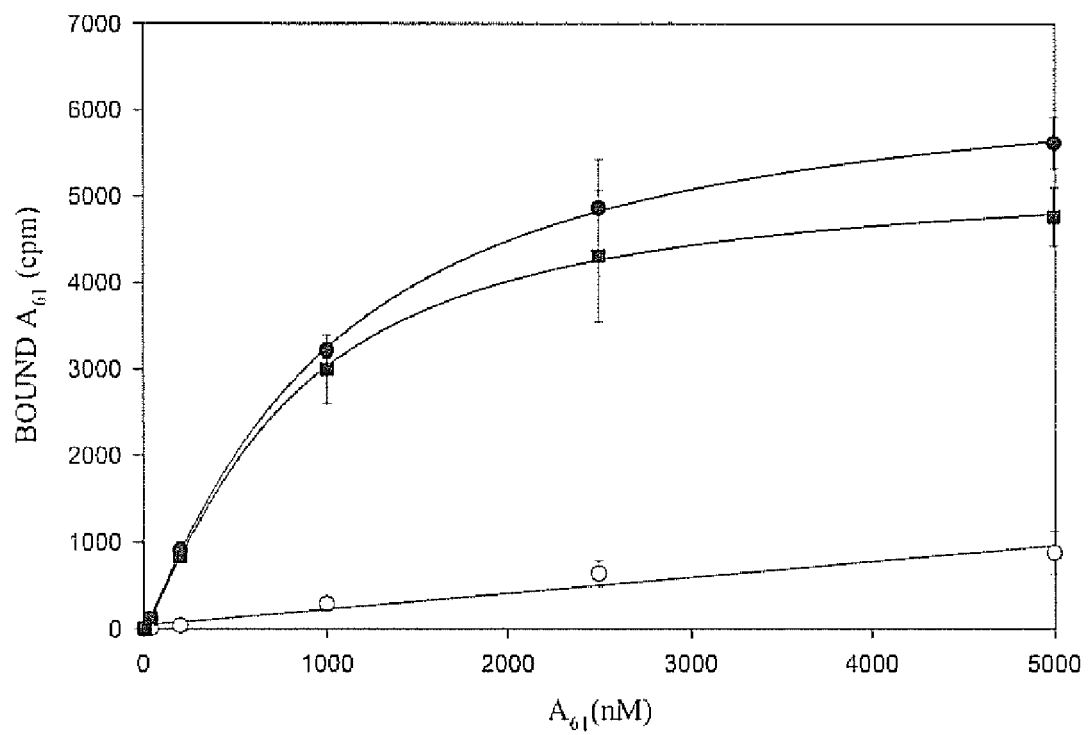
FIG. 5 illustrates the binding of $A_{61}$ to AIIt. The wells of Removawell™ strips were coated with phospholipid, blocked with bovine serum albumin, incubated with AIIt, and extensively washed. Various concentrations of iodinated $A_{61}$ were added into the AIIt-coated wells in the absence (filled circles) or presence of 30-fold molar excess of bovine serum albumin (filled triangles) or cold $A_{61}$ (open circles). Individual wells were detached and measured for radioactivity with γ-counter. The data shown (n=6) were the average of two separate experiments.

It is generally accepted in the art that AIIt binds both plasminogen and plasmin and is present at discrete regions of the extracellular surface (Kassam et al, 1998[a]; Kang et al., 1999; Mai et al. 2000). This suggested that AIIt could act as a scaffolding protein and focus the proteolytic activity of plasmin to the plasma membrane. It was unclear if the $A_{61}$ generated by cells could remain bound to AIIt at the cell surface or be immediately released into the media. However, as shown in FIG. 5, $A_{61}$ bound to AIIt with a $K_d$ of 1.0±0.05 μM (n=6). According to the observation made by the inventors that $A_{61}$ did not block the stimulation of tPA-catalyzed conversion of plasminogen to plasmin, one skilled in the art may reasonably expect that the binding sites on AIIt for $A_{61}$ are distinct from those for plasminogen or plasmin. This suggests that some of the $A_{61}$ produced by the AIIt's plasmin reductase reaction may remain bound to AIIt at the cell surface.

EXAMPLE 2

Stimulation of $A_{61}$ Production by Other Disulfide Reductases

Figure 6:
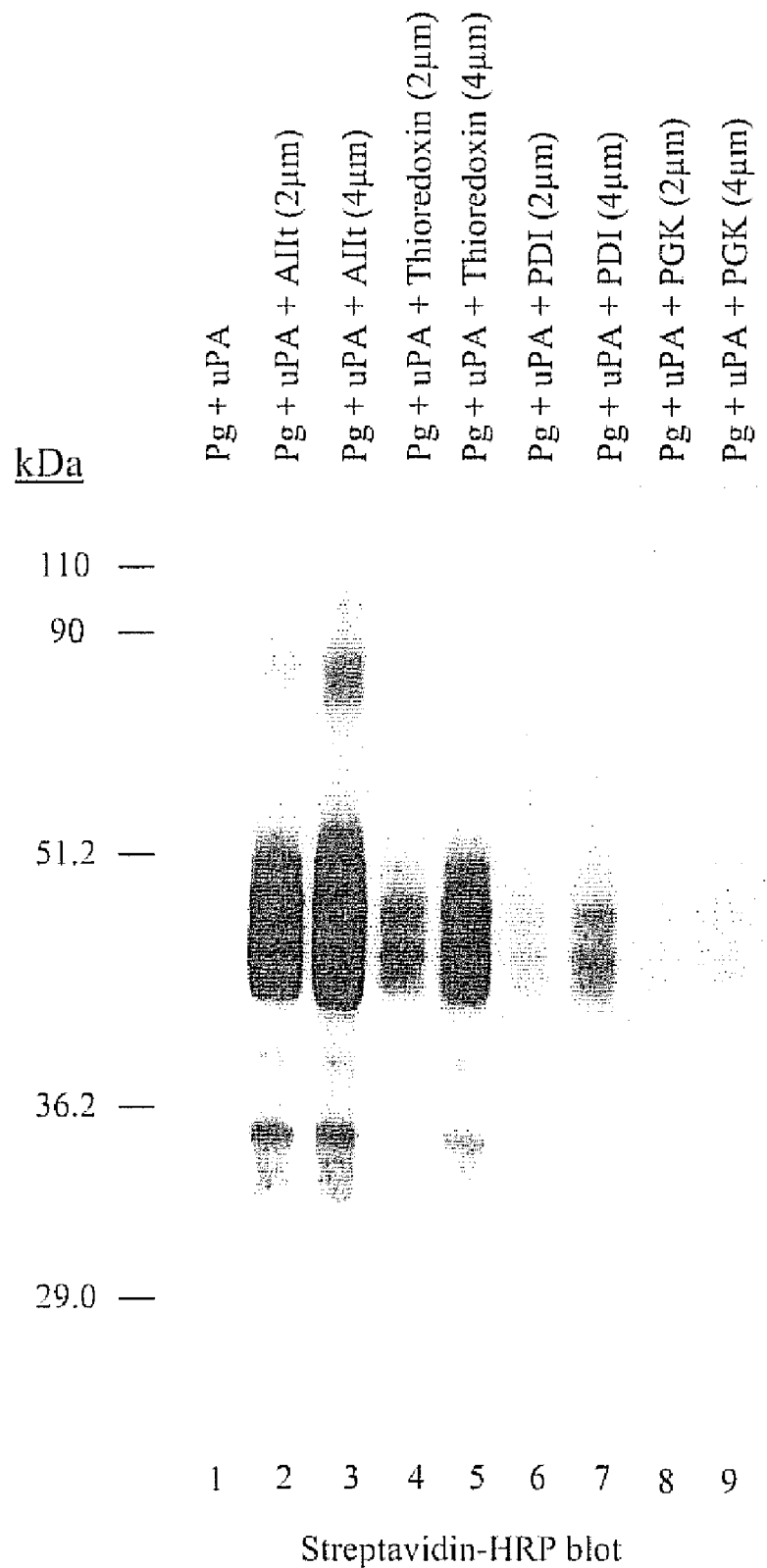
FIG. 6 illustrates a comparison of AIIt with other disulfide reductases. [Glu]-plasminogen (4 μM) was incubated with u-PA (0.075 μM) and the various proteins as indicated. The result shown is a Western blot with streptavidin-HRP.

Protein disulfide isomerase, thioredoxin and phosphoglycerate kinase are three protein disulfide reductases that are secreted by cultured cells (Lay et al., 2000, Nature 408:869-873; Rubartelli et al., 1992, J Biol Chem 267:24161-24164; Terada et al., 1995, J Biol Chem 270:20410-20416; Soderberg et al., 2000, Cancer Res 60:2281-2289). The three reductases have been shown to act as plasmin reductases (Stathakis et al., 1997, J Biol Chem 272:20641-20645; Lay et al., 2000). As shown in FIG. 6, under the assay conditions AIIt was a more potent plasmin reductase than the other reductases in vitro.

Thioredoxin and protein disulfide isomerase share a common sequence, Trp-Cys-Gly-Pro-Cys-Lys (SEQ ID NO:4), which participates in the cleavage, formation and reshuffling of disulfide bonds. This sequence is not present in phosphoglycerate kinase or AIIt, suggesting that these reductases have distinct catalytic mechanisms. Typically, the disulfide reductase activity of thioredoxin or protein disulfide isomerase is measured by determination of their rates of reduction of insulin disulfide (Heuck and Wolosiuk, 1997, J Biochem Biophys Methods 34:213-225; Heuck and Wolosiuk, 1997, Anal Biochem 248:94-101). Interestingly, although protein disulfide isomerase and thioredoxin exhibit potent insulin reductase activity, AIIt failed to exhibit insulin reductase activity. This further confirms that the catalytic mechanism of AIIt is distinct from that of some other protein reductases.

EXAMPLE 3

Down-regulation of alit blocks $A_{61}$ generation

Figures 7, 7A:
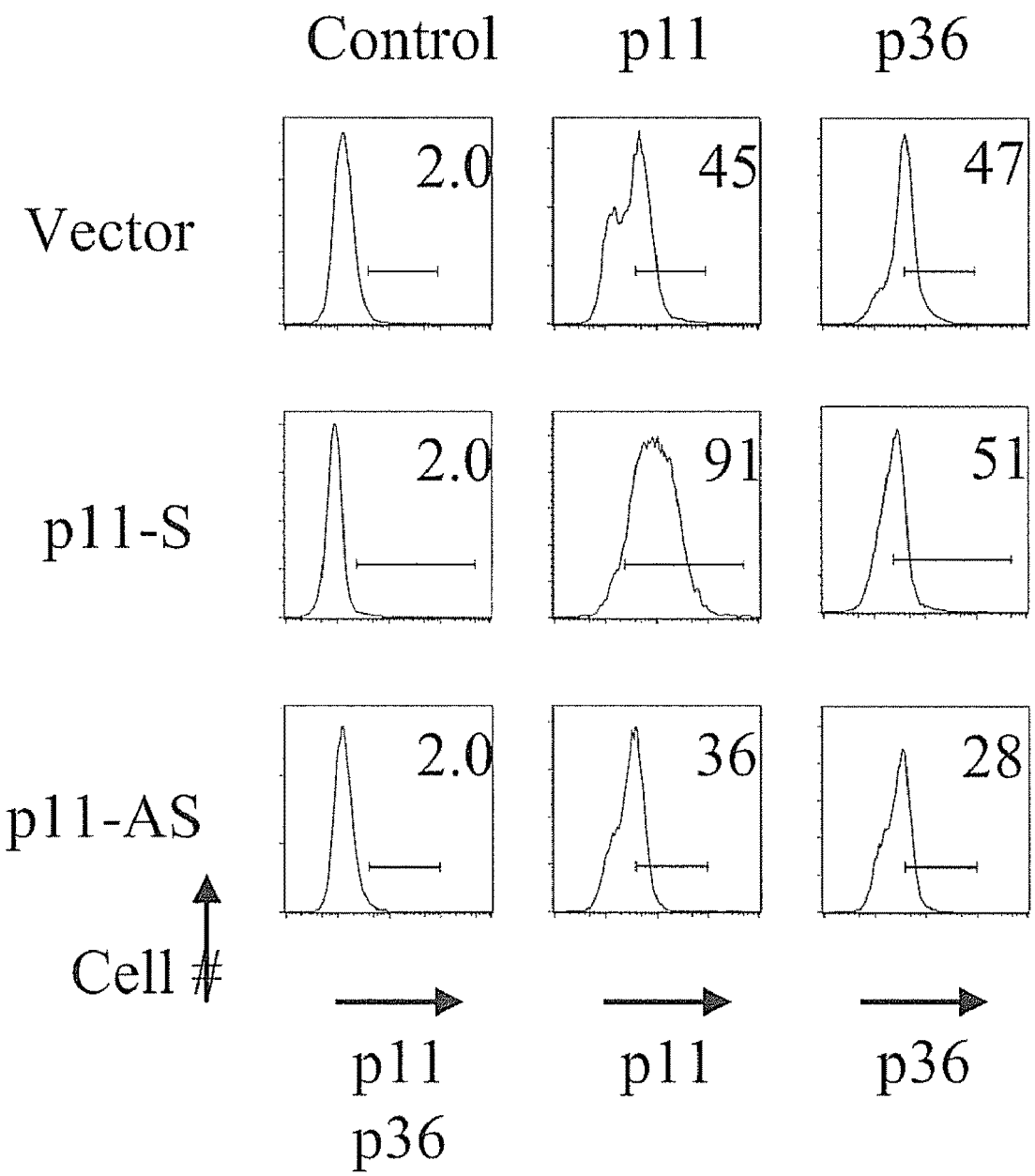
FIG. 7 illustrates that the down-regulation of AIIt blocks $A_{61}$ generation by HT1080 cells. (A) Flow cytometric analysis of transduced HT 1080 cells. (B,C) Comparison of the generation of $A_{61}$ by transduced HT 1080 cells. Transduced HT 1080 cells were incubated with DMEM containing 2 μM [Glu]-plasminogen (B) or plasmin (C). After the indicated time of incubation, the medium was analyzed by reduced SDS-PAGE (B) or non-reduced SDS-PAGE (C) followed by Western blot with monoclonal anti-human plasminogen kringle 1-3 antibody.
Figure 7B:
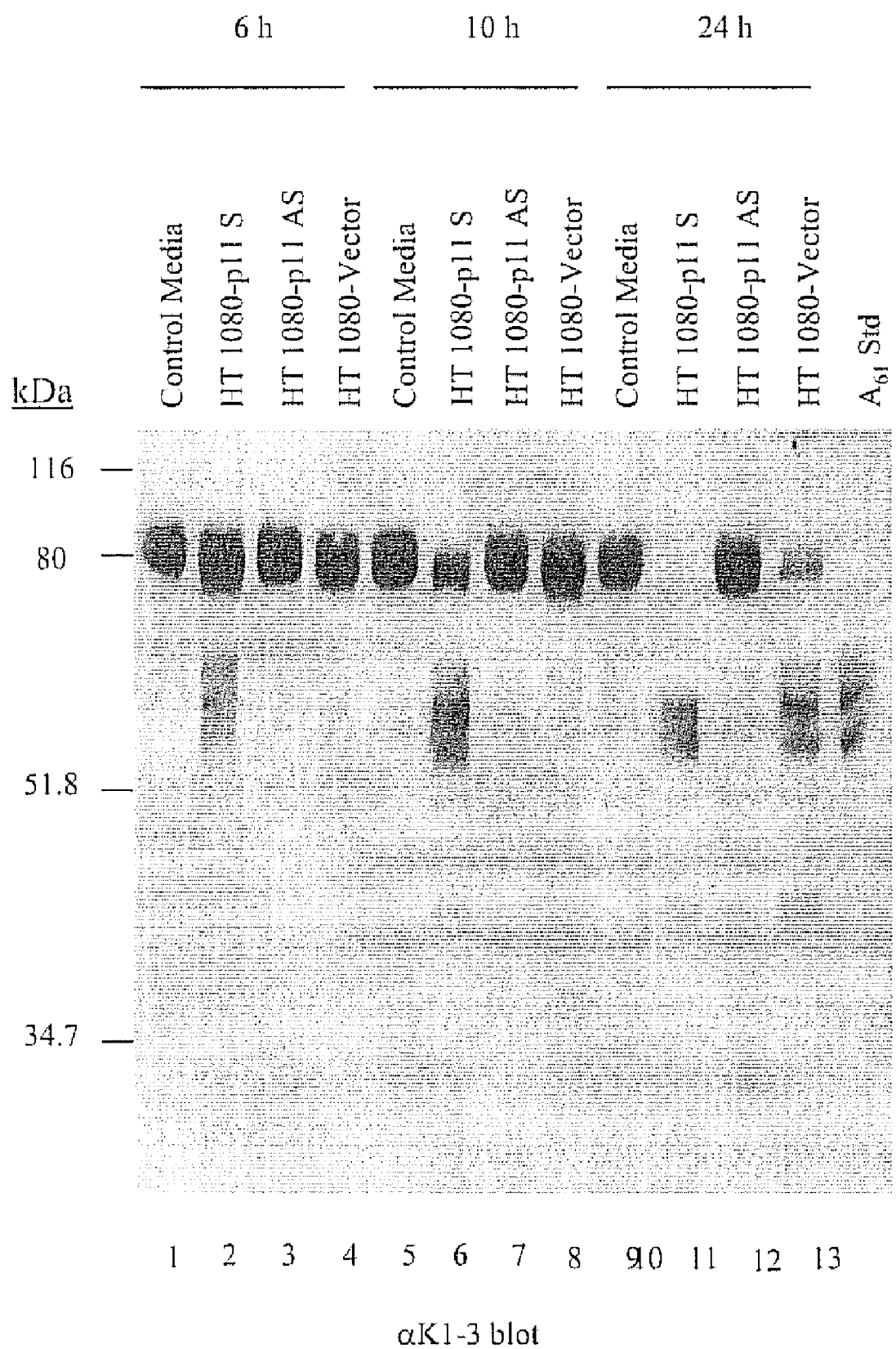

HT1080 fibrosarcoma cells were stably transfected (transduced) with a pLin retroviral vector encoding a p11 gene in the sense (pLin-p11S) or antisense (pLin-p11AS) orientation, or an empty pLin vector (pLin-V). The pLin-p11AS transduced cells showed a decrease in both p11 and p36 subunits on the cell surface whereas pLin-p11S transduced cells showed an increase in both p11 and p36 subunits (FIG. 7A). As shown in FIG. 7B, incubation of the pLin-p11S transduced cells with plasminogen resulted in enhanced $A_{61}$ formation compared to the pLin-V control cells. In contrast, the pLin-p11AS transduced cells failed to produce $A_{61}$. Additionally, HeLa cells transfected with a p11 antisense expressing vector also failed to convert plasminogen to $A_{61}$.

Figure 7C:
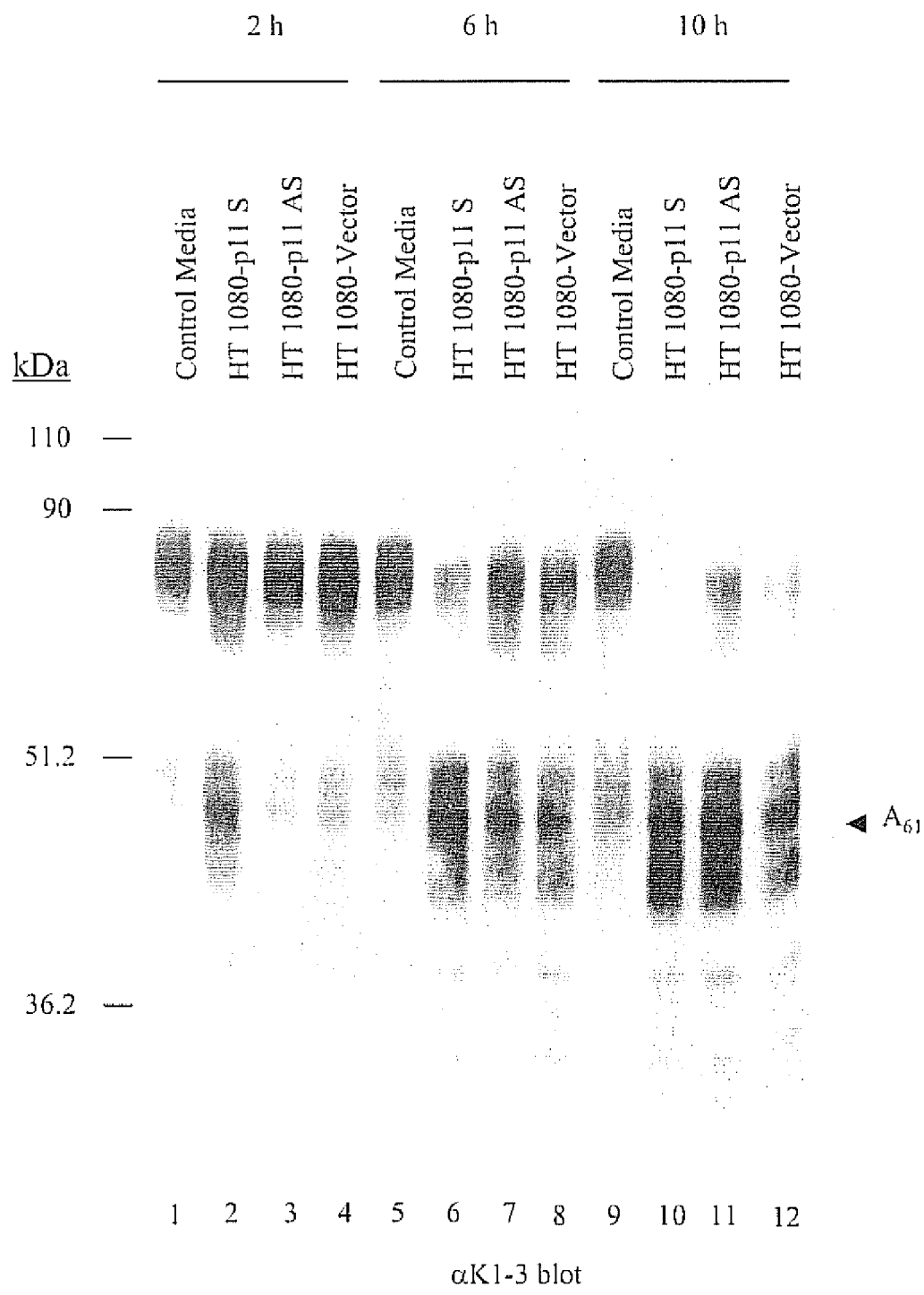

The data in FIG. 7B establishes a role for AIIt in $A_{61}$ formation in HT 1080 fibrosarcoma cells. However, it is unclear if plasmin could be directly reduced or if plasmin autoproteolysis preceded plasmin reduction. As shown in FIG. 7C, the incubation of plasmin with the pLin-p11S cells also resulted in the accelerated disappearance of plasmin and concomitant enhanced appearance of $A_{61}$ compared with pLin-p11V cells. In contrast, the pLin-p11AS cells showed reduced plasmin loss and concomitant $A_{61}$ formation compared to the pLin-p11V cells. In another series of experiments, plasmin was inactivated by prior treatment of the serine protease inhibitor, DIFP and then incubated with the HT1080 cells. However, $A_{61}$ production by the cells was not observed. Furthermore, the catalytically inactive plasmin that was incubated with the cells was not reduced since it did not react with MPB. This result may be interpreted by the skilled artisan to mean that plasmin autoproteolysis is required before plasmin reduction can occur. Collectively, the experimental observations herein disclosed suggest that the mechanism of $A_{61}$ formation involves the u-PA-dependent conversion of plasminogen to plasmin followed by plasmin autoproteolysis and reduction of cleaved plasmin (FIG. 8).

EXAMPLE 4

Materials and Procedures Employed in Preceding Examples 1-3

Two-chain urokinase-type plasminogen activator (u-PA) was a generous gift from Dr. H. Stack (Abbott Laboratories). [Glu]-plasminogen and plasmin were purchased from American Diagnostica. Antiangiogenic plasminogen fragment ($A_{61}$) was purified as outlined in copending patent application PCT/US01/44515. Annexin II heterotetramer (AIIt) and other annexins were purified from bovine lung as described in Khanna et al., 1990, Biochemistry 29:4852-4862. Monoclonal anti-human plasminogen kringle 1-3 antibody was purchased from Enzyme Research Laboratories Inc. Monoclonal anti-annexin II and anti-annexin II light chain antibodies were purchased from Transduction Laboratories. Anti-mouse horseradish peroxidase-conjugated secondary antibody was purchased from Santa Cruz Biotechnology. Horseradish peroxidase-conjugated streptavidin and protein disulfide isomerase were purchased from Calbiochem. Anti-mouse R-phycoerythrin-conjugated secondary antibody was purchased from Caltag Laboratories Inc. $N^\alpha$-(3-maleimidyl-propionyl)biocytin (MPB) was purchased from Molecular Probes. Reduced glutathione, iodoacetamide, iodoacetic acid, diisopropylfluorophosphate (DIFP), and thioredoxin were purchased from Sigma. L-lysine-Sepharose was purchased from Amersham Pharmacia Biotech. Iodobeads were purchased from Pierce. Phosphoglycerate kinase (PGK) was a generous gift from Dr. P. J. Hogg (Center for Thrombosis and Vascular Research, University of New South Wales, Sydney, Australia). Stably transfected HeLa cells expressing p11 antisense or sense mRNA were a generous gift from Dr. J. H. Shelhamer (Critical Care Medicine Department, National Institutes of Health, USA). HT1080 fibrosarcoma cells were obtained from American Type Culture Collection. Dulbecco's modified eagle medium (DMEM) was purchased from Life Technologies.

Mutagenesis of Annexin II and p11—Bacterial expression vectors containing the wild-type sequence for annexin II (pAED4.91-annexin II) and p11 (pAED4.91-p11) were mutated using the QuikChange™ Site-Directed Mutagenesis Kit (Stratagene). Briefly, mutagenic primers were synthesized that introduced Cys→Ser mutations at positions 8 and 334 of annexin II, as well as positions 61 and 82 of p11. All of the mutations introduced were verified by DNA sequence analysis. These various plasmids were then transformed into *E. coli* BL21 (DE3) and grown as previously described (Filipenko and Waisman, 2001, J Biol Chem 276:5310-5315).

Purification of Wild-type and Mutant Annexin II—After 4 hours of induction with IPTG, bacteria were collected by low speed centrifugation. The cells were subsequently sonicated in lysis buffer (10 mM imidazole, pH 7.5, 150 mM NaCl, 2 mM EGTA, 1 mM DTT+protease inhibitors) and centrifuged at 100,000×g for 1 hour at 4° C. Both mutant annexin II proteins were purified in the same manner as wild-type annexin II via hydroxyapatite, heparin-Sepharose affinity and gel permeation chromatography as reported previously (Filipenko and Waisman, 2001, J Biol Chem 276:5310-5315). The elution profiles of the recombinant wild-type and mutant annexin II on hydroxyapatite, heparin affinity and gel permeation chromatography were indistinguishable. In addition, the circular dichroism spectra of each of the proteins were very similar, indicating little secondary structure perturbation.

Purification of Wild-type and Mutant p11—After 4 hours of induction with IPTG, bacteria were collected by low speed centrifugation. The cells were subsequently sonicated in lysis buffer (100 mM Tris-HCl, pH 7.5, 200 mM NaCl, 10 mM $MgCl_2$, 2 mM DTT+protease inhibitors) and centrifuged at 100,000×g for 1 h at 4° C. Both p11 mutants were purified in the same manner as wild-type p11 (Ayala-Sanmartin et al., 2000, Biochemistry 39:15179-15189). Briefly, the cell lysis supernatant was precipitated with 50% $(NH_4)_2SO_4$, and the supernatant was applied to a Butyl-Sepharose column equilibrated in lysis buffer containing 50% $(NH_4)_2SO_4$. The p11 was eluted with a linear gradient of $(NH_4)_2SO_4$ from 50% to 0%, and peak fractions containing p11 were pooled and dialyzed against 10 mM imidazole, pH 7.4, 1 mM EGTA, 0.5 mM DTT, and 0.1 mM EDTA. The dialyzed fractions were subsequently applied to a DEAE-Sepharose column equilibrated in the same buffer. The p11 was eluted with a linear NaCl gradient, concentrated to 4 mL, and applied to a Sephacryl S-100 column equilibrated in 40 mM Tris-HCl, pH 7.4, 0.1 mM EGTA, and 0.1 mM DTT. A single protein peak was recovered at the expected molecular weight based on gel filtration standards.

Plasmid Construction and Transfection of HT1080 Cells—Sense and antisense p11 expression vector were produced by cloning the full-length human p11 cDNA into the pLin retroviral vector in the sense (pLin-p11S) or antisense orientation (pLin-p11AS) as reported (Ghahary et al., 1998, J Invest Dermatol 110:800-805). Control cells transduced with the vector alone (pLin-V) were also established. The pLin vector carries the Moloney murine leukemia virus 5' LTR enhancer/promoter region to promote strong, constitutive expression of the cloned p11 inserts and neomycin phosphotransferase gene in mammalian cells. The pLin constructs were propagated in a PA317 retroviral packaging cell line. Packaging cells were selected in 300 μg/ml neomycin and conditioned media that contained high titers of the virus were used to transduce the HT1080 fibrosarcoma cells. After viral transduction the neomycin resistant HT1080 fibrosarcoma cells were cloned and permanent cell lines established (Choi, K-S et al., in press at FASB J.).

Dialysis of Candidate Plasmin Reductase Proteins—After purification or reconstitution, AIIt, p11, p36 (annexin II), other annexins, thioredoxin, protein disulfide isomerase, and phosphoglycerate kinase were dialyzed against 20 mM Tris (pH 7.5) and 140 mM NaCl under argon gas to prevent possible oxidation.

Plasmin Reductase Assay—[Glu]—plasminogen (4 μM) was incubated with 0.075 μM u-PA and a candidate plasmin reductase protein (4 μM, unless described) in a buffer containing 20 mM Tris (pH 7.5) and 140 mM NaCl at 37° C. for 2 h. A portion of reaction mixture was diluted with SDS-PAGE sample buffer and subjected to non-reduced SDS-PAGE followed by Coomassie blue staining. To label any free thiol groups of produced protein(s), the reaction mixture was incubated with 100 μM MPB at room temperature for 30 min. The reaction mixture was then treated with 200 μM reduced glutathione at room temperature for 10 min to quench the unreacted MPB. The unreacted glutathione and other free thiols in the reaction mixture were blocked with 400 μM of iodoacetamide at room temperature for 10 min. Then the reaction mixture was incubated with L-lysine-Sepharose at room temperature for 30 min to purify the kringle-containing, plasminogen-derived proteins. The matrix was extensively washed with PBS and the bound proteins were eluted by boiling the resin with SDS-PAGE sample buffer. Each sample was subjected to non-reduced SDS-PAGE followed by Western blot with horseradish peroxidase-conjugated streptavidin (streptavidin-HRP) as indicated below.

Detection of free thiols in AIIt—2 μM AIIt, p11, or p36 was incubated with 100 μM MPB in a buffer containing 20 mM Tris (pH 7.5) and 140 mM NaCl at room temperature for 30 min. After incubation, 200 μM reduced glutathione and 400 μM iodoacetamide were added sequentially, and the reaction mixture was subjected to reduced SDS-PAGE followed by either Coomassie blue staining or Western blot with streptavidin-HRP as indicated below.

Cell-Mediated Generation of $A_{61}$—Transduced HT1080 cells were maintained in DMEM supplemented with 10% heat-inactivated fetal bovine serum, 2 mM L-glutamine, 10 units/ml penicillin G, 10 μM streptomycin sulfate, and 300 μg/ml neomycin. Approximately $1 \times 10^5$ cells were added to each well of 24-well tissue culture plates and incubated at 37° C. for 24 h. The cell monolayers were then washed three times with DMEM and 2 M [Glu]-plasminogen, plasmin, or diisopropylfluorophosphate (DIFP)-treated plasmin in DMEM was added to each well. The conditioned medium was removed at indicated times, diluted with SDS-PAGE sample buffer with or without β-mercaptoethanol and subjected to SDS-PAGE followed by Western blot with monoclonal anti-human plasminogen kringle 1-3 antibody (anti-K1-3) as indicated below.

Electrophoresis and Western Blot—Samples were diluted with SDS-PAGE sample buffer and subjected to SDS-PAGE and electrophoretically transferred to nitrocellulose membrane (0.45 μM pore size) at 4° C. for 1 h. The membrane was blocked in TPBS (phosphate buffered saline containing 0.1% Tween-20) with 5% skim milk at room temperature for 1 h and incubated at 4° C. overnight with a 0.4 μg/ml monoclonal anti-human plasminogen kringle 1-3 antibody in TPBS with 5% skim milk. The blot was extensively washed with TPBS at room temperature and then incubated at room temperature for 1 h with a 0.16 μg/ml horseradish peroxidase-conjugated goat anti-mouse secondary antibody in TPBS with 5% skim milk. In the case of MPB-reacted protein samples, the membrane was blocked and incubated at room temperature for 1 h with a 0.1 μg/ml streptavidin-HRP in TPBS with 5% skim milk. The membrane was extensively washed with TPBS and visualized by enhanced chemiluminescence (Pierce).

Binding of $A_{61}$ to AIIt—The purified $A_{61}$ was iodinated according to manufacturer's procedures. Iodinated $A_{61}$ retained biological activity as determined by the endothelial cell proliferation assay (Kassam et al., 2001). 96-well Immulon-1 Removawell strips (Dynex Technologies) were coated with phospholipid mixture containing 3:1 ratio of phosphatidylserine to phosphatidylcholine and air-dried. The coated strips were blocked with 1% fatty acid-free bovine serum albumin (BSA) in a buffer containing 20 mM Hepes (pH 7.4), 140 mM NaCl, and 2 mM $CaCl_2$ (buffer A) at room temperature for 2 h. The strips were washed with buffer A and incubated with 1 μM AIIt in buffer A at room temperature for 4 h. The strips were then washed and incubated with 0.008-5 μM iodinated $A_{61}$ with or without 30-fold molar excess of cold $A_{61}$ or BSA at 4° C. After overnight incubation, the strips were washed five times with PBS, and individual wells were detached and measured for radioactivity with a γ-counter. The data shown (n=6) are the average of two separate experiments.

Flow Cytometric Analysis of Transduced HT 1080 Cells—Transduced HT 1080 cells were harvested and $1\times10^6$ cells in PBS were divided into each tube. The cells were fixed with 4% paraformaldehyde in PBS at room temperature for 20 min and washed twice with PBS. The cells were then incubated with 1 µg of monoclonal anti-annexin II or anti-annexin II light chain antibody at room temperature for 30 min. For the control staining, 1 µg of mouse Ig G was used. The cells were washed and incubated with 2 µg/ml anti-mouse R-phycoerythrin-conjugated secondary antibody at room temperature for 30 min. The cells were washed and subjected to flow cytometric analysis using FACScan™ (Beckton Dickinson) and analyzed by the FlowJo™ program. The data shown are a representative of three separate experiments.

EXAMPLE 5

Manipulation of the Cell Surface Expression Level of p11

To assess the role of p11 in cellular plasmin generation, retroviral-mediated gene transfer was employed to stably transduce a model cancer cell, the HT1080 fibrosarcoma cell line, with a pLin retroviral vector. This vector contains genes coding for p11 and for resistance to the antibiotic G418. The p11 gene was inserted in the plasmid in the sense (pLin-sp11) or antisense (pLin-ap11) orientation. Stable G418-resistant cells were selected and cloned. Clones expressing altered levels of p11 were selected and propagated as stable clonal cell lines. These permanent clonal cell lines were designated as AS5 (pLin-ap11 cell line), and S7 (pLin-sp11 cell line). The control cells, designated Vec-1, were transduced with the empty pLin vector, propagated without cloning and used in the subsequent experiments.

Figure 9:
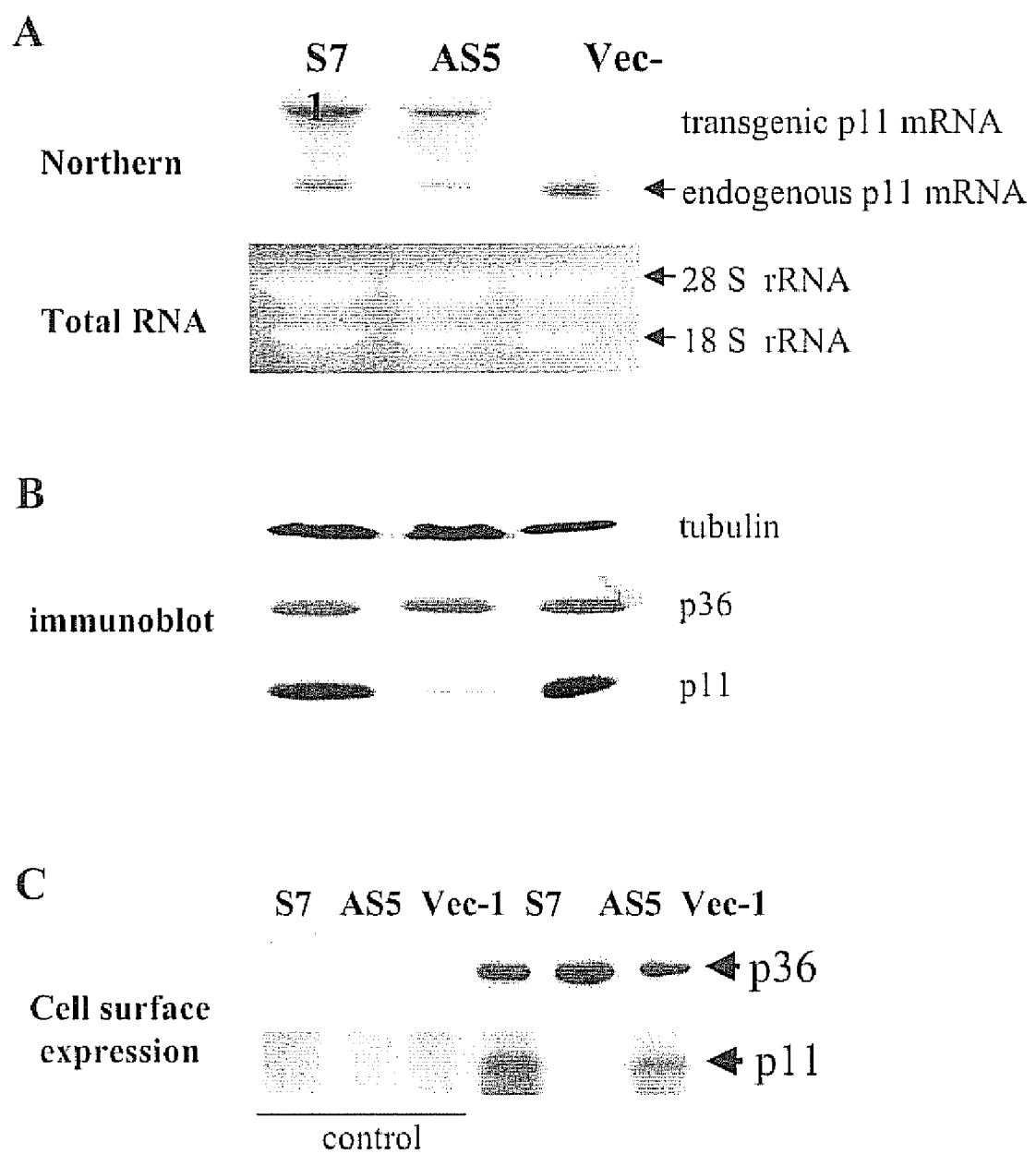
FIG. 9. Characterization of p11-sense and p11-antisense cell lines. A) Total RNA was isolated from the S7, AS5, and vec-1 cells and analyzed by Northern blot hybridization with a p11 probe. Total RNA is shown by ethidium bromide staining of the gel. B) Protein expression of p11 was determined by immunoblot analysis. Expression of α-tubulin was also determined as a control. C) The cells were surface biotinylated and the total cell extract was subjected to streptavidin-agarose pull down assay. The control consisted of empty agarose beads. The pull down complex was analyzed by immunoblot analysis to detect annexin II (p36). To detect p11, the cell lysate was immunoprecipitated with anti-p11 mAb and cell surface p11 was detected with a streptavidin probe. HT1080 fibrosarcoma cells were also transfected with pLin-sp11, pLin-ap11, and pLin by using LIPOFECTAMINE 2000 Reagent (Gibco BRL) and stable transfectants were cloned and clonal cell lines propagated. D) Expression of annexin II and p11 in the p11-sense clonal cell lines (S8, S9, S10), p11-antisense clonal cell lines (AS6, AS7) and control vector-transfected cells (vec-2) was examined by Western blotting. E) Western blot analysis of plasminogen activators (tPA, uPA), uPAR and plasminogen activator inhibitors (PAI-1, PAI-2) in the conditioned media from cell lines.
Figure 9:
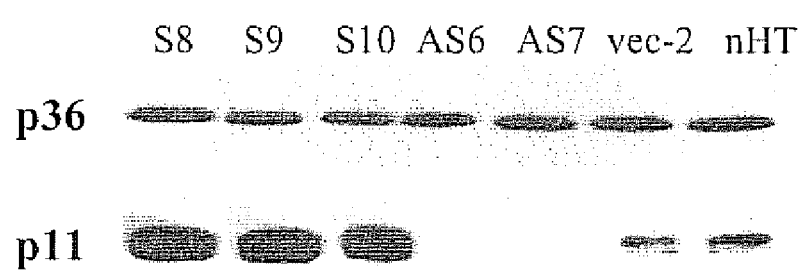
Figure 9:
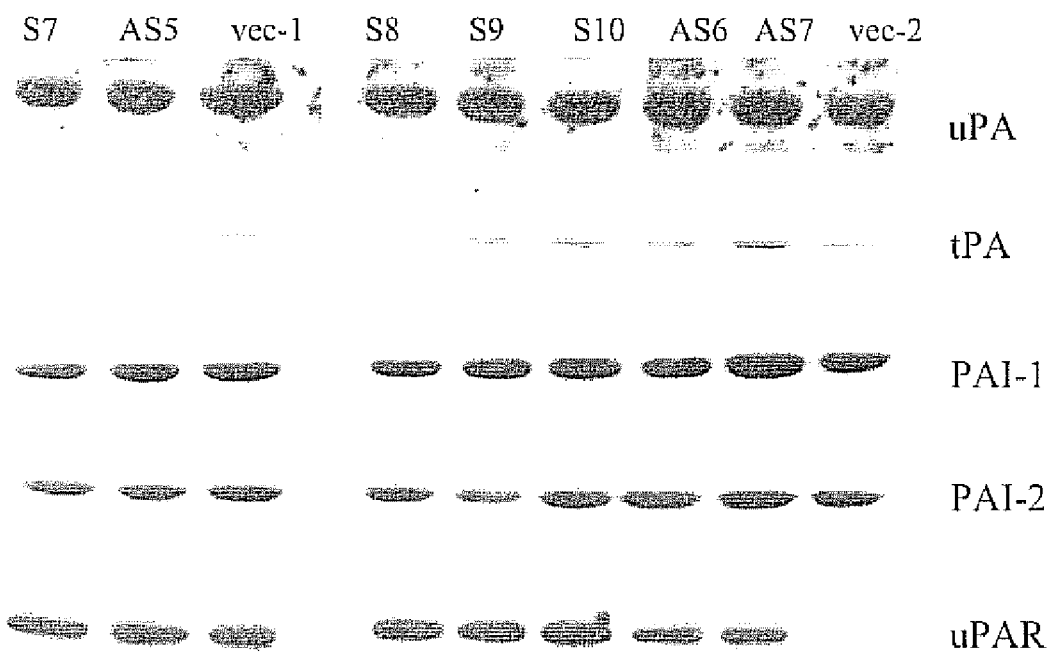

Stable integration of the G418-p11 transgene in the cellular genome resulted in expression of the transgene mRNA by the AS5 and S7 cell lines (FIG. 9A). This resulted in an increase in total cellular levels of p11 in the S7 cells and a decrease in total cellular levels of p11 in the AS5 cell line (FIG. 9B). The p11 protein level of the S7 clone was slightly higher than the Vec-1 clone. As a control, the protein level of tubulin was similar in the three cell lines (FIG. 9B). Furthermore, the protein level of annexin II (p36), the primary binding partner of p11 was similar across the three cell lines.

To confirm that the cell lines had altered extracellular levels of p11, cell surface proteins were labeled with a biotin-conjugated protein-labeling reagent, Sulfo-NHS-Biotin, collected the biotin-labeled proteins by avidin affinity chromatography and immunoprecipitated p11 from the crude extract of biotinylated surface proteins. The S7 clone contained higher extracellular levels of p11 than the Vec-1 cells, whereas p11 was virtually undetectable on the surface of the AS5 cell line (FIG. 9C). In contrast, the extracellular levels of annexin II remained unchanged in the cell lines.

Viral transduction of cells has been reported to inappropriately activate the transcription of cellular genes unrelated to the transgene (Tibbles et al., 2002, J Virol 76:1559-1568). Therefore, Lipofectamine™ reagent was used to transfect the HT1080 cells with the pLin-ap11, pLin-sp11 and the empty pLin vector. The G 418-resistant cells were cloned and stable cell lines were established. Two p11-antisense clonal cell lines (AS6, AS7), three p11-sense clonal cell lines (S8, S9, S10) and vector control cells (Vec-2) were successfully established by this procedure. Western blot analysis demonstrated that compared to the Vec-2 cells or the non-transfected cells, the pLin-sp11 cell lines had increased levels of p11 (FIG. 9D). Furthermore, p11 levels were not detected in the p11-antisense cell lines. Total cellular levels of annexin II remained essentially constant in all cell lines.

The clonal selection of cancer cells, such as HT1080 cells can result in the isolation of different clones with considerable variation of expression of proteins involved in the plasminogen activation cascade (Laug et al., 1992, Int J Cancer). Although selection of the cell lines used herein was initially based on their p11 levels, it was possible that cells with altered levels of plasminogen activators or plasminogen activator inhibitors were inadvertently selected. However, as shown in FIG. 9E, Western blot analysis of the cell lines established that these cell lines (which are "clonal cell lines" as defined herein) had comparable protein levels of PAI-1, PAI-2, tPA, uPA and uPAR.

Figure 10:
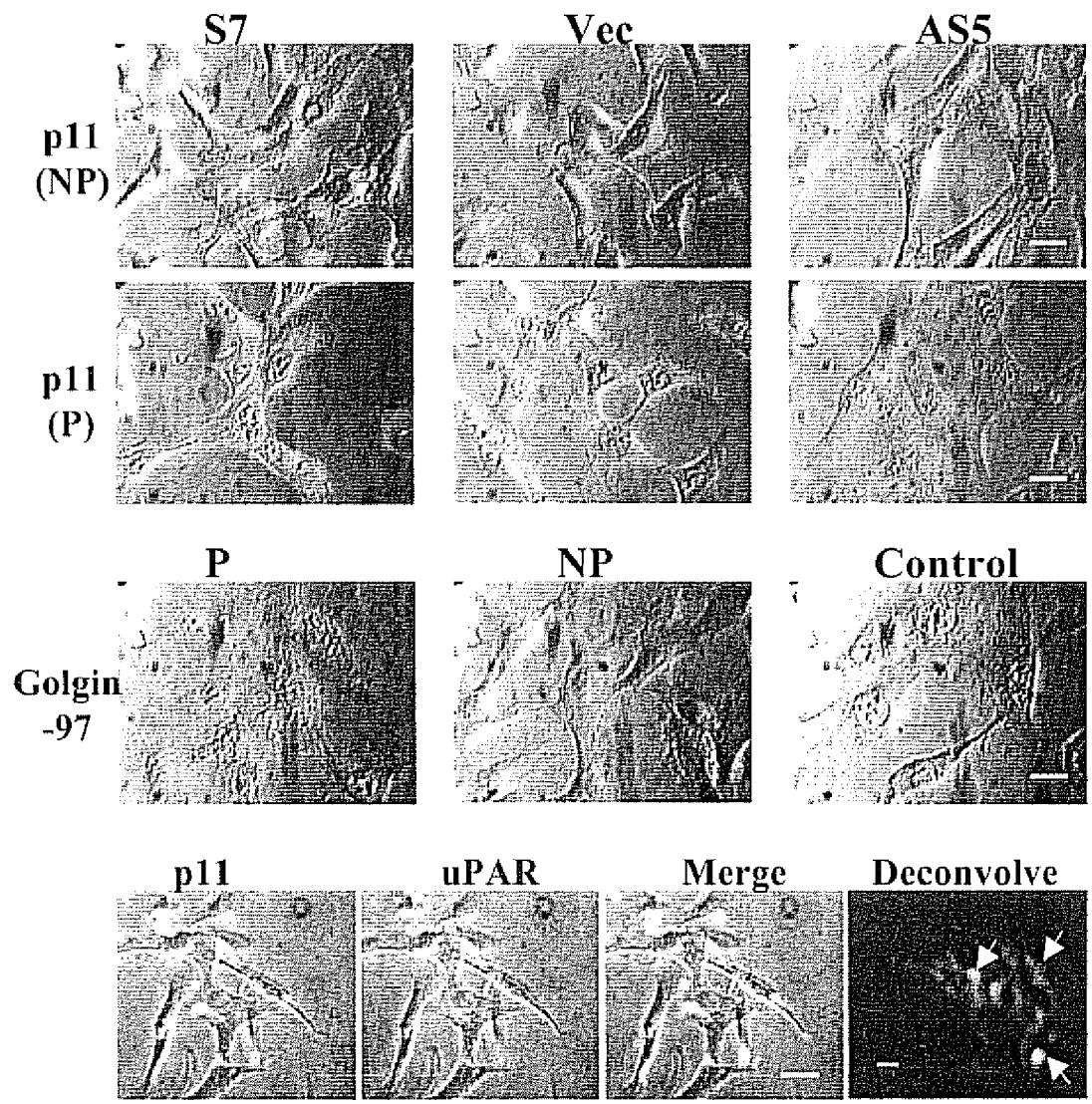
FIG. 10. The extracellular and intracellular expression of p11 in S7, AS5, and Vec-1 HT1080 cells. Upper panels, permeabilized (P) or non-permeabilized (NP)S7, AS5, and Vec-1 HT1080 cells were fixed, stained with anti-p11 antibody (Transduction Laboratories, San Jose, Calif.) and cy3 secondary antibody and examined under a fluorescence microscope. Bar, 10 microns. Middle panel, cells were stained with the golgi marker, golgin-97 which served as a permeabilization control. Lower panel, the extracellular expression of p11 and uPAR is compared. In the lower left panel a patch of p11/uPAR immunofluorescence consisting of a 0.3 micron thick optical section, was analysed by confocal microscopy. Bar, 0.5 microns. The arrows indicate regions of close proximity.

An analysis of the extracellular levels and distribution of p11 by immunofluorescence microscopy of the HT1080 cell lines was performed. As exemplified by the Vec-1 cells, extracellular p11 was observed in discrete patch-like structures on the cell surface whereas a typical cytoplasmic staining pattern was observed for intracellular p11. A similar staining pattern has been observed for the cell surface p11 of breast carcinoma, glioma and HUVEC cells (Kang et al., 1992; Mai et al., 2000, Biochim Biophys Acta 1477:215-230). The p11-antisense cell lines exhibited a loss of p11 from the cell surface. For example, p11 was barely detectable on the extracellular surface of the AS5 cell line (FIG. 10). In contrast the p11-sense cell lines showed significant increase in extracellular p11. For example, the S7 clone showed more intense immunoreactivity than the Vec-1 cells. Since only the permeabilized cells stained for the golgi protein, golgin-97, the extracellular localization of p11 could not be attributed to the inadvertent permeabilization of the cells during the staining process. The HT1080 cells were also stained for uPAR. As shown in FIG. 10, p11 and uPAR colocalized on the surface of these cells. Collectively, these data confirmed the extracellular protein levels of p11 decreased in the three p11-antisense cells lines and increased in the four p11-sense cell lines, relative to controls. The development of the stable HT1080 clonal cell lines with altered cell surface p11 afforded the opportunity to examine the role of p11 in plasminogen binding and activation.

EXAMPLE 6

The Role of p11 in the Generation of Plasmin

Figure 11:
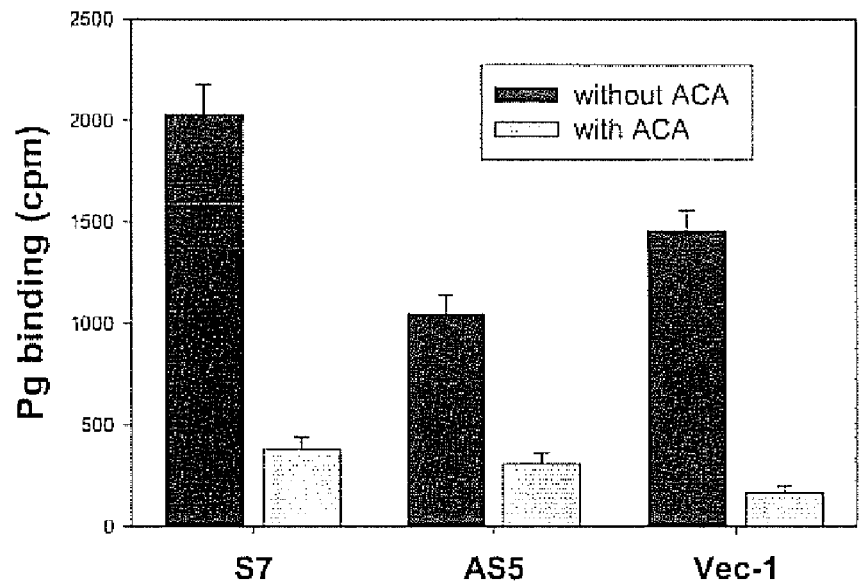
FIG. 11. p11 regulates plasminogen binding and activation on the cell surface. A) Plasminogen binding to S7, AS5, and Vec-1 cells in the absence or presence of ε-ACA was examined with radioiodinated plasminogen. B) Plasminogen activation on the surface of S7, AS5, and Vec-1 cells was measured by using plasmin amidolytic substrate with various concentrations of plasminogen. C) 1 μM [Glu]-plasminogen was added to confluent cells and cell-generated plasmin activity was measured at 405 nm after addition of the plasmin substrate H-D-norleucyl-hexahydrotyrosyl-lysine-p-nitroanilide. D) The gelatinolytic activity of S7, AS5, and Vec-1 conditioned media was measured with gelatin zymography.
Figure 11:
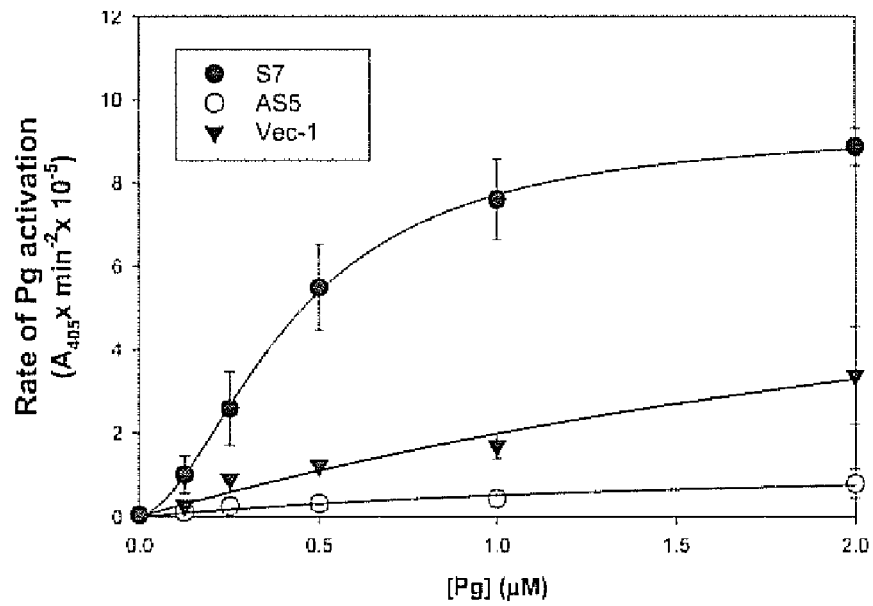
Figure 11:
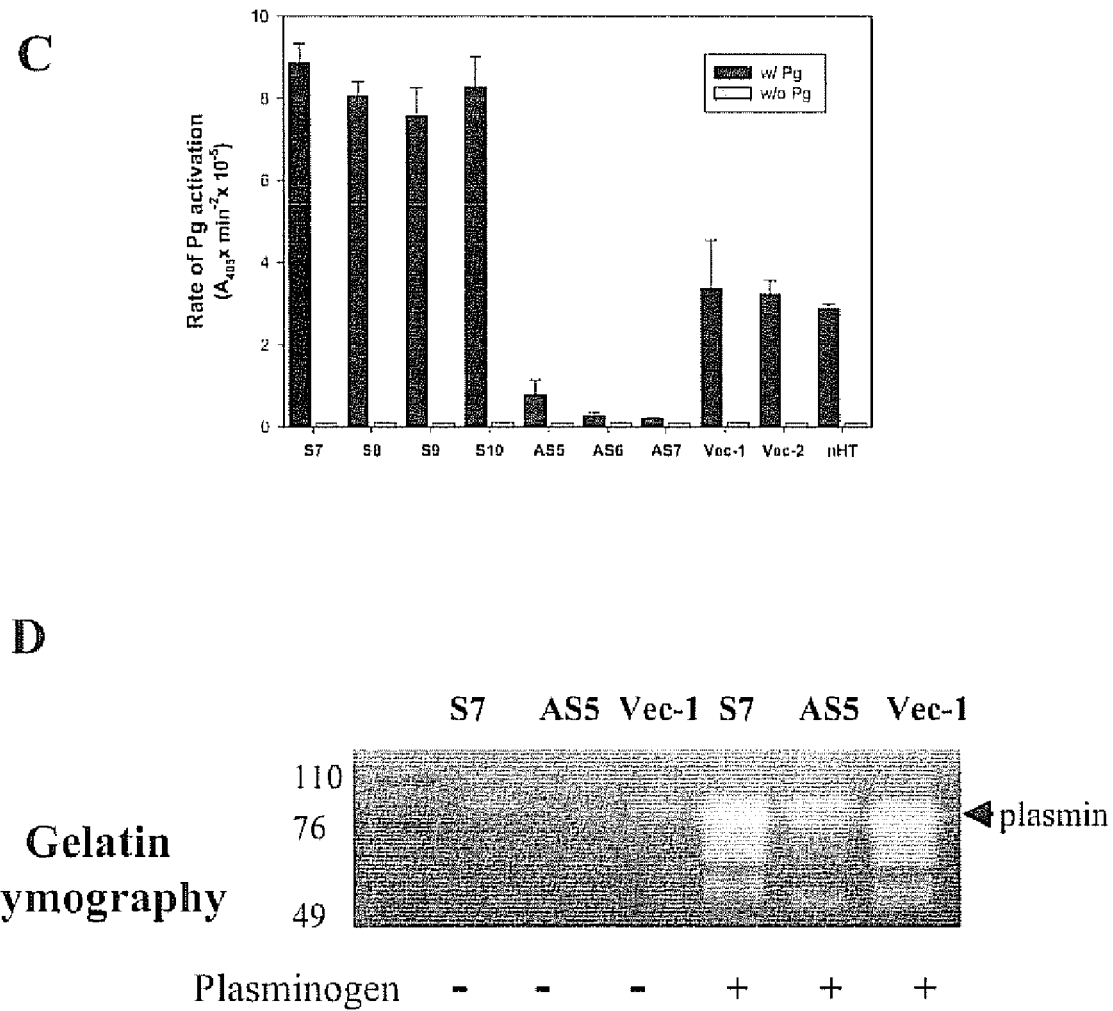

The binding of plasminogen to cells involves the interaction of the lysine-binding kringle domains of plasminogen with the carboxy-terminal lysines of plasminogen receptors. This binding interaction can be inhibited by lysine analogues such as ε-aminocaproic acid (ε-ACA) or by CpB treatment, which removes the carboxy-terminal lysines of plasminogen receptors. In order to examine if changes in the extracellular levels of p11 corresponded to changes in the plasminogen binding capacity of the HT1080 cells, representative cell lines were incubated with plasminogen and after washing the cells with buffer, the levels of bound plasminogen were determined. As shown in FIG. 11A, the S7 clone showed a ~39% enhancement of plasminogen binding compared to the Vec-1 cells. Plasminogen binding to these cell lines was reduced by either ε-ACA or CpB treatment. Conversely, the binding of plasminogen to the AS5 cells was reduced by about 28% compared with the Vec-1 cells.

To examine the ability of the cell lines to convert plasminogen to plasmin, cellular plasmin formation was monitored by washing the cells with serum-free media. The initial rates of plasmin formation were determined after addition of plasminogen and a colorimetric plasmin substrate. Plasmin production of the S7 and AS5 cell lines correlated with their respective extracellular p11 levels over a wide range of plasminogen concentrations (FIG. 11B). Next, a comprehensive analysis of several different cell lines was conducted. Cell lines were incubated with 2 µM plasminogen and plasmin generating activity was determined. Cellular plasmin formation by the S7 cells was 3-fold higher than cellular plasmin production by the Vec-1 cells, while plasmin production by the AS5 cells was inhibited by almost 80% compared to Vec-1 cells. Strikingly, plasminogen activation by the AS6, and AS7 cell lines was barely detectable, showing an approximate 95% reduction compared to the Vec-2 cells (FIG. 11C). In contrast, the S8, S9 and S10 cell lines showed a 2.5-fold increase in plasmin generation compared to the Vec-2 cells.

To determine the secreted proteolytic activity of representative cell lines, cells were incubated in the presence or absence of 0.5 µM plasminogen for 5 hours and the conditioned media was subjected to gelatin zymography. In the absence of plasminogen, very little proteolytic activity was observed (FIG. 11D). However, when the cell lines were incubated with plasminogen, the resultant increase in gelatinolytic activity was highest for the S7 clone and lowest for the AS5 clone. The molecular weight of the major band of proteolytic activity was 80 kDa, consistent with the release of plasmin into the media by the cells.

Figure 12:
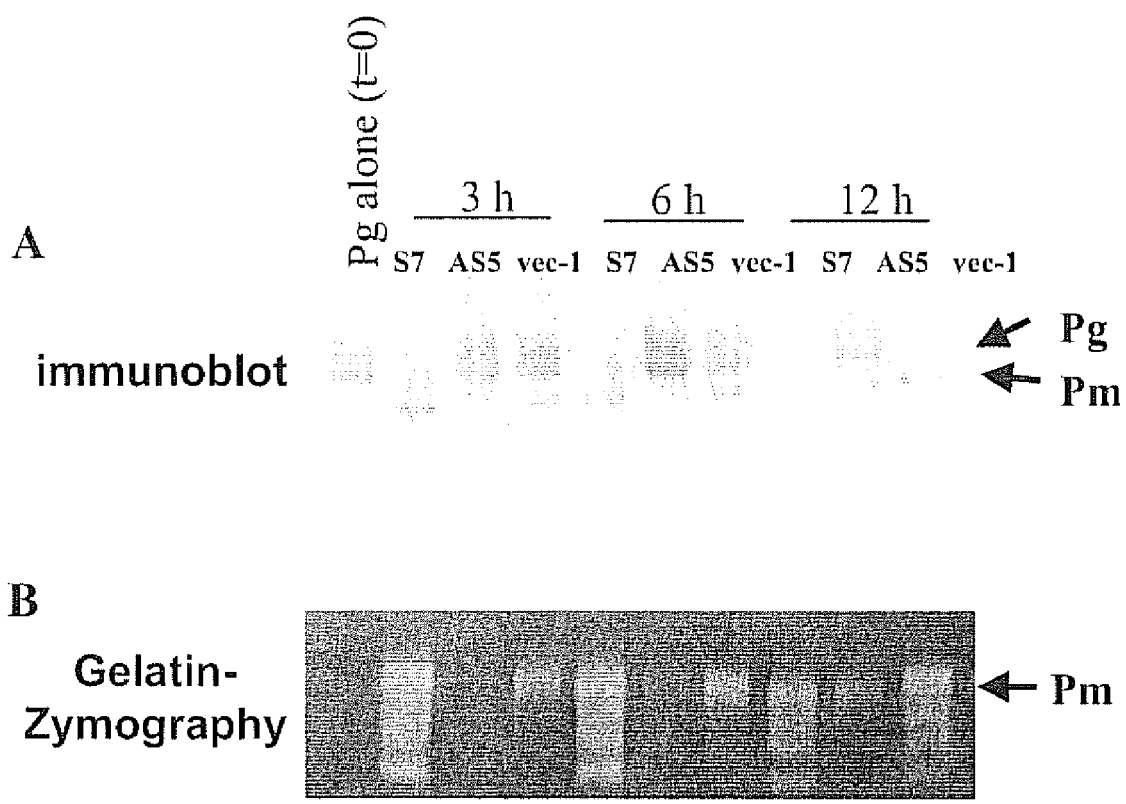
FIG. 12. Role of p11 in plasmin formation and degradation on the cell surface. The S7, AS5, and Vec-1 cells were incubated with 0.5 μM [Glu]-plasminogen for indicated time periods. The conditioned media was collected and cleared. A) Plasmin formation and degradation were examined by immunoblot analysis with mouse anti-human plasminogen monoclonal antibody. B) The conditioned media was also subjected to gelatin zymography.

In addition to cleaving several extracellular matrix proteins, plasmin is also capable of autoproteolysis. This self-destruct mechanism is thought to be important to prevent collateral tissue damage by the accumulation of plasmin in the tissues. It is disclosed herein that p11 is also capable of stimulating plasmin autoproteolysis (Fitzpatrick et al., 2000). When the cell lines were incubated with plasminogen, the levels of plasmin(ogen) protein were determined by Western blot analysis (FIG. 12A) and the plasmin proteolysis activity was determined by gelatin zymography (FIG. 12B), indicating time-dependent autoproteolysis of plasmin. Three hours after plasminogen addition, the S7 cell line had converted most of the exogenous plasminogen to plasmin (FIG. 12A) and was expressing a high level of plasmin activity (FIG. 12B). In contrast, the AS5 clone had not produced measurable levels of plasmin protein and its plasmin activity was not detectable. The control, Vec-1 cells had produced a small amount of plasmin protein and consequently showed a low level of plasmin activity during this time. Twelve hours later, the plasmin protein produced by the S7 clone had been autoproteolyzed and its gelatinolytic activity had also decreased. In contrast, the AS5 clone had produced only a small amount of plasmin protein and displayed low levels of plasmin activity compared to the Vec-1 cells. These results establish that p11 stimulates both plasmin formation and autoproteolysis on the cell surface.

While p11 is a plasminogen-binding protein capable of stimulating the tPA- and uPA-catalyzed conversion of plasminogen to plasmin in vitro, it was heretofor unclear if p11 played a role in plasminogen regulation in vivo. According to the present invention, the loss of p11 from the surface of HT1080 cells was shown to result in a loss of plasminogen binding (FIG. 11A) and a dramatic loss of plasmin production by these cells (FIG. 11B, C). Depending on the method of delivery of the pLin-p11 antisense vector to the cells, the loss in plasmin activity ranged from 76% to 95%. On the other hand, increased extracellular p11 levels correspond with increased extracellular plasminogen binding as well as enhanced plasminogen activation (FIG. 11A, B, C).

That p11 could account for as much as 95% of the plasmin generated by HT1080 cells was unexpected. While plasminogen may bind to all cell-surface proteins with carboxyl-terminal lysine residues, only the binding of plasminogen to proteins with carboxyl-terminal residues which are colocalized to uPAR are thought to be important for plasminogen activation. Although the number of plasminogen receptors is 4-5 orders of magnitude higher than that of uPAR, bound plasminogen is rate-limiting for cell-surface-mediated activation of plasminogen by urokinase (Stephens et al., 1989; Namiranian et al., 1995). The observation that loss in p11 from the surface of HT1080 cells results in an approximate 28% loss in plasminogen binding but a 76% loss in plasmin production (FIG. 11A, C) suggests that p11 may be one of the few plasminogen receptors that is accessible to uPAR. Considering the small increase in extracellular p11 observed between the S7 and Vec-1 cells, it was interesting that the rate of plasminogen conversion more than doubled. This result is compatible with the suggestion that the p11-plasminogen complex is rate-limiting in terms of uPA-dependent plasmin production in these cells.

While not wishing or intending to be bound by theory, one skilled in the art would reasonably expect changes in the extracellular levels of p11 to have such dramatic effects on plasmin production because of three key properties of p11. First, p11 possesses the requisite carboxy-terminal lysine residues that serve as the hallmark of a plasminogen receptor and loss of these residues blocks the activity of the protein in vitro (Fogg et al., 2002, Biochemistry 41:4953-4961). Second, the interaction of p11 with plasminogen results in the induction of an activator-susceptible conformational change in plasminogen (Kassam et al., 1998b). Third, it is disclosed herein that p11 colocalizes with uPAR on the surface of HT1080 cells (FIG. 10). Therefore, the skilled artisan may expect p11 to be a potent regulator of plasminogen activation because it binds plasminogen via its carboxyl-terminal lysine residues, induces a conformational change in plasminogen and colocalizes with uPAR.

In addition to the stimulation of plasmin production by p11, it is also demonstrated herein that p11 stimulates plasmin autoproteolysis in vitro and in situ, which presumably prevents collateral tissue damage that might occur due to action of constitutively activated cell-bound plasmin. As shown in FIGS. 12A and B, enhanced p11 levels on the surface of the HT1080 cells result in a transient pulse of plasmin activity, due to the stimulation of plasmin production and autoproteolysis by p11.

EXAMPLE 7

Clonal Cell Lines and Plasminogen Activator Activity Of Cell Lines

HT1080 cells constitutively secrete the plasminogen activators, tissue plasminogen activator (tPA) and the urokinase-type plasminogen activator (uPA). The uPA is generally considered to be the predominant plasminogen activator secreted by cancer cells. The uPA is secreted by cancer cells is in its single-chain proenzyme form, pro-uPA. The pro-uPA is rapidly converted to its active two-chain form by cell-bound plasmin (Stephens et al., 1989). The uPA produced by the action of plasmin on pro-uPA then converts plasminogen to plasmin thus participating in an exponential double-reciprocal zymogen activation cycle.

Figure 13:
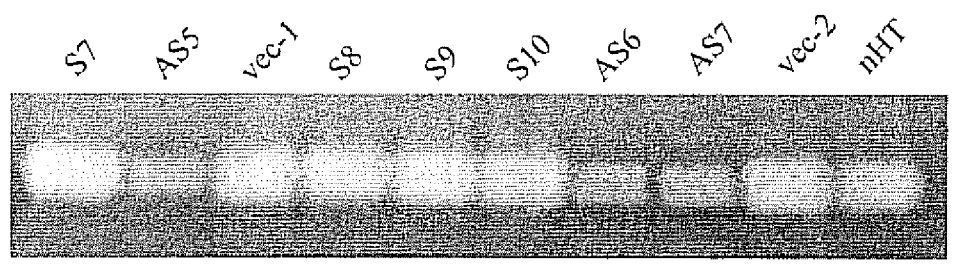
FIG. 13. Plasminogen activator activity of cell lines. The level of cell surface uPA activity (A) or uPA activity in the conditioned media (B) of the cell lines was examined by plasminogen activator zymography. C, the mobility of plasminogen activator activity is compared with pro-u PA and uPA standards.
Figure 13:
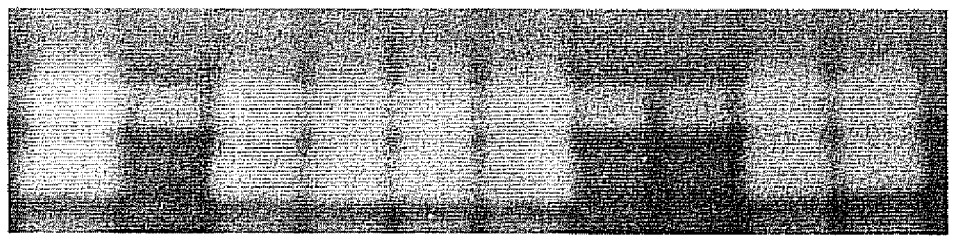
Figure 13:
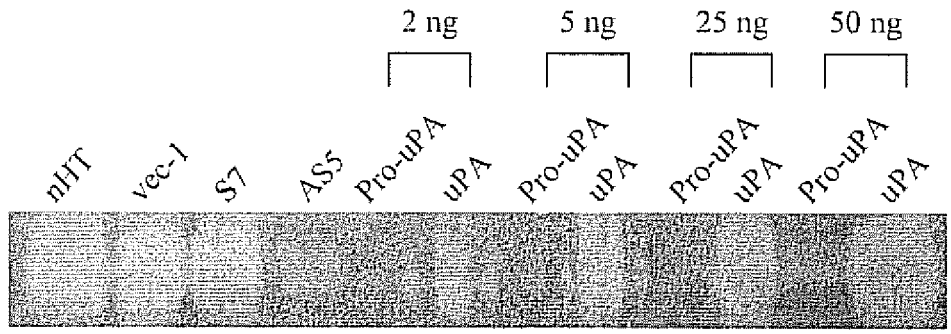

The levels of plasminogen activator activity of various cell lines were determined by comparative zymography. These assays were performed with acid-washed cell extracts to detect cell-bound uPA or conditioned media to detect uPA released into the media. As reported by others, uPA activity was only determined by reverse zymography. Compared to non-transfected HT1080 cells or the vector control cells, the p11-antisense cell lines had lower levels of uPA activity, while the sense-p11 cell lines had elevated uPA activity (FIG. 13 A, B). Since the cell lines secrete similar levels of tPA and uPA protein (FIG. 9E), this indicates that more pro-uPA was converted to uPA by the p11-sense cell lines whereas much less pro-uPA was converted to uPA by the p11-antisense cell lines. Thus, the activation of pro-uPA by the cell lines is dependent on their plasmin levels. Therefore, p11 indirectly regulates the plasminogen activator activity of the cell lines by regulating the plasmin levels of the cells and hence the plasmin-dependent conversion of pro-uPA to uPA.

Human tumor cells are commonly found to secrete the single-chain zymogen, pro-uPA (Dano et al., 1985, Adv Cancer Res 44:139-266). Pro-uPA, which is rapidly converted to its active two-chain form by cell-bound plasmin, converts plasminogen to plasmin thus participating in an exponential activation cycle. It has been established in the art that HT1080 cells require the presence of plasminogen to facilitate the conversion of cell-surface pro-uPA to uPA (Stephens et al., 1989). Interestingly, although the total cellular levels of uPA (pro-uPA and uPA) were similar among the various cell lines that were looked at, the antisense-p11 cell lines showed much less uPA activity (FIG. 13). Therefore, this loss in the ability of the antisense-p11 cell lines to convert pro-uPA to uPA was most likely secondary to the loss in the plasmin generating activity in these cell lines.

The results of the experiments disclosed herein show that plasminogen activation by HT1080 cells is regulated by the extracellular p11. Interestingly, the cell surface annexin II remained unchanged in the antisense p11 cell lines (FIG. 9B) despite the loss of as much as 90% of the cellular plasminogen activation activity (FIG. 11B,C). This discovery was surprising because it was originally reported that the annexin II was an important regulator of plasminogen activation (Cesarman et al., 1994, J Biol Chem 269:21198-21203; Najjar et al., 1994, J Biol Chem 269:21191-21197). The authors of those studies concluded that p11 was not present on the endothelial cell surface and that the cleavage of annexin II by an unidentified protease resulted in the generation of a new carboxy-terminal lysine residue on the protein. Subsequent reports have shown however, that plasminogen binding to cells does not correlate with annexin II (Andronicos and Ranson, 2001, Br J Cancer 85:909-916) and that extracellular annexin II does not express carboxy-terminal lysine residues (Hawley et al., 2001). Interestingly, an AIIt-cathepsin B complex has been immunoprecipitated from the surface of human breast carcinoma and glioma cells and immunofluorescence staining of these cells has confirmed that p11 is present as AIIt-cathepsin B complex (Mai et al., 2000a; Mai et al., 2000b). Other studies have shown that the annexin II-p11 complex can be immunoprecipitated from the surface of endothelial cells (Kassam et al., 1998b). Therefore, based on the available evidence, it is unlikely that the annexin II plays a role in the uPA-dependent plasminogen activation. However, either p11 or p11 complexed with annexin II on the cell surface (AIIt) is responsible for the plasminogen regulation.

EXAMPLE 8

Figure 14:
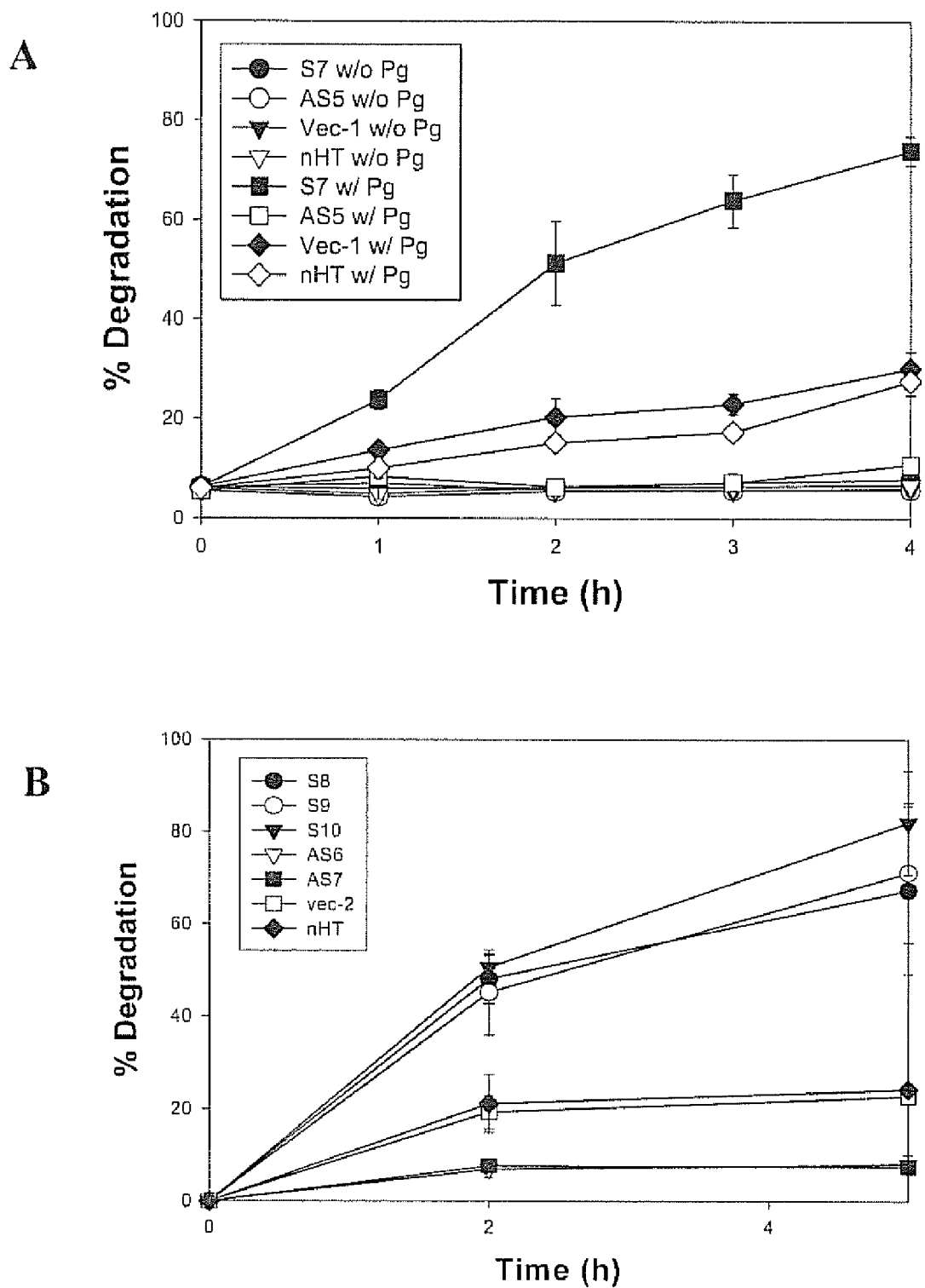
FIG. 14. Correlation of p11 expression with extracellular matrix hydrolysis. The proteolytic activity of the virally (A) or nonvirally (B) transfected cells towards an extracellular matrix generated by human aortic smooth muscle cells was also examined in the HT1080 cell lines. nHT means normal untransfected HT1080 fibrosarcoma cells.

The Role of p11 in Extracellular Matrix Hydrolysis, Cell Invasion Through an Extracellular Matrix, and Tumor Cell Metastasis Smooth muscle cells elaborate an extracellular matrix (SM-ECM) comprising glycoproteins such as fibronectin, and other structural proteins such as collagen and elastin. The SM-ECM is a valuable model system for studying the kinetics and mechanism of destruction of the extracellular matrix by tumor cells (Jones et al., 1979, PNAS USA 76:353-357). Many tumor cells, including HT1080 cells, but not normal fibroblasts, degrade the SM-ECM. Labeled SM-ECM was produced by culturing rat smooth muscle cells with [$^3$H]-glucosamine and after removal of the smooth muscle cells, the HT1080 cell lines were seeded on the matrix. Plasminogen was added and the radioactivity released from SM-ECM was monitored over time. As expected, both the wild-type cells and vector control cells rapidly hydrolyzed the SM-ECM (FIG. 14). Consistent with their decreased plasminogen activation capability, the amount of SM-ECM hydrolyzed by the p11-antisense cell lines was about 30% of the control cells. Furthermore, the p11-sense cell lines showed an approximate 3-fold increase in SM-ECM hydrolysis compared to the control cells.

Figure 15:
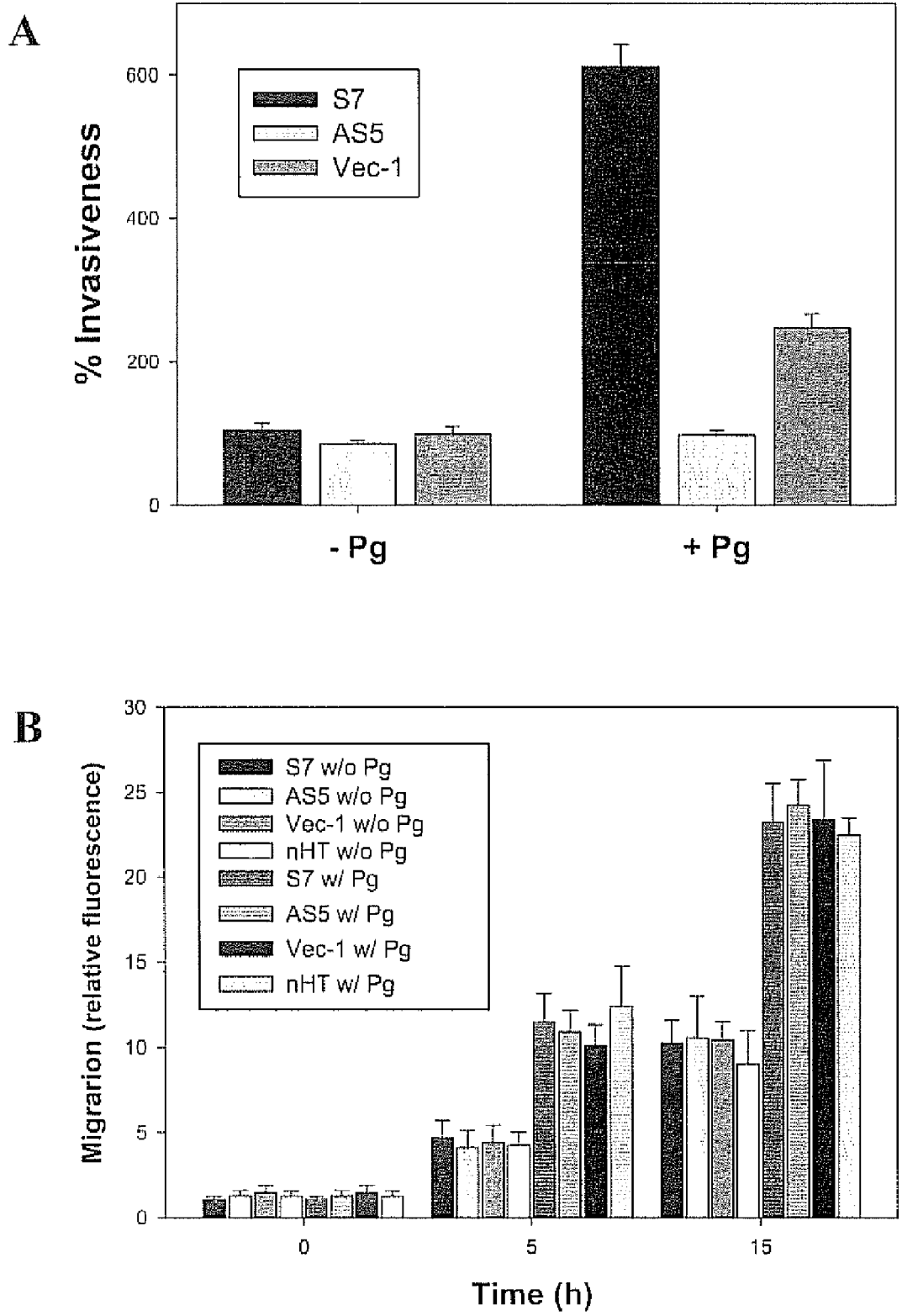
FIG. 15. Role of p11 in cell invasiveness. A) Invasiveness of S7, AS5, and Vec-1 cells was examined with a Matrigel™-coated invasion chamber. B) Migration of these cells was also assessed by using QCM Cell Migration Assay™ Kit. C) Metastatic potential of S7, AS5, and Vec-1 cells was examined in SCID mice. Five weeks after tail vein injection, mice were sacrificed and lung metastatic foci were counted. Tested with ANOVA, * vs ** are significantly different (p<0.01).
Figure 15:
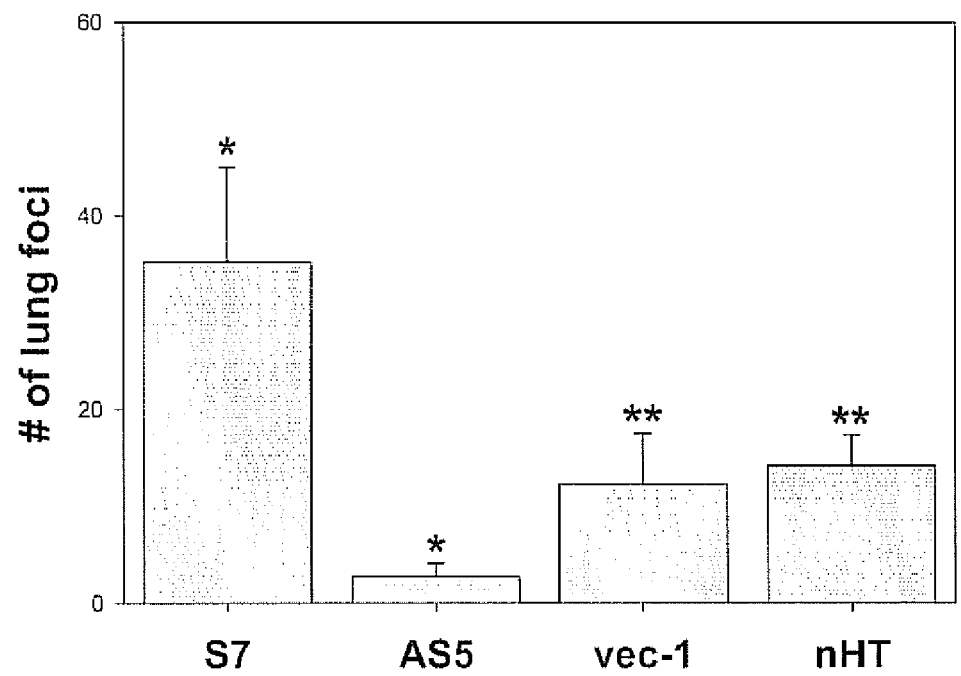

The invasion of cancer cells through the extracellular matrix involves activation of cell surface proteases as well as changes in cell motility. HT1080 cell lines and a Matrigel™ assay system were employed to elucidate the role of p11 in the invasiveness of the HT1080 cells. This assay system comprises an upper and lower chamber separated by an 8 μm pore size polycarbonate filter coated with Matrigel™, which acts as a basement membrane surrogate. The cell lines were seeded on the Matrigel™ in the upper chamber and the number of cells that transversed the Matrigel™ and appeared on the underside of the Matrigel™ was determined. When the experiment was performed in the absence of plasminogen, the invasiveness of the three representative cell lines was similar (FIG. 15A). However, in the presence of plasminogen, the invasiveness of the AS5 cell line (p11 antisense) was decreased by about 60% compared to the vector control cells, whereas the invasiveness of the S7 cell line (p11 sense) was increased by 2.5-fold. Interestingly, when the plasminogen-dependent rates of invasiveness were determined by subtracting the rates determined in the presence and absence of plasminogen, the plasminogen-dependent invasiveness of the AS5 cell line was decreased about 92% whereas the invasiveness of the S7 cell line was increased by 3.5-fold.

Changes in the invasiveness of the HT1080 cells could be due to changes in the cell-surface proteolytic activity or motility of the cells or both. The motility of the cell lines was examined by determination of their migration through the polycarbonate filter in the absence of Matrigel™. The cells were placed on the upper side of the 8-μm-pore sized filter and the number of viable cells present on the under of the filter was determined. As shown in FIG. 15B, the AS5, S7 and Vec-1 cells had similar migration rates indicating that observed changes in cellular invasiveness was not due to differences in cellular motility.

The metastatic potential of cancer cells is often related to their proteolytic and invasive capacity. To determine whether the difference in protease-dependent invasiveness of the cell lines translated to differences in metastatic potential, the ability of the clonal cell lines to extravasate and form solid tumors in SCID mice was examined. AS5, S7 or Vec-1 cells were injected into the tail vein of SCID mice and the formation of lung metastatic foci was monitored. The number of metastatic foci in the lungs decreased by 3-fold for the AS5 cell line and increased by 16-fold for the S7 cell line compared to Vec-1 cells (FIG. 15C). These results indicate that the ability of the tumor cells to intravasate and form tumors is directly related to p11 expression.

Metastasis requires the dissolution of the extracellular matrix and basement membranes and this remodeling event is due to the activity of proteolytic enzymes. Among the proteases implicated in tumor cell dissemination is the serine protease plasmin. By binding plasminogen to specific protein receptors on its surface and converting it to plasmin, the cell can harness an enzyme with broad substrate recognition to perform the local proteolytic events necessary for tumor growth, invasion and metastasis. As shown in FIG. 14, 15A, the loss in p11 from the cell surface dramatically decreases the matrix proteolysis and the invasiveness of the cells. The loss in p11 from the extracellular surface has been demonstrated to correlate with a loss in metastatic potential i.e., the ability of the HT1080 cells to extravasate and form tumors in the mouse lung. Furthermore, increases in the levels of cell surface p11 increased the invasiveness and metastatic potential of the cell lines. The observation that changes in extracellular p11 levels result in changes in plasmin generation is therefore consistent with the proposed relationship between plasmin activity and cancer cell invasiveness and metastasis potential. Although the data presented herein is consistent with a role for p11-mediated plasmin production in metastasis, the possibility that p11 could affect metastasis by other mechanisms is not ruled out. For example, p11 might affect the production of other cellular proteases such as the matrix metalloproteases or might promote the increased survivability of the HT1080 cells in the circulation or in the tissue.

EXAMPLE 9

The Role of p11 in Tumor Growth and the Effects of p11 Modulation on Tumor Growth In Vivo Since upregulation of p11 activity results in the increased production of AAPFs, which inhibit tumor growth, the effect of both increasing and decreasing p11 activity on tumor development in mice were examined. The metastatic potential of S7, AS5, and Vec-1 cells were examined in SCID mice. Five weeks after tail vein injection of those cells, mice were sacrificed and lung metastatic foci were counted. As expected, the number of metastatic foci and the size of the tumors that did form were significantly reduced in those subjects that received cancer cells treated with a composition that reduces p11 activity relative to control cancer cells (FIG. 16A,C). Furthermore, the total number of animals that developed tumors, after receiving cancer cells that were treated with either a composition that increased p11 activity or a composition that decreased p11 activity, was significantly reduced relative to those animals that received untreated cancer cells (FIG. 16B). Thus, modulation of p11 activity either up or down relative to untreated cancer cells results in a decrease in tumor development.

It was further observed that although the control HT1080 cells formed tumors in SCID mice, only about half of the p11-antisense clones formed tumors and these tumors were smaller and more poorly vascularized. Interestingly, the p11-sense did not form a primary tumor. This observation is not surprising since it is believed that tumor growth is dependent on tightly controlled proteolytic degradation of the extracellular matrix. The critical importance of an appropriate balance between proteases and protease inhibitors in these processes is suggested by the observation that extracellular matrix invasion and capillary lumen formation are inhibited in the presence of an excess of protease inhibitors and that when unchecked by protease inhibitors, excessive proteolysis is incompatible with normal capillary morphogenesis. Thus, a precisely regulated proteolytic balance is necessary for normal capillary morphogenesis (see Pepper, M. S. 2001. Extracellular proteolysis and angiogenesis. Thromb. Haemost. 86:346-355).

These observations indicate that the ability of these tumor cells to extravasate and metastasize is directly related to extracellular p11 expression.

EXAMPLE 10

Materials and Methods Used in the Foregoing Examples 5-9

Cloning of sense- or antisense-p11 gene in retroviral vectors: Sense and antisense cDNA was obtained from human p11 full length cDNA using PCR. The sense primer set was 5'-ATGCGGCCGCATGCCATCTCAAATGG-3' (SEQ ID NO:9) and 5'-ATAGATCTCTAC-TTCTTTCCCTTC-3' (SEQ ID NO:10) and the antisense primer set was 5'-ATA-GATCTAT-GCCATCTCAAATGG-3' (SEQ ID NO:11) and 5'-ATGCGGCCGCCTACTTCTTTCCCTT-CTG-3' (SEQ ID NO:12). The sense and antisense human p11 cDNA were cut with Not I and BgI II, gel purified and cloned into a Not I and BgI II-cut retroviral vector, pLin (provided by Dr. L.-J. Chang, Powell Gene Therapy Center, University of Florida, Gainesville, Fla.). The orientation of the inserts was verified by sequencing. The retroviral vectors harboring sense and antisense p11 were termed pLin-sp11 and pLin-ap11, respectively.

Plasmid transfection and retrovirus infection: The pLin-sp11 and pLin-ap11 were transfected into a PA317 packaging cell line (ATCC, Manassas, Va.) using the calcium precipitation method. The packaging cells were enriched and selected by growth in the presence of 0.5 mg/ml G418 for 2 weeks. At confluence, conditioned media were collected and used for transduction of HT1080 fibrosarcoma cells (ATCC, Manassas, Va.). The stably transduced HT1080 cells were selected with 300 µg/ml G418 for two months and clonal cell lines selected by p11 protein expression levels as assessed by Western analysis. The stable cell lines transduced with sense p11, antisense p11, or empty vector were termed S7, AS5, and Vec-1, respectively. HT1080 fibrosarcoma cells were also transfected with pLin, pLin-sp11, or pLin-ap11 by using LIPOFECTAMINE 2000 Reagent (Gibco BRL, Rockville, Md.), selected with 300 µg/ml G418 (Bioshop Canada, Burlington, ON), and clonal cell lines selected by p11 protein expression.

Northern blot analysis: Total RNA was isolated from S7, AS5, and Vec-1 cells using the Rneasy™ Kit (manufacturer's instruction, QIAGEN, Valencia, Calif.). Expression of p11 mRNA in these cells was examined according to the NorthernMax™-Gly procedure (Ambion, Austin, Tex.). Total RNA (20 µg) was electrophoretically separated by glyoxal agarose gel electrophoresis and transferred to a nylon membrane. Hybridization was performed with a radioactive cDNA probe for p11 ($10^6$ cpm/ml) labeled with $^{32}$P-α-dCTP by using Ready-To-Go™ DNA Labeling Beads (Amersham Pharmacia Biotech, Piscataway, N.J.).

Immunoblot analysis: Cells were lysed with RIPA buffer containing 1 mM PMSF, 5 µg/ml leupeptin and 5 µg/ml aprotinin. The cell lysates (25 µg), reconstituted in reducing or nonreducing Laemmli buffer, were subjected to SDS-PAGE and transferred to a nitrocellulose membrane. In order to detect p11, the membrane was fixed in 4% paraformaldehyde at room temperature for 10 min. After blocking with a 5% skim milk solution, the membrane was incubated with 0.25 ng/ml of an anti-human p11 mAb (BD Transduction Laboratories, San Jose, Calif.), 0.5 ng/ml of an anti-human uPA pAb (American Diagnostica, Greenwich, Conn.), 0.5 ng/ml of an anti-human tPA mAb (American Diagnostica, Greenwich, Conn.), 0.5 ng/ml of an anti-human PAI-1 mAb (American Diagnostica, Greenwich, Conn.), 0.5 ng/ml of an anti-human PAI-2 mAb (American Diagnostica, Greenwich, Conn.), 0.5 ng/ml of an anti-human uPAR pAb (Santa Cruz Biotechnology, Santa Cruz, Calif.) or 1 ng/ml of an anti-human α-tubulin mAb (Oncogene Science, Mineola, N.Y.). These mAbs were detected with 0.2 ng/ml of a horseradish peroxidase (HRP)-conjugated goat anti-mouse IgG and Super Signal™ detection kit (Pierce, Rockford, Ill.).

Detection of cell surface annexin II and p11: Subconfluent cells were biotinylated by incubation with DPBS (Gibco BRL, Rockville, Md.) containing 0.5 mg/ml Sulfo-NHS-Biotin (Pierce, Rockford, Ill.) for 30 min at room temperature. After washing with DPBS, cells were lysed with RIPA buffer containing 1 mM phenylmethylsulfonylfluoride (PMSF), 1 µg/ml leupeptin and 1 µg/ml aprotinin. The lysate was incubated with 20 µl of streptavidin-agarose beads (Sigma) or control agarose beads at 4° C. overnight. After washing with ice-cold TBS containing 0.5 mM $CaCl_2$, Tween-20 and 1 mM PMSF, bound proteins were eluted with SDS-sample buffer and subjected to immunoblot analysis using an anti-annexin II mAb (Transduction Laboratories, San Jose, Calif.).

For p11 detection, the cells were surface-biotinylated and the total cell extract was precleared with 20 µl of protein A/G Plus-agarose beads (Santa Cruz Biotechnology, Santa Cruz, Calif.). The precleared sample was then incubated with 4 µg of anti-p11 mAb (Transduction laboratory) on ice overnight. The mixture was subsequently incubated at 4° C. with 50 µl of protein A/G Plus-agarose beads at 4° C. for 4 hours on a platform rotator, centrifuged, and the pellet was washed five times with TBS containing 0.5 mM $CaCl_2$, 0.05% Tween-20, and 1 mM PMSF. The pellet was then subjected to SDS-PAGE and probed with streptavidin HRP.

Immunofluorescence staining: HT1080 cells were cultured on fibronectin-coated glass coverslips. To stain for surface antigens, cells were washed two times with DPBS and fixed with 4% paraformaldehyde in PBS for 10 min at 4° C. For detection of intracellular antigens some cells were permeabilized with cold 100% ethanol for 10 min at 4° C. After washing with DPBS, cells were blocked with 3% bovine serum albumin in PBS for 1 h at 4° C., incubated with primary antibody for 1 h, washed four times washes with DPBS and incubated with cy3-conjugated second antibody. Cells were then washed and mounted with Prolong Antifade™ (Molecular Probes, Eugene, Oreg.) reagent and observed on a Zeiss Axioskop microscope (Oberkochen, Germany) and visualized using a Zeiss Axioskop microscope (Oberkochen, Germany) and a digital camera (RS Photometrics, Tucson, Ariz.). Confocal microscopy was performed on a Leica DM RXA2 microscope (Princeton Instruments Scientific), CCD camera (ST-138 controller KAF1600 chip) with detector cooled to −40 C. Analysis was performed with a computer controlled camera and microscope with in-house software, C++ Snapin for Winview (Princeton Instruments). Typically, 0.3 micron optical slices were examined.

Cell surface plasminogen binding assay: Recombinant human [Glu]plasminogen (American Diagnostica, Greenwich, Conn.) was radioiodinated as previously described (Suenson and Thorsen, 1988, Biochemistry 27:2435-2443). Briefly, plasminogen (10 µM) was incubated for 3 min at room temperature with 37 MBq (=1 mCi) of $Na^{125}I$ and three Iodo-Beads (Pierce, Rockford, Ill.) in PBS. Free $Na^{125}I$ and protein were separated using a PD-10 column (Sephadex G-25, Amersham Pharmacia Biotech, Uppsala, Sweden) equilibrated, and eluted with PBS. The specific activity of the protein preparations ranged from 1000 to 2000 cpm/pmol of protein. Confluent cells in 24-well plates were rinsed with ice-cold DPBS and incubated with 10 nM radioiodinated plasminogen and 0.49 µM cold plasminogen in the presence or absence of 10 mM ε-ACA at 4° C. for 1 hr. The radioactivity of cells was counted after washing the cells with ice-cold DPBS three times.

Plasminogen activation assay on cell surface: The kinetics of cell-mediated plasminogen activation was determined by measuring amidolytic activity of the plasmin generated from plasminogen. Cells were seeded on 24-well culture plates. The reaction was conducted with the substrate H-D-norleucyl-hexahydrotyrosyl-lysine-p-nitroanilide (Spectrozyme #251, American Diagnostica, Greenwich, Conn.) at a final concentration of 100 µM in phenol red-free DMEM. The reaction was initiated by the addition of 0.5 µM [Glu]-plasminogen to 80% confluent cells and was monitored at 405 nm in a Perkin Elmer HTS 7000 Bioassay reader (Shelton, Conn.).

Zymography: Confluent cells ($1\times10^5$/well) were cultured for indicated time periods in serum-free DMEM in the presence or absence of 0.5 µM human [Glu]plasminogen. Cell debris was removed from the collected supernatant by centrifugation (2000 g, 4° C., 10 min). Cell-bound PA was prepared by incubation of the cells with 200 µl of 50 mM glycine-HCl in 0.1 M NaCl (pH 3.0) for 3 min at room temperature and consequent neutralization with 50 µl of 0.5 M Tris-HCl buffer (pH 7.8). The eluate was collected and cleared by centrifugation. The conditioned medium was subjected to non-reduced SDS-PAGE containing 1 mg/ml of gelatin in the absence or presence of 13 µg/ml plasminogen. After electrophoresis, the gels were washed twice with 200 ml of 50 mM Tris-HCl, 150 mM NaCl, 2.5% (v/v) Triton X-100, pH 7.4 for 2 h at room temperature and 3 times with water for 5 min. Gelatin gels were incubated at 37° C. overnight in 50 mM Tris-HCl (pH 7.4), 150 mM NaCl, 2.5% (v/v) Triton X-100. Gels containing plasminogen were incubated in 100 mM glycine-NaOH, pH 8.3, for 3 h at 37° C. Gels were stained with Coomassie Brilliant Blue R-250 0.5% (w/v) in 45% (v/v) methanol, 10% (v/v) acetic acid and destained in the same solution without dye. Protease activity was visualized as a clear zone against a blue background.

Invasion assay: Cell invasiveness was assayed using a modified Transwell system with Matrigel-coated polycarbonate filters (8 µm pore size, Costar, Cambridge, Mass.). After rehydration of filters, cells ($2\times10^5$) were seeded in the upper chamber in DMEM containing 10% (v/v) FBS. DMEM supplemented with 10% (v/v) FBS was placed in the lower chamber. After 5 hours of incubation at 37° C. in 5% $CO_2$/95% air (v/v), the media in upper chamber was changed with serum free DMEM containing 0.25 µM [Glu]plasminogen. After 18 hours of incubation, cells in the lower chamber were stained with Diff-Quick™ Stain Set (DADE International, Miami, Fla.) and counted under microscopic fields.

Proteolysis of smooth muscle cell-derived extracellular matrix: Human aortic smooth muscle cells (AoMC, Clonetics, San Diego, Calif.) were grown in AoMC growth media provided by the manufacturer. AoMC were seeded in 24-well tissue culture plates ($1\times10^5$) following which the media was supplemented with 1 µCi/ml [$^3$H]-glucosamine HCl (Perkin Elmer Life Sciences, Boston, Mass.). Five days later, cells were removed by addition of 0.25 mM $NH_4OH$, 0.5% Triton X-100 for 5 min at room temperature. The labelled extracellular matrix was washed with DPBS three times and stored at 4° C. Cells ($1\times10^6$/well) were plated on the rehydrated matrix in DMEM containing 10% FBS and incubated for 5 hours. After washing with serum-free DMEM, the cells were incubated with serum-free DMEM with or without 0.5 µM plasminogen at 37° C. in 5% $CO_2$/95% air (v/v) for various time periods. The media was then collected and subjected to liquid scintillation counting. To determine the value for 100% degradation, the matrix was subjected to hydrolysis with 10 µM trypsin.

Cell migration: Cell migration was conducted with the QCM Cell Migration Assay Kit™ (Chemicon International, Tumecula, Calif.) and carried out according to manufacturer's instruction. Briefly, cells ($5\times10^4$ cells/well) were seeded in DMEM containing 10% FBS and incubated for 5 hours. Media in the upper chamber was changed with serum free media with or without 0.2 µM [Glu]plasminogen and incubated for 4 or 15 hours at 37° C. in 5% $CO_2$/95% air (v/v). The cells that had migrated to the lower chamber were detached, lysed and detected by CyQuant™ GR dye.

Mouse lung metastasis and tumor development assays: S7, AS5, and Vec-1 cells ($1\times10^6$ cells/0.1 ml) were injected intravenously into the tail vein of SCID mice (n=6) (Jackson Laboratories, Bar Harbor, Me.). Mice were sacrificed 5 weeks after inoculation and extent of lung metastasis was determined as number of foci and lung mass. HT1080 cells were injected intradermally and tumor size measured after 20 days. Thirteen mice were used in each group. Tumors were dissected from mice after 20 days.

EXAMPLE 11

RNA Interference-Mediated Silencing of p11 Gene

Summary p11 (a.k.a. S100A10) is a key plasminogen receptor of the extracellular cell surface that is overexpressed in many cancer cells. Prior to the instant invention, p11 was thought by one skilled in the art to be anchored to the plasma membrane via the phospholipid-binding sites of its binding partner, annexin A2 (a.k.a. p36). In this example, using the potent and highly sequence-specific mechanism of RNA interference (RNAi), the inventor has stably silenced the expression of the p11 gene in colorectal (CCL-222) cancer cells. It is herein shown that siRNA expression mediated by the pSUPER vector causes efficient, stable, and specific down-regulation of p11 gene expression. The siRNA-mediated down-regulation of p11 gene expression resulted in a major decrease in the appearance of extracellular p11 protein and correlated with approximately a 45% loss of plasminogen binding, a 65% loss in cellular plasmin generation and a complete loss in plasminogen-dependent cellular invasiveness. It was also observed that the CCL-222 cells do not express annexin A2 on their extracellular surface. Thus, the data presented herein shows that annexin A2 is not required by p11 for its association with the plasma membrane, for its colocalization with uPAR, or for its binding and activation of plasminogen.

Introduction

Double-stranded RNA (dsRNA)-dependent posttranscriptional gene silencing, or RNA interference (RNAi) refers to the mechanism of sequence-specific, post-transcriptional gene silencing initiated by dsRNA homologous to the gene being suppressed. RNAi was originally described in *Caenorhabditis elegans* (Fire, A., et al., (1998) *Nature* 391, 806-811; Timmons, L. and Fire, A. (1998) *Nature* 395, 854) and *Drosophila melanogaster* (Kennerdell, J. R. and Carthew, R. W. (2000) *Nat. Biotechnol.* 18, 896-898; Yang, D., Lu, H., and Erickson, J. W. (2000) *Curr. Biol.* 10, 1191-1200) as a mechanism to protect against invasion by foreign genes and has subsequently been demonstrated to be utilized by diverse eukaryotes such as insects, plants, fungi and vertebrates (reviewed in Agami, R. (2002) *Curr. Opin. Chem. Biol.* 6, 829-834; Cottrell, T. R. and Doering, T. L. (2003) *Trends Microbiol.* 11, 37-43; Fire, A. (1999) *Trends Genet.* 15, 358-363; Hannon, G. J. (2002) *Nature* 418, 244-251; Voorhoeve, P. M. and Agami, R. (2003) *Trends Biotechnol.* 21, 2-4). However, in most mammalian cells dsRNA provokes a strong cytotoxic effect presumably by the activation of PKR and 2'-5' oligoadenylate polymerase (Clarke, P. A. and Mathews, M. B. (1995) *RNA.* 1, 7-20; Baglioni, C. and Nilsen, T. W. (1983) *Interferon* 5, 23-42). Elbashir et al. first reported that in vitro synthesized, small interfering RNA (siRNA) (19-23 nt), could induce RNA interference in mammalian cells and was as potent and effective as long dsRNA but did not induce global changes in gene expression (Elbashir, S. M., Harborth, J., Lendeckel, W., Yalcin, A., Weber, K., and Tuschl, T. (2001) *Nature* 411, 494-498; Elbashir, S. M., Lendeckel, W., and Tuschl, T. (2001) *Genes Dev.* 15, 188-200). It was shown that during RNAi processing, long dsRNA was first degraded into 19-23 nt siRNA and then recruited into an RNA-induced silencing complex (RISC) to degrade corresponding mRNA. Mechanistically, dsRNAs are processed to siRNA by Dicer, a cellular ribonuclease III, which generates duplexes of about 21 nt with 3'-overhangs (Hammond, S. M., Bernstein, E., Beach, D., and Hannon, G. J. (2000) *Nature* 404, 293-296; Zamore, P. D., Tuschl, T., Sharp, P. A., and Bartel, D. P. (2000) *Cell* 101, 25-33). In mammalian cells siRNA molecules are capable of specifically silencing gene expression without cytotoxic effects. Presumably, these siRNA avoid provoking the PKR response by mimicking the products of the Dicer enzyme. Thus, siRNAs have become a novel and potent alternative to other genetic tools such as antisense oligonucleotides to probe for gene function.

Typically the gene silencing produced by siRNA effects are short-lived, which may limit its application to cellular systems. An alternative strategy uses the endogenous expression of siRNAs by various Pol III promoter expression cassettes that allow transcription of functional siRNAs or their precursors. Agami's group reported the use of a vector system, named pSUPER that which directs the synthesis of siRNA in mammalian cells (Brummelkamp, T. R., Bernards, R., and Agami, R. (2002) *Science* 296, 550-553). They demonstrated that the expression of siRNA by this vector resulted in the efficient and specific down-regulation of gene expression. Most importantly, this vector was used to establish the stable repression of gene expression.

As described in the background of the invention, p11 (a.k.a. S100A10), a member of the S100 family of $Ca^{2+}$-binding proteins, is a dimeric protein composed of two 11 kDa subunits (reviewed in Donato, R. (2001) *Int. J. Biochem. Cell Biol.* 33, 637-668). The protein is cytosolic when present as a dimer. Typically, p11 is found in most cells bound to its annexin A2 (a.k.a. p36) ligand as the heterotetrameric $(p11)_2$(annexin $A2)_2$ complex called AIIt (supra). The formation of AIIt results in the translocation of p11 to the plasma membrane (reviewed in Choi, K. S., et al. (2003) Role of annexin II tetramer in the regulation of plasmin activity, in Joanna Bandorowicz-Pikula Ed, editor. *Annexins: Biological* importance and annexin-related pathologies., Landes Bioscience; Filipenko, N. R. and Waisman, D. M. (2003) Annexin II—Analysis of a pleiotropic protein, *Annexins: Biological importance and annexin-related pathologies.*, Landes Bioscience; Gerke, V. and Moss, S. E. (2002) *Physiol Rev.* 82, 331-371; Donato, R. and Russo-Marie, F. (1999) *Cell Calcium* 26, 85-89; Seaton, B. A. and Dedman, J. R. (1998) *Biometals.* 11, 399-404). p11 has been shown to regulate plasma membrane ion channels (Girard, C., Tinel, N., Terrenoire, C., Romey, G., Lazdunski, M., and Borsotto, M. (2002) *EMBO J.* 21, 4439-4448; Okuse, K., Malik-Hall, M., Baker, M. D., Poon, W. Y., Kong, H., Chao, M. V., and Wood, J. N. (2002) *Nature* 417, 653-656) as well as cytosolic phospholipase A2 (Wu, T., et al. (1997) *J. Biol. Chem.* 272, 17145-17153). In addition to an intracellular distribution, it has also been established that the heterotetrameric form of p11 is present on the extracellular surface of many cells (Yeatman et al. (1993) *Clin. Exp. Metastasis* 11, 37-44; Tressler et al. (1993) *J. Cell Biochem.* 53, 265-276; Balch, C. and Dedman, J. R. (1997) *Exp. Cell Res.* 237, 259-263; Siever, D. A. and Erickson, H. P. (1997) *Int. J. Biochem. Cell Biol.* 29, 1219-1223; Falcone et al. (2001) *Blood* 97, 777-784; Kassam et al. (1998) *J. Biol. Chem.* 273, 4790-4799; Mai et al. (2000) *J. Biol. Chem.* 275, 12806-12812). Extracellularly, the p11 subunit functions as a plasminogen receptor (Kassam et al. (1998) *Biochemistry* 37, 16958-16966; Choi et al. (2003) *FASEB J* 17, 235-246). The penultimate and ultimate carboxyl-terminal lysines of this subunit bind tPA and plasminogen (MacLeod et al., (2003) *J. Biol. Chem.* 278, 25577-25584) and regulate the stimulation of t-PA-dependent plasminogen activation (Fogg, et al. (2002)*Biochemistry* 41, 4953-4961).

By way of example in the practice of the present invention, a modification of the pSUPER system, i.e., the selectable pSUPER.retro.circular.stuffer (Oligoengine), was used to stably suppress the expression of the p11 gene. CCL-22 colorectal cells were transfected with the pSUPER-S100A10 or pSUPER-Control vector, and transfectants were selected with puromycin. Resistant cells were cloned and several stable lines were established. When analysed after four months, it was observed that pSUPER-S100A10 transfected clones showed a significant reduction in p11 compared to the pSUPER-Control clones. In contrast, a similar strategy utilizing full-length antisense to p11 (pLIN-S100A10) failed to significantly lower p11 levels in the colorectal cells. The loss of p11 from the surface of the pSUPER-S100A10 transfected CCL-222 cells resulted in decreased plasmin production and a loss in cellular invasiveness. Thus this example represents the first ever use of a stable siRNA system to study the function of the p11 gene.

Materials and Methods

Materials—Human colorectal adenocarcinoma cell line CCL-222 cells were purchased from the American Type Culture Collection (ATCC, USA). The carcinoma cells were maintained according to the provider's instruction. The cells were cultured in RPMI-160 supplemented with 10% fetal bovine serum (FBS; Gibco-BRL). Recombinant p11 was expressed in *Escherichia coli* and purified as described previously (Kang, H. M. et al. (1997) *Biochemistry* 36, 2041-2050). [Glu]-plasminogen and monoclonal anti-plasminogen antibody were purchased from American Diagnostica. Monoclonal anti-S100A10 antibody (Transduction Labs), polyclonal anti-annexin A2 (Santa Cruz) antibody, goat polyclonal anti-uPAR antibody (Chemicon) were used for immunofluorescence. Rabbit anti-uPAR antibody, anti-mouse and anti-rabbit horseradish peroxidase-conjugated secondary antibody were purchased from Santa Cruz Biotechnology. The monoclonal anti-annexin A2 antibody used in Western blots was from Transduction Laboratories. Anti-human α-tubulin monoclonal antibody was purchased from Oncogene Science.

Small interference RNA—The mammalian expression vector, pSUPER.retro.circular.stuffer (OligoEngine) was used for expression of siRNA in CCL-222 cells. The gene-specific insert specifies a 19-nucleotide sequence corresponding to nucleotides 199-217 downstream of the transcription start site (gtgggcttccagagcttct; SEQ ID NO:22) of p11, which is separated by a 9-nucleotide noncomplementary spacer (tctcttgaa; SEQ ID NO:23) from the reverse complement of the same 19-nucleotide sequence. This vector was referred to as pSUPER-S100A10. A control vector (pSUPER-Control) was constructed using a 19-nucleotide sequence (gcgcgctttg-taggattcg; SEQ ID NO:24) with no significant homology to any mammalian gene sequence and therefore serves as a non-silencing control (Oligoengine). These sequences were inserted into the pSUPER.retro.circular.stuffer backbone after digestion with BglII and HindIII and transformed into BL21-A1 One Shot™ supercompetent cells (Invitrogen) according to manufacturer's instructions. Several clones were obtained and the vectors were amplified. In order to verify the insertion of the p11 sequence into the pSUPER backbone, the purified vector was digested with BstI (New England Biolabs). The p11 sequence chosen contains a restriction site for BstI, therefore successful ligation of the sequence results in a restriction pattern distinct from that of unligated vector or vector ligated with the control sequence.

Transfection—CCL-222 cells were plated onto 6-well plates at 200,000 cells per well. After 24 hours, cells were transfected with 1 µg of RNAi plasmid hybrids using LIPOFECTAMINE 2000 Reagent (Gibco BRL, Rockville, Md., USA) according to manufacturer's instructions. 72 hours after transfection, cells were processed for immunofluorescence analysis to evaluate p11 expression. Stable transfected cell lines were selected with 0.5 µg/mL puromycin (Sigma, St. Louis, Mo.); clonal cell lines were selected by p11 protein expression by western blotting.

Western Blotting—Total cell lysates were prepared in RIPA lysis buffer (150 mM NaCl, 1% NP40, 50 mM TrisHCl, 0.1% SDS, 5 mM EDTA and 20 mM NaF) supplemented with 1 mM phenyl methylsulphonyl fluoride (PMSF), 5 µg/mL leupeptin, and 5 µg/ml aprotinin. Lysates were cleared by centrifugation at 14,000 g for 20 min at 4° C. and analysed by SDS-PAGE and transferred to a nitrocellulose membrane. After blocking with a 5% skim milk solution, the membrane was incubated with 0.25 µg/mL of an anti-human S100A10 mAb, 0.25 µg/mL of an anti-human Annexin II mAb, or 1 µg/mL of an anti-human-tubulin mAb. These mAbs were detected with 0.2 µg/mL horseradish peroxidase (HRP)-conjugated goat anti-mouse IgG and developed using a Super signal detection kit (Pierce, Rockford, Ill., USA).

Immunofluorescence Microscopy—Cells were cultured on coverslips until 80-90% confluence. Cells were then washed with ice-cold D-PBS and fixed with 4% PFA (paraformaldehyde) at 4° C. Alternatively, cells were permeabilized by fixation with ice-cold 100% methanol. After blocking with 1% BSA in PBS at 4° C. for 1 hour, primary antibodies (monoclonal anti-S100A10 antibody and goat polyclonal anti-annexin A2 antibody) were applied to the cells (1 µg/ml in PBS at 4° C.) for 1 hour. Fluorophore-labelled second antibody (Cy3-conjugated rabbit anti-mouse and Alexa-conjugated donkey anti-goat) was then applied at 4° C. for 1 hour. After thoroughly washing with PBS, coverslips were mounted in a solution of Prolong Antifade (Molecular Probes) and visualized using Zeiss Axioskop microscope or confocal microscope. To differentiate non-specific binding of antibodies, isotype matched, control mouse and goat antibodies were applied to cells, and incubated under the same conditions.

RT-PCR—Total RNA was extracted by using the RNeasy Mini Kit (Qiagen). Purified RNA was reverse transcribed using the One-Step RT-PCR system (Qiagen) according to the manufacturer's protocol in 20 μl final volume. Subsequently, 2 μl of cDNA was PCR-amplified using platinum Taq DNA polymerase (Invitrogen) for 22 cycles using p11, annexin A2 or GAPDH cDNA specific primers.

Plasminogen Binding Assay—Recombinant human [Glu]-plasminogen (American Diagnostica) was radioiodinated as described previously (Choi et al. (2003) *FASEB J* 17, 235-246). Plasminogen (10 μM) was incubated for 3 min at room temperature with 37 MBq (1 mCi) of $Na^{125}I$ and three Iodo-Beads (Pierce) in PBS. Free $Na^{125}I$ and protein were separated using a PD-10 column (Sephadex G-25, Amersham Pharmacia Biotech, Uppsala, Sweden) equilibrated, and eluted with PBS. The specific activity of the protein preparations ranged from 1000 to 2000 cpm/pmol of protein. Confluent cells in 24-well plates were rinsed with ice-cold DPBS and incubated with 50 nM radioiodinated plasminogen and 0.45 μM cold plasminogen in the presence or absence of 10 mM ε-ACA at 4° C. for 1 h. The radioactivity of the cells was determined after washing the cells with ice-cold DPBS three times.

Plasminogen Activation assay—Both transfected and parental CCL-222 cells were seeded in 24-well culture plates at a density of $5\times10^6$ cells/ml. After incubation in RPMI-1640 with 10% bovine serum for 6 hours, cells were rinsed two times with PBS (pH 7.4) and culture media was replaced with fresh phenol-red- and serum-free RPMI-1604 media. Purified [Glu]-plasminogen (American Diagnostica) was added at a final concentration of 0.5 μM. Conditioned media was collected and cleared by centrifugation after 2, 4, and 6 hours. The kinetics of cell-mediated plasminogen activation was determined by measuring amidolytic activity of the plasmin generated from plasminogen. The reaction was conducted with the substrate H-D-norleucyl-hexahydrotyrosyl-lysine-p-nitroanilide (Spectrozyme #251, American Diagnostica) at a final concentration of 100 μM. The reaction was initiated by the addition of substrate to 200 μl conditioned media and was monitored at 405 nm in a Perkin Elmer HTS 7000 Bioassay reader (Shelton, Conn., USA).

Cell Invasion assay—Cell invasion assay was conducted with QCM™ 96 well Cell invasion Assay Kit (Chemicon International). This well invasion plate is based on the Boyden chamber principle. This plate contains 96 inserts; each containing an 8 μm pore size polycarbonate membrane coated with a layer of ECMatrix™. Briefly, after detaching with cell dissociation solution (Sigma), CCL-222 cells were cultured in suspension in RPMI-1640 with 10% FBS for 2 hours. Then, the cells were resuspended in serum free RPMI-1640, and $5\times10^4$ cells were seeded into the ECM layer which had been previously rehydrated at room temperature for 1-2 hours. For the plasmin-dependent invasion assay, 0.2 μM of plasminogen was added to the cell suspensions. 150 μl of RPMI-1640 media containing 10% fetal bovine serum was added the lower chamber as chemoattractant. Cells were incubated for 24 hours at 37° C. in a $CO_2$ incubator (5% $CO_2$). Invaded cells on the bottom of the insert membrane were dissociated from the membrane by incubation with cell detachment buffer and subsequently lysed and detected by CyQuant GR dye. The fluorescence was quantified with a fluorescence plate reader using a 485/535 nm filter set.

Chamber migration assay—Migration was evaluated using a modified Boyden chamber assay. 8 m cell culture inserts contain PET (polyethylene tetrephthalate) (BD Biosciences) were placed within a 24-well chamber containing 0.8 ml RPMI-1640 medium with 10% FBS. $1.5\times10^5$ cells were seeded into the inserts suspended in 0.3 ml of serum free RPMI-1640 media with 0.2 μM of plasminogen. After incubation for 24 hours at 37° C. in a $CO_2$ incubator (5% $CO_2$), the upper surface of the filter was scraped to remove nonmigratory cells. Migrated cells were fixed with 4% PFA and stained with crystal violet. For quantification, the average number of migrating cells per field was assessed by counting 10 random fields under a light microscope (400×). Data indicate the mean obtained from three separate chambers.

Miscellaneous techniques—Protein concentrations were determined using Coomassie Brilliant Blue, and BSA standards as described by Bradford (Bradford, M. M. (1976) *Analytical Biochemistry* 72, 248-254). All reagents used were of analytical grade or better. Data was analyzed using Sigma Plot (Jandel Scientific).

Results

It was observed that Colo 222 colorectal cells express extracellular p11 but not annexin A2.

Figure 17:
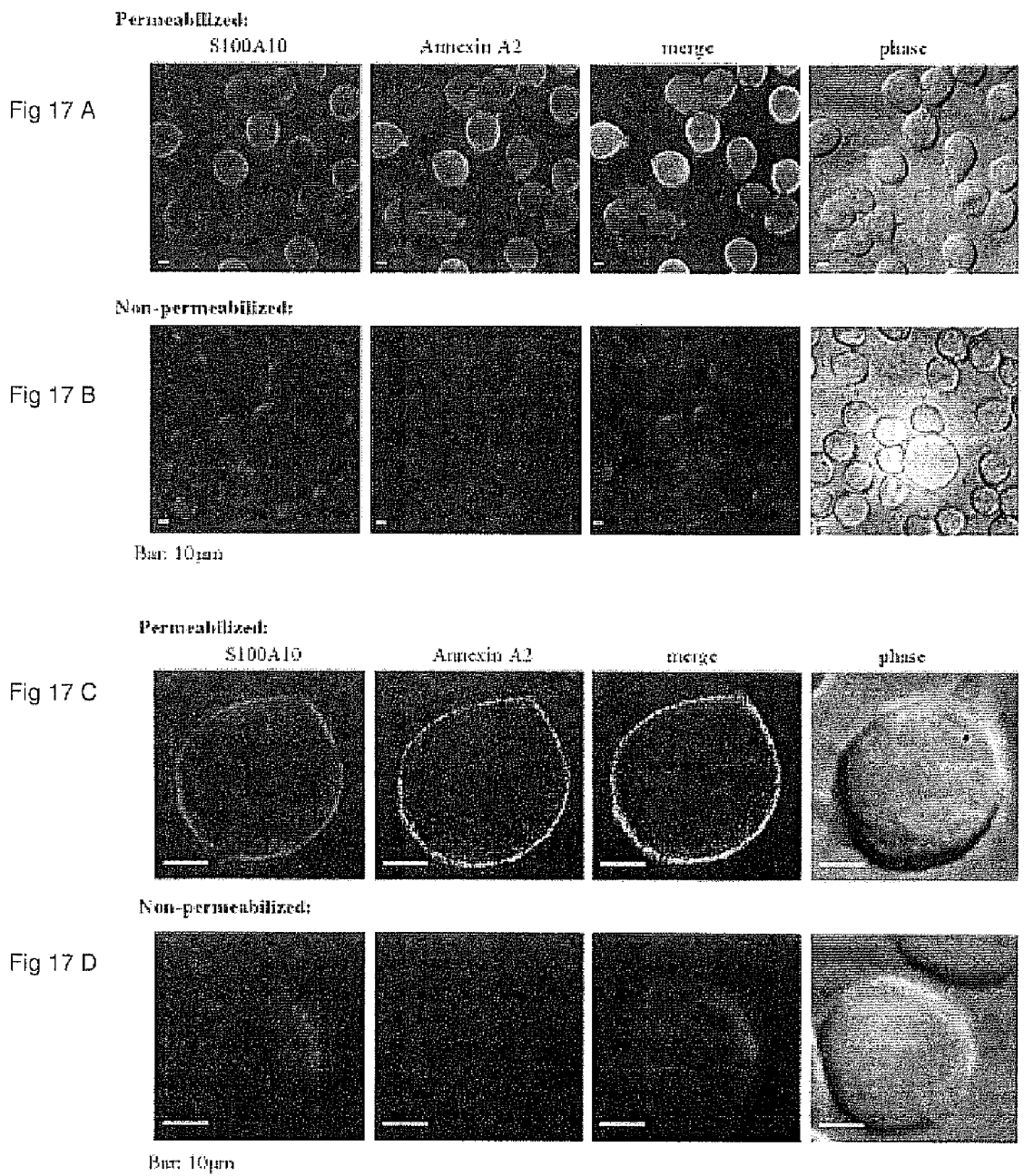
FIG. 17. Immunofluorescence localization of S100A10 in CCL-222 colorectal cells. Permeabilized (A) or non-permeabilized (B) CCL-222 colorectal cells were treated with anti-S100A10 monoclonal and anti-annexin A2 polyclonal antibodies followed by Alexa-labeled (green) and Cy3-labeled (red) secondary antibodies. The nucleus was also stained with DAPI. (blue). Yellow fluorescence indicates colocalization of these proteins. Staining of permeabilized cells revealed an intense colocalization of S100A10 and annexin A2 in the submembraneous region (A). As shown in B, immunofluorescence staining of non-permeabilized cells reveals the presence of S100A10 in discrete patches on the cell surface, whereas annexin A2 was not detectable on the cell surface. Immunofluorescence staining was also performed at higher magnification by confocal microscopy (C, D). At this higher magnification, the intense colocalization of S100A10 and annexin A2 in the submembranous region is readily observed (C). In the non-permeabilized cells, the patch of S100A10 at the cell surface appears diffuse and non-uniform (D). Normal mouse and goat IgG (isotype-matched) were used as controls to represent background fluorescence (not shown). Scale bar represents 10 μm. E, detection of extracellular S100A10 by cell surface biotinylation. CCL-222 cell surface proteins were biotinylated using membrane-impermeable sulfo-NHS-biotin. Biotinylated proteins were pelleted with streptavidin-conjugated Dynabeads, loaded on 12% SDS-PAGE and analyzed by Western blotting with both monoclonal S100A10 and monoclonal annexin A2 antibody.
Figure 17:
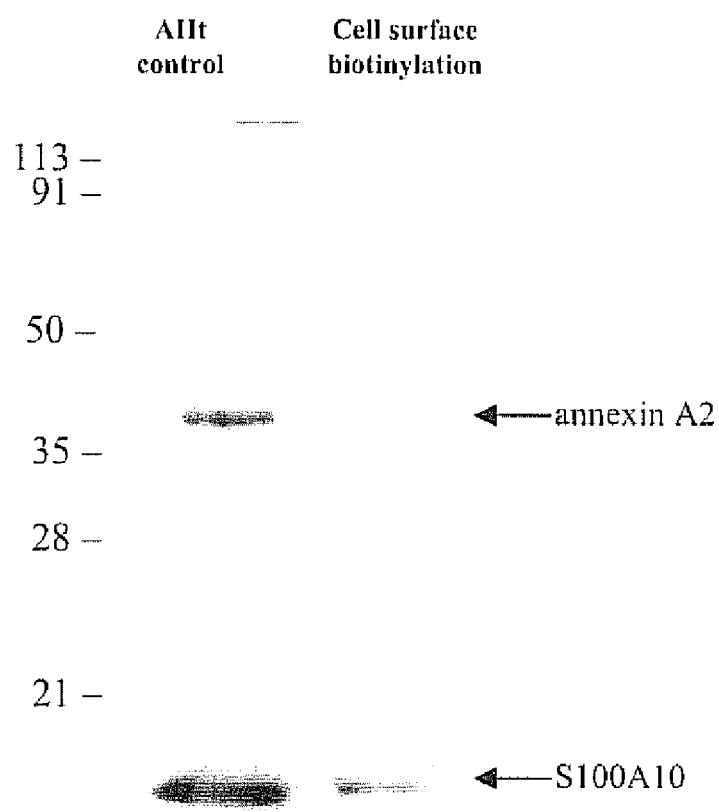

The CCL-222 cell line is a human intestinal tumour cell line that forms liver micrometastases in nude mice. To investigate the intracellular distribution of S100A10 and annexin A2, the colorectal cells were permeabilized and simultaneously stained for both p11 and annexin A2. As shown in FIG. 17A, immunofluorescence microscopic analysis established the presence of both p11 (a.k.a. S100A10) and its ligand annexin A2 within these cells. The distribution of p11 and annexin A2 immunofluorescence was consistent with the majority of these proteins colocalizing at the submembranous region of the cell. Confocal microscopy also confirmed that the majority of intracellular p11 and annexin A2 colocalized at the plasma membrane (FIG. 17C).

Next, the immunofluorescence distribution of p11 and annexin A2 was examined in non-permeabilized colorectal cells (FIG. 17B, D). p11 was observed to be present in discrete patches on the cell surface similar to structures observed for this protein on the extracellular surface of breast carcinoma, HT1080 fibrosarcoma, glioma and HUVEC cells (Mai et al. (2000); Choi et al., (2003); Kang et al. (1999) *Trends. Cardiovasc. Med.* 9, 92-102). Surprisingly, immunofluorescence staining for annexin A2 was not observed, suggesting that annexin A2 was not present on the extracellular surface. Since the anti-annexin A2 antibody easily detected intracellular annexin A2, the inability to detect extracellular annexin A2 was not due to a problem with antibody reactivity.

In order to confirm the absence of annexin A2 from the cell surface, cell surface proteins were biotinylated and isolated by avidin-Sepharose pull-down. The biotinylated protein fraction was analysed by Western blotting. As shown in FIG. 17E, only p11 and not annexin A2 was detected in the biotinylated protein fraction. Thus, both immunofluorescence microscopy and surface biotinylation suggested that annexin A2 was not present on the surface of the colorectal cells. The absence of annexin A2 from the extracellular surface was unexpected because typically both p11 and its binding partner, annexin A2, are found on the extracellular surface as the heterotetrameric complex, AIIt (Yeatman et al. (1993; Kassam et al. (1998); Mai et al. (2000); Choi et al. (2003)). The absence of annexin A2 from the extracellular surface presented the opportunity to examine the role of p11 in plasminogen regulation in the absence of its annexin A2 binding partner.

It was observed that p11 colocalizes with uPAR.

The conversion of the inactive zymogen, plasminogen to the broad specificity protease, plasmin, is mediated at the cell surface by the action of the urokinase plasminogen activator, uPA (reviewed in Ploug, M. (2003) Curr. Pharm. Des 9, 1499-1528; Sidenius, N. and Blasi, F. (2003) Cancer Metastasis Rev. 22, 205-222; Blasi, F. and Carmeliet, P. (2002) Nat. Rev. Mol. Cell Biol. 3, 932-943; Kjoller, L. (2002) Biol. Chem. 383, 5-19; Preissner et al (2000) Curr. Opin. Cell Biol. 12, 621-628; Mondino et al (1999) Thromb. Haemost. 82 Suppl 1, 19-22). Both plasminogen and uPA interact with specific cell-surface receptors: plasminogen binds to receptors such as S100A10 (Kassam et al. (1998a); Kassam et al. (1998b); Fitzpatrick et al. (2000) Biochemistry 39, 1021-1028), cytokeratin-8 (Hembrough et al. (1995) J. Cell Sci. 108, 1071-1082; Hembrough et al. (1996) J. Biol. Chem. 271, 25684-25691; Kralovich et al (1998) J. Protein Chem. 17, 845-854) TIP49a (Hawley et al. (2001) J Biol Chem 276, 179-186) and α-enolase (Miles et al. (1991) Biochemistry 30, 1682-1691; Redlitz, A. and Plow, E. F. (1995) Baillieres. Clin. Haematol. 8, 313-327; Pancholi, V. (2001) Cell Mol. Life Sci. 58, 902-920) while uPA binds to its receptor, uPAR. As shown in FIG. 18A, p11 and uPAR share a similar distribution on the cell surface and appear to localize to one or two distinct regions of the cell surface. Confocal microscopy also confirmed the similar distribution of these proteins although the distribution of p11 appeared to be more restricted than that of uPAR (FIG. 18B). At high magnification p11 and uPAR appear to colocalize in some regions of the cell surface (FIG. 18C). Interestingly, the majority of plasminogen binding sites were observed to be at the cell surface colocalized with uPAR (FIG. 18D). Collectively, these results suggest the presence of p11, uPAR and plasminogen at a common locus on the extracellular surface.

The p11 gene was silenced by RNA interference.

Figure 19E:
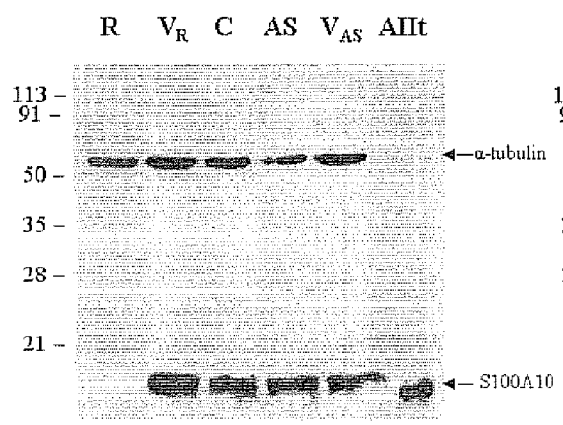
FIG. 19. S100A10 gene silencing by siRNA. CCL-222 cells were transfected with the pSUPER-S100A10 or pSUPER-Con. After transfection, cells were selected with puromycin. For immunofluorescence staining, cells were permeabilized and stained for S100A10 and annexin A2 (A, B). C, D, S100A10 was incubated with the SIR6 clone overnight. After washing 3 times with D-PBS, cells were fixed and stained for S100A10. Staining was performed for both non-permeabilized (C) and permeabilized cells. (D). Relative S100A10 and annexin A2 expression levels were determined by Western blot analysis (E, F). Cells were lysed with RIPA lysis buffer, separated on SDS-PAGE and blotted with a monoclonal S100A10 and polyclonal annexin A2 antibody. Detection of—tubulin was used as a loading control. R, pSUPER-S100A10 stable transfectants selected with puromycin; $V_R$: cells transfected with pSUPER-Con and selected with puromycin; C: parental CCl-222 cells; AS: cells transfected with pLIN vector containing full length antisense to S100A10 and selected with G418; $V_{AS}$: cell transfected with pLIN vector containing no insert and selected with G418. AIIt standard is also shown.
Figure 19F:
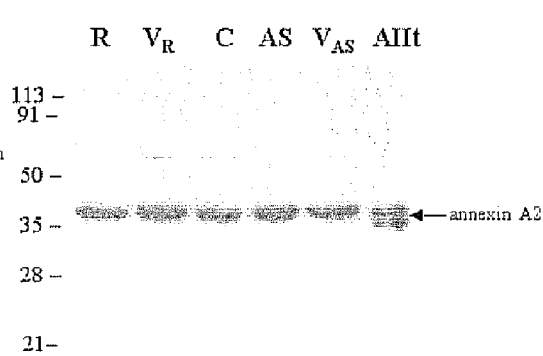

To study the role of p11 in plasminogen regulation, the pSUPER system was used to stably suppress the expression of the p11 gene. The pSUPER construct used in this example consists of a H1-RNA promoter cloned next to the 19 nucleotide p11 sequence (nucleotides 199-217; SEQ ID NO:22) separated by a short 9 nucleotide spacer (SEQ ID NO:23) which forms the hairpin, followed by the reverse compliment of the same nucleotide sequence (SEQ ID NO:24). The pSUPER-Con vector, was identical to the pSUPER-S100A10 vector except the 19 nucleotide sequence was derived from an irrelevant nucleotide sequence. CCL-22 colorectal cells were transfected with the pSUPER-S100A10 or pSUPER-Con and cells were selected with puromycin and cultured under these conditions for about a month. As shown in FIG. 19, both immunofluorescence microscopic analysis (FIG. 19A-D) and Western blotting (FIG. 19E,F) showed that the p11 levels are reduced in the pSUPER-S100A10 cells compared to the pSUPER-Con cells. Furthermore, the annexin A2 levels were not affected by the p11 knockdown, establishing the specificity of the action of the S100A10 siRNA (FIG. 19F). As described herein (supra), the pLIN vector was used to stably transfect HT1080 fibrosarcoma cells with a full length antisense cDNA to p11 (see also Choi et al. (2003)). It was interesting to note that this antisense strategy was unsuccessful in the CCL222 cells. Although transfection of CCL 222 cells with the pLIN-S100A10 vector resulted in stable G418-resistant cells, as shown in FIG. 19E, the p11 protein levels were unchanged.

Next, the pSUPER-S100A10 cells were cloned and analysed for p11 levels. As shown in FIG. 20A, when analysed after 2 months of culture it was observed that several pSUPER-S100A10 transfected clonal cell lines maintained a significant reduction in p11 protein levels compared to the pSUPER-Con transfected cells. Furthermore, the protein levels of uPAR and annexin A2 were unaffected by the transfections of pSUPER-S100A10 or pSUPER-Con.

Of the three established cell lines, clone SIR6 showed the lowest total cellular levels of p11. Therefore, clone SIR6 was chosen for further analysis. The affect of the siRNA on the p11 mRNA levels was examined. As shown in FIG. 20B, p11 mRNA levels of SIR6 were reduced as compared to the pSUPER-Con cells or parental cells. Furthermore, the annexin A2 mRNA levels were unchanged. This indicated that the siRNA approach was specific and loss of p11 mRNA or p11 protein levels did not affect the mRNA or protein levels of its intracellular binding partner, annexin A2. Second, an analysis by immunofluorescence microscopy of the distribution of p11 was performed. It was observed that the cellular levels of p11 were diminished but not totally eliminated. Furthermore, when purified recombinant p11 was incubated with the SIR6 clone, it bound to the cell surface and demonstrated a distribution that was similar to the staining pattern observed for endogenous extracellular p11 (FIG. 19C).

Modulation of plasmin formation is modulated by p11:

The effect of altered extracellular levels on the ability of the cells to convert plasminogen to plasmin was examined. CCL222 cells, like many cancer cells, constitutively secrete uPA, which functions as a plasminogen activator. Cellular plasmin formation was monitored by washing the cells with serum-free media and measuring the initial rates of plasmin formation after addition of plasminogen and a colorimetric plasmin substrate. The activity of the CCL222 cells that had been transfected with either pSUPER-S100A10 or pSUPER-Con and selected with puromycin but had not been subjected to clonal selection were compared. As shown in FIG. 21A, the pSUPER-S100A10 transfected cell population that had not been cloned showed a loss of about 35% of their plasmin generating capability. By comparison, about 65% of the plasmin generating activity of the SIR6 cell line was lost compared to the pSUPER-Con cell line. Furthermore, addition of purified recombinant p11 to the SIR6 cell line restored plasmin production. The 65% loss in plasmin generation by the SIR6 cells was maintained irrespective of the time of incubation of cells with plasminogen (FIG. 21B).

Figure 21C:
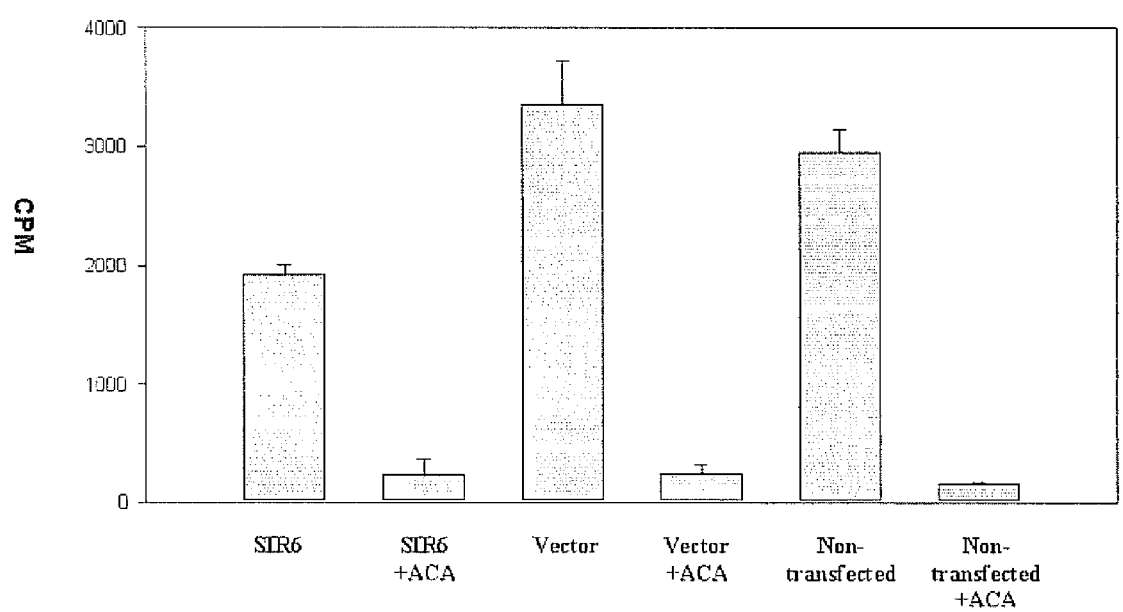
FIG. 21. Regulation of plasminogen binding and activation by S100A10. Plasminogen activation was studied in parental CCL-222 cells and two transfectants with pSUPER-S100A10 or pSUPER-Con. Plasmin generation was also quantitated in the presence or absence of 0.5 μM [Glu]-Plasminogen. Conditioned media was collected from different cell lines at different times and cell-generated plasmin was measured at 405 nm with the amidolytic plasmin substrate H-D-norleucyl-hexahydrotyrosyl-lysine-p-nitroanilide after 2 hours A, plasmin generation was examined for the pSUPER-S100A10 transfectants selected with puromycin but not cloned (RNAi pre-cloning), cells transfected with the pSUPER-Con vector and selected with puromycin (Vector) and the SIR6 clonal cell line (SIR6). Alternatively, SIR6 cells were preincubated with S100A10 (0.5 μM), washed, incubated with plasminogen, and plasmin activity of the conditioned media was examined (siR6+S100A10). Parental cells (Non-transfected) were also examined. B, Time-course of plasmin generation by SIR6 clonal cell line in the presence or absence of 0.5 μM plasminogen. The vector control cells and parental cells were also included in the analysis. C, plasminogen binding to SIR6 cells and vector control cells was examined with $I^{125}$-labelled plasminogen. Plasminogen binding in the presence of ε-ACA is included as a specificity control.

The binding of plasminogen to cells involves the interaction of the lysine-binding kringle domains of plasminogen with the carboxy-terminal lysines of plasminogen receptors. This binding interaction can be inhibited by lysine analogues such as ε-aminocaproic acid (ε-ACA), which competes for the lysine-binding kringle domains of plasminogen. In order to examine if changes in the extracellular levels of p11 corresponded to changes in the plasminogen binding capacity of the CCL-222 cells, the SIR6 cell line was incubated with $I^{125}$-labelled plasminogen and, after washing the cells with buffer, the levels of bound plasminogen was determined. As shown in FIG. 21C, the SIR6 clone showed a 45% loss of specific plasminogen binding compared to the vector control cells. Plasminogen binding to all cell lines was abrogated by ε-ACA treatment.

p11 has a role in the invasiveness of CCL222 cells:

The invasion of cancer cells through the extracellular matrix involves both the activation of cell surface proteases as well as changes in cell motility. A Matrigel assay system was employed to study the invasiveness of the colorectal cells. The cells were seeded in the upper chamber of an ECM™ invasion assay chamber and the number of cells that transversed the Matrigel-coated membrane and appeared in the lower chamber was determined using the fluorescent CyQuant dye. When the experiment was performed in the absence of plasminogen, the invasiveness of the SIR6, vector control and untransfected cells were similar (FIG. 22A). In contrast, it was observed that in the presence of plasminogen, the invasiveness of the pSUPER-p11 cells was decreased by 38% compared to the vector control cells. Interestingly, the SIR6 cells showed a complete loss of plasminogen-dependent invasiveness.

Changes in the invasiveness of the CCL-222 cells could be due to changes in the cell-surface proteolytic activity or motility of the cells or both. The motility of the cell lines was examined by determination of their migration through the polyethylene filter in the absence of Matrigel. As shown in FIG. 22B, all the clones had similar migration rates indicating that observed changes in cellular invasiveness was not due to differences in cellular motility.

EXAMPLE 12

The Role of p11 in Matrix Metalloproteinase ("MMP") Activity

Review and Summary

Figure 23:
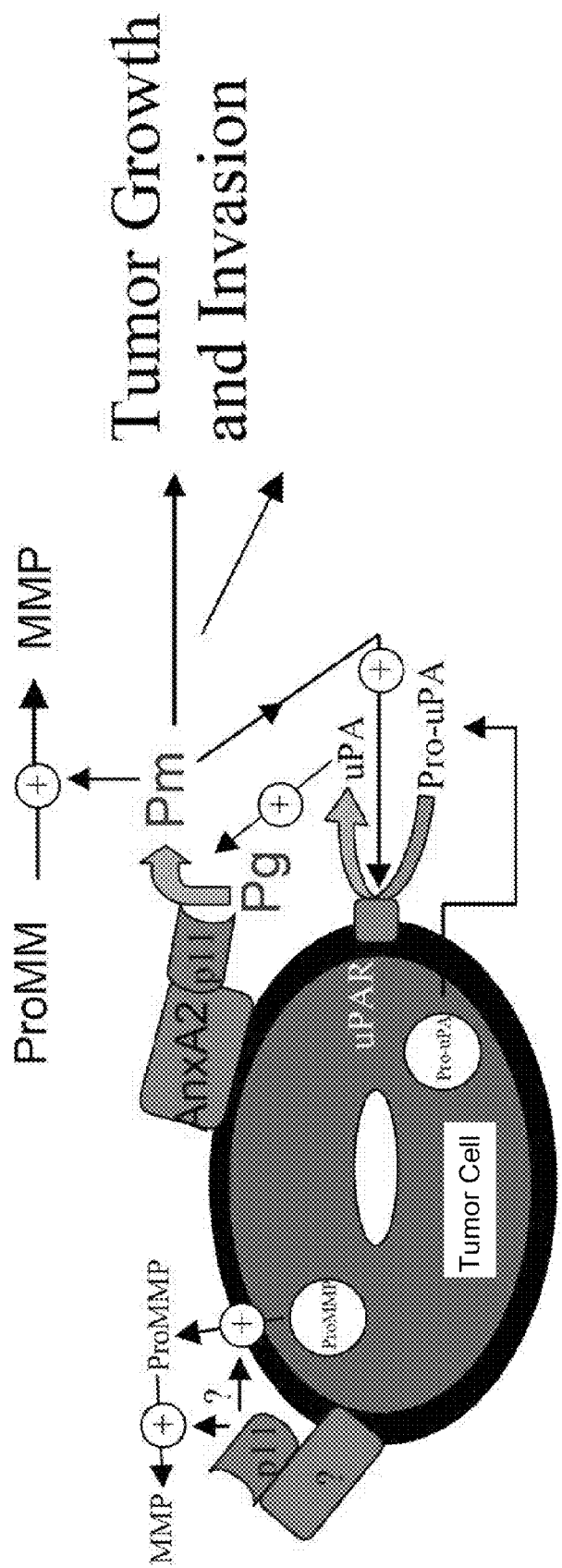
FIG. 23: Experimental model of the regulation of cell surface protease activity by p11. p11 binds Pg and Pm and stimulates cellular Pm production. p11 is anchored to the membrane via annexin A2 (HT1080 cells) or via an unknown mechanism (colorectal cells). p11 also regulates the release of MMPs into the media. The p11-plasmin complex may also activate proMMPs.

A defining characteristic of a tumor cell is its ability to escape the constraints imposed by neighboring cells, invade the surrounding tissue and metastasize to distant sites. This invasive property of tumor cells is dependent on activation of proteinases at the cell surface. The two major families of enzymes that participate in the pericellular proteolysis and play a fundamental role in tumor cell invasiveness are the plasminogen and matrix metalloproteinases (MMPs) families of proteinases. As described herein (supra), the p11 knock-down HT1080 cells failed to form tumors in SCID mice. Since plasminogen knock-out mice are capable of growing tumors, it is likely that in addition to plasmin, other proteinases are required for tumor formation. This presented the possibility that p11 might be involved in the other physiological processes related to tumor growth and metastasis, the most obvious of which being the regulation of other proteases. It was further discovered that the extracellular levels of gelatinases produced by the instant p11 knock-down HT1080 and colorectal cancer cells were substantially decreased. This observation suggests that p11 may play a role in the regulation of levels and activity of certain MMPs and also provides a potential explanation of why p11 knock-down HT1080 cells did not form tumors (supra). Furthermore, it was discovered that p11 binds plasmin and cathepsin B and some observations suggest that p11 interacts with EMMPRIN. Based on these observations, the inventors put forth herein the reasonable hypothesis that p11 functions to regulate cell surface plasmin and MMP activity and also acts as a docking protein to localize proteinases to the cell surface (FIG. 23). By these mechanisms, p11 plays a role in cancer cell invasiveness and metastasis.

Molecular Interactions of p11, p36 and AIIt

More recently, we used to observe, in real time, the molecular interactions between phospholipid-associated ANXA2 (a.k.a. p36), p11 and AIIt and the ligands, t-PA, plasminogen and plasmin were observed using surface plasmon resonance (SPR) (see also MacLeod et al. (2003) J Biol Chem 278: 25577-25584, which is herein incorporated in its entirety by reference). It was observed that AIIt bound to t-PA ($K_d$ 0.68 µM), plasminogen ($K_d$ 0.11 µM) and plasmin ($K_d$ 0.75 µM) with moderate affinity. Contrary to previous reports, the phospholipid-associated annexin A2 failed to bind to t-PA or plasminogen, but bound plasmin ($K_d$ 0.78 µM). However, p11 bound to t-PA ($K_d$ 0.45 µM), plasminogen ($K_d$ 1.81 µM) and plasmin ($K_d$ 0.36 µM). Removal of the carboxyl-terminal lysines from p11 attenuated t-PA and plasminogen binding to AIIt. These observations unambiguously establish that p11 is a plasminogen receptor and that the carboxyl-terminal lysines of p11 form the t-PA and plasminogen binding sites.

Identification of p11 as a Docking Protein for Extracellular Proteinases

The plasma membrane is known to contain microdomains commonly referred to as lipid rafts. Membrane rafts at steady state are small and highly dispersed but certain stimulatory events or the development of a polarized cell type result in the clustering of the membrane rafts into large, clearly visible domains. These coalesced microdomains contain GPI-proteins, such as the uPA receptor, uPAR, along with glycosphingolipids (particularly GM1 and GM3) and cholesterol. EMMPRIN and CD44 are examples of transmembrane proteins that are also known to be present in the lipid raft microdomains (Gomez-Mouton et al. (2001) PNAS USA 98:9642-9647; Harder, T. and K. Simons (1997) Curr Opin Cell Biol. 9:534-542; Manes et al. (1999) EMBO J. 18:6211-6220; Staffler et al. (2003) J Immunol 171:1707-1714; Waugh et al. (2001) Biochem Soc Trans 29:509-511).

Figure 24:
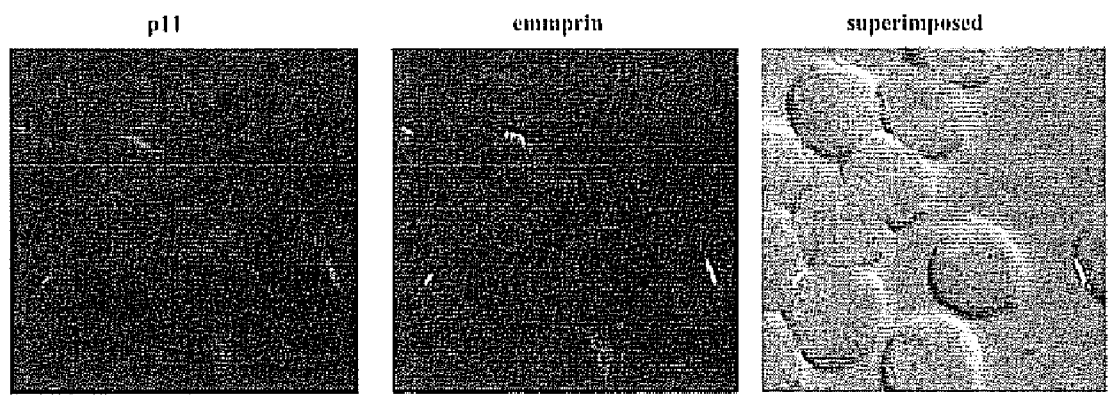
FIG. 24. Colocalization of p11 and emmprin on the CCL-222 cell surface. Cells grown on glass coverslips were fixed with 4% Paraformaldehyde (PFA) and stained for both p11 and emmprin using anti-p11 monoclonal antibody and anti-emmprin goat polyclonal antibody, followed by Cy-3-labeled rabbit anti-mouse and Alexa-labeled donkey anti-goat secondary antibodies. The fluorescence and DIC images of the same area are superimposed and yellow indicates colocalization. The images were taken by confocal microscope and deconvolved. Lower panel-BSA, anxA2 or p11 was coupled to Dynabeads and incubated with colorectal cells. Beads were washed and bound proteins eluted with SDS PAGE sample buffer and Western blots analyzed with EMMPRIN antibody.
Figure 24:
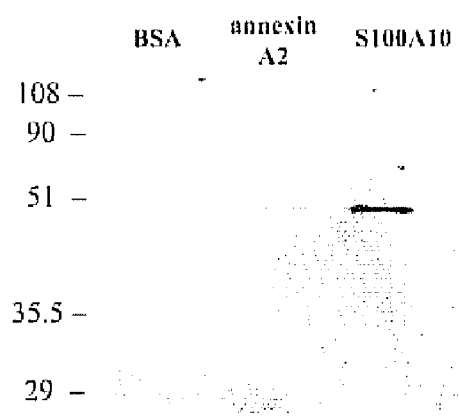

The first clue that p11 might be part of a "proteolytic hub"—a specialized, cell surface raft microdomain where proteinases and their substrates could assemble, was the observation made by the inventor that p11 was not distributed homogeneously on the plasma membrane but was present in discrete patches with only a few of these structures present at the cell surface (Kassam et al. (1998a) J Biol Chem 273:4790-4799). Subsequently, the inventor had observed that p11 colocalized with uPAR (Choi et al. (2003) FASEB J 17:235-246). Since it was observed that p11 does not bind uPAR (MacLeod et al. (2003) J Biol Chem 278:25577-25584), it is reasonably apparent that uPAR and p11 are independently targeted to the proteolytic hub. It was also observed that EMMPRIN and p11 in these discrete patches at the surface of colorectal cancer cells (FIG. 24). It was also observed that CD44 and p11 colocalize in the proteolytic hub of colorectal cancer cells, which also has been reported by another research group (Oliferenko et al. (1999) J. Cell Biol. 146:843-854). Therefore, instant observation that p11 colocalizes with known membrane lipid raft microdomain proteins such as uPAR and EMMPRIN is consistent with the reasonable hypothesis that p11 is part of a proteolytic hub. The instant observation that loss of p11 from the cell surface does not disrupt the distribution of uPAR or EMMPRIN, suggests that p11 is not involved in the formation or maintenance of the microdomains. Interestingly, the p11-containing patches are sites of active proteolysis. It is reasonable to expect that the colocalization of p11 with EMMPRIN also presents a probable link between the uPA/plasminogen proteinase system and the MMPs proteinase system.

The observations herein disclosed provide a clue to the function of p11 within the proteolytic hub. The first indication that p11 might function in the proteolytic hub as a docking protein for other proteins was our report that p11 bound tPA, plasminogen and plasmin (MacLeod et al. (2003) J Biol Chem 278:25577-25584). It was also observed that the major plasminogen-binding site on colorectal cancer cells corresponded with the uPAR/p11-containing proteolytic hub (supra and Zhang et al. (2003) J Biol Chem epublished October 20, which is herein incorporated by reference). This suggested that the proteolytic hub represented the region of the cell surface that was a major site for the conversion of plasminogen to plasmin. It was also observed that p11 colocalized with and directly bound to cathepsin B, a cysteine proteinase known to be upregulated in a variety of tumors and implicated in the progression of human tumors (Mai, J., D. M. Waisman, and B. F. Sloane (2000) Biochim Biophys Acta 1477:215-230). Thus, two proteinases (plasmin and cathepsin B) and one proteinase substrate (plasminogen) have been identified that bind to p11 within the proteolytic hub.

Significance of the EMMPRIN-p11 Colocalization Observation

Matrix metalloproteinases (MMPs) are secreted by mammalian cells as zymogens and upon activation, initiate tissue remodeling by proteolytic degradation of collagens and proteoglycans. Activation of the secreted proenzymes and interaction with their specific inhibitors determine the net enzymatic activity in the extracellular space. MMPs play a major role in tumor invasion by remodeling the extracellular matrix, activating growth factors and cytokines, and degrading serine proteinase inhibitors (Gabison et al. (2003) Pathol Biol (Paris) 51:161-166; Li, Y. Y., C. F. McTiernan, and A. M. Feldman (2000) Cardiovasc Res 46:214-224; Pepper, M. S. (2001). Arterioscler Thromb Vasc Biol 21:1104-1117; Sato et al. (1997) Thromb Haemost 78:497-500. High levels of MMPs are a hallmark of many human tumor types including breast, colorectal, ovarian and lung (Curran, S, and G. I. Murray (2000) Eur J Cancer 36:1621-1630). The production of MMPs is the result of a collaboration between tumor and stromal cells with most MMPs produced by stromal cells within human tumors (Gray, S. T., R. J. Wilkins, and K. Yun (1992) Am J Pathol 141:301-306; Gray et al. (1993) Am J Pathol 143:663-671; Hiraoka et al. (1992) Biochem Int 27:1083-1091; Poulsom et al. (1992) Am J Pathol 141:389-396). Previous studies have described several types of host/tumor cell interactions that either mediate or augment tumor invasion by MMPs. These include secretion of MMPs by stromal cells in response to stimulation by tumor cells or, conversely, induction of MMP production by the tumor cells in response to host stimuli. Some of these mechanisms require direct contact between the stromal and tumor cells, whereas others do not. The increase can occur at a pretranslational level, and in most instances, conditioned medium from macrophages or fibroblasts is an effective inducer (Benbow et al. (1999) J Biol Chem 274:25371-25378; Kataoka et al. (1993) Cancer Res 53:3154-3158).

Tumor cell-derived collagenase stimulatory factor, renamed extracellular matrix metalloproteinase inducer (EMMPRIN), is a $M_r$ 58 kDa, type I transmembrane glycoprotein belonging to the Ig superfamily (Kasinrerk et al. (1992) J Immunol 149:847-854). EMMPRIN is located on the surface of human tumor cells and functions to trigger the production or release of matrix metalloproteinases such as MMP-1, MMP-2, and MMP-3 to the surrounding mesenchymal cells and tumor cells, thereby contributing to tumor invasion (Guo et al. (1998) Gene 220:99-108; Guo et al. (1997) J Biol Chem 272:24-27; Kataoka et al. (1993) Cancer Res 53:3154-3158; Li et al. (2001) J Cell Physiol 186:371-379). Interestingly, EMMPRIN-transfected tumor cells produce significantly more latent and active MMP-2 and MMP-3 than vector-transfected tumor cells (Caudroy et al. (2002) Clin Exp Metastasis 19:697-702). Thus, EMMPRIN acts both as an autocrine factor stimulating MMP production in tumor cells and as a paracrine factor stimulating MMP production in mesenchymal cells. In addition to a role as a MMP stimulatory factor, EMMPRIN also may bind MMPs at the cell surface suggesting a role for this protein in the localization of cellular proteinases. The binding of MMP-1 to EMMPRIN has been clearly demonstrated (Guo et al. (2000) Cancer Res. 60:888-891). MMP-1 plays a key role in tumor cell invasiveness and for the penetration of fibrous tissues by tumor cells because of the ability of MMP-1 (unlike other MMPs) to degrade fibrillar (type I) collagen. The formation of EMMPRIN-MMP-1 and p11-plasmin/cathepsin B complexes in the proteolytic hub is reasonably expected to allow more efficient proteolysis of the ECM components by these proteinases.

Figure 25:
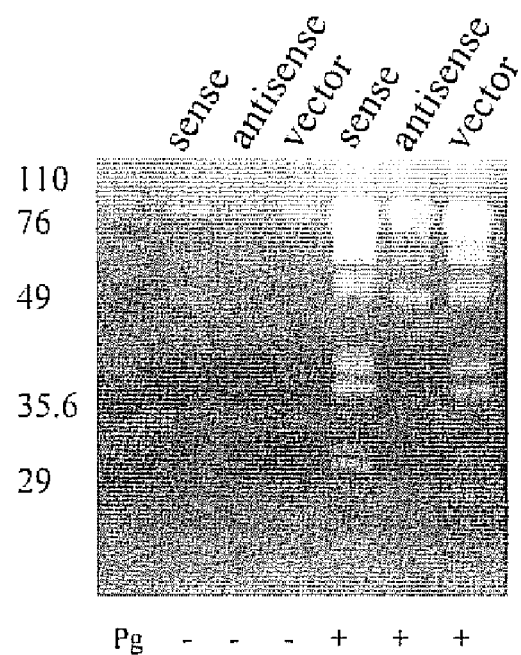
FIG. 25. Top—The MMP activity of S7 (sense p11), AS5 (antisense p11), and Vec-1 conditioned media from transfected HT1080 cells was measured by gelatin zymography. Bottom, gelatin zymography of colorectal cancer cells incubated in the absence of plasminogen. 1. Vector transfected; 2. Vector cells treated with aprotinin (2.2 μM); 3. p11 RNAi; 4. p11 RNAi transfected cells treated with 0.5 μM p11; 5. RNAi transfected cells treated with 0.5 μM p11 and 2.2 μM aprotinin.
Figure 25:
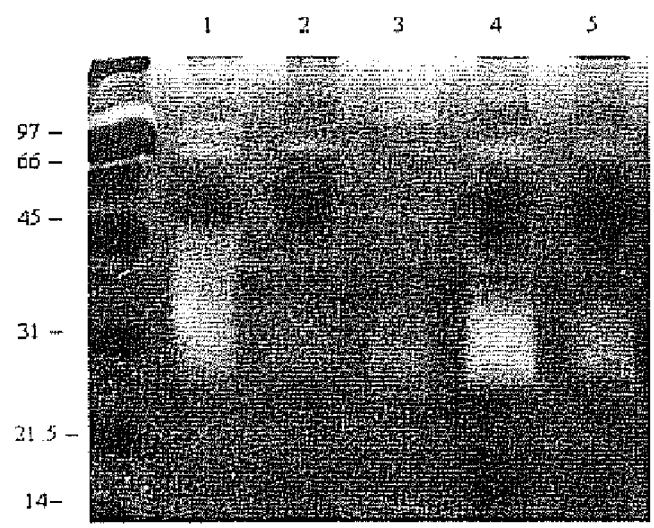
Figure 26:
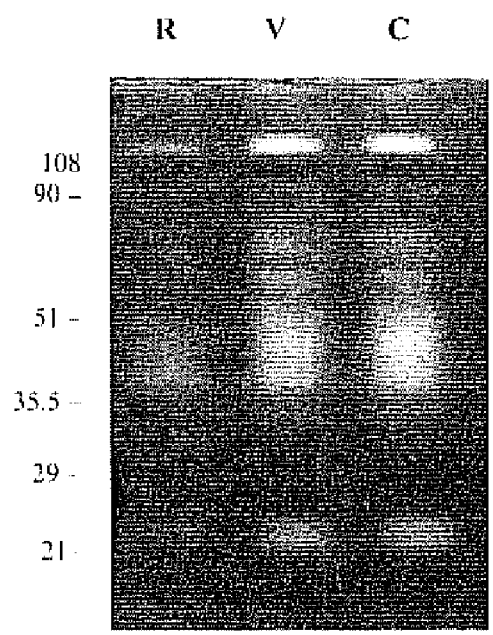
FIG. 26. Gelatin zymography of colorectal cancer cells (CCL-222) grown in the presence of human foreskin fibroblast monolayer (HFF). Cells were cultured in the presence or absence of plasminogen and conditioned media collected. R, siRNA transfected; V, vector control transfected; C, untransfected.
Figure 26:
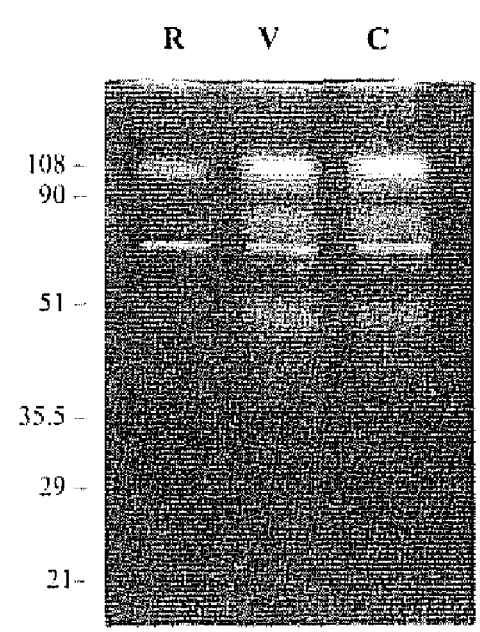

The Proteolytic Hub as a Major Site for Activation and Accumulation of Proteinases The instant p11-knock-down HT1080 fibrosarcoma and colorectal cancer cells (supra) additionally provide a useful model to begin to understand the potential role of p11 in the regulation of proteinase activity. As discussed above, the p11 knock-down HT1080 cells show dramatically reduced plasmin production and a loss of uPA production. Presumably this loss in reciprocal zymogen activation results from a loss in the association of the p11-plasmin(ogen)/pro-uPA-uPAR complexes. It was also observed that p11 knock-down colorectal cancer cells (supra) show both a reduction in plasmin generation activity and attenuation of gelatinase activity (FIG. 25).

Although other proteinases can be detected by zymography, gelatin zymography is an extremely sensitive technique to measure MMP activity with MMP-9 and MMP-2 most easily detected. MMP-1 is poorly detected by gelatin or casein zymography while MMP-3 is detected by casein zymography. Typically, the MMPs are secreted by cells as stable, inactive zymogens, pro-MMPs, and require activation for catalytic function. Interestingly, several MMPs can be activated by plasmin. In vitro, plasmin directly activates proMMP-1, proMMP-3, proMMP-9, proMMP-10 and proMMP-13 (Carmeliet et al. (1997) Nat Genet. 17:439-444; Davis et al. (2001) J Cell Sci. 114:917-930; Eeckhout, Y. and G. Vaes (1977) Biochem J 166:21-31; Goldberg et al. (1990) Ann N.Y. Acad Sci 580:375-384; Grant et al. (1992) Matrix Suppl 1:217-223; Hahn-Dantona, et al. (1999) Ann. N.Y. Acad. Sci. 878:372-387; He et al. (1989) PNAS USA 86:2632-2636; Legrand et al. (2001) Exp Cell Res 264:326-336; Okada et al. (1992b) J Biol Chem 267:21712-21719; Ramos-DeSimone et al. (1999) J Biol Chem 274:13066-13076; Suzuki et al. (1990) Biochemistry 29:10261-10270). Activation of proMMP-2 involves hydrolysis by MT1-MMP, yielding an intermediate that is activatable by plasmin (Baramova et al. (1997) FEBS Lett. 405:157-162; Monea et al. (2002) J Cell Physiol 192:160-170). Activation of proMMP-9 may occur via plasmin-dependent or plasmin-independent mechanisms (Davis et al. (2001) J Cell Sci. 114:917-930; Legrand et al. (2001) Exp Cell Res 264:326-336; Ramos-DeSimone et al. (1999) J Biol Chem 274:13066-13076). The addition of plasminogen to HT1080 cells causes the complete conversion of the intermediate MMP-2 form to the mature fully active form and also participates in the activation of MMP-9 (Baramova et al. (1997) FEBS Lett. 405:157-162; Mazzieri et al. (1997) EMBO J. 16:2319-2332). Thus, plasmin may play an important role in the in vivo activation of proMMPs.

Several active MMPs can further activate other proMMPs, thus constituting positive feedback mechanisms. MMP-3 can activate proMMP-9 (Ogata, Y., J. J. Enghild, and H. Nagase. (1992a) J Biol Chem 267:3581-3584), and MMP-3 and MMP-10 can superactivate procollagenase, generating collagenase with higher specific activity (He et al. (1989) PNAS USA 86:2632-2636; Suzuki et al. (1990) Biochemistry 29:10261-10270). MMP-3 and MMP-7 convert scu-PA to a lower molecular weight form and remove the u-PAR binding domains (Marcotte et al. (1992) J Biol Chem 267:13803-13806; Ugwu et al. (1998). Biochemistry 37:7231-7236). MMP-3 (Lijnen et al. (1998) Biochemistry 37:4699-4702), MMP-7 and MMP-9 (Patterson, B. C. and Q. A. Sang (1997) J Biol Chem 272:28823-28825) and MMP-12 (Dong et al.

(1997) Cell 88:801-810) cleave plasminogen thereby reducing available plasminogen for plasmin generation. Interestingly, the MMPs can also cleave inhibitors of plasmin generation or activity. For example, MMP-3 cleaves the plasminogen activator inhibitor, PAI-1 (Lijnen et al. (2000) J Biol Chem). Furthermore, MMP-3 hydrolyzes several sites in $alpha_2$-antiplasmin, the main physiological plasmin inhibitor (Lijnen, H. R., B. Van Hoef, and D. Collen (2001) Biochim. Biophys. Acta 1547:206-213). In terms of a physiological perspective, Ogata proposed that in colorectal tumor cells, uPA is coexpressed with proMMP-9. The uPA activates plasminogen and the resultant plasmin activates proMMP-3, which is then secreted. The secreted MMP-3 activates proMMP-9, resulting in colorectal cancer progression and metastasis (Inuzuka et al. (2000) J Surg Res 93:211-218).

CD44, the cell surface hyaluronan receptor, promotes tumor growth and metastasis by mechanisms that remain poorly understood (Cichy, J. and E. Pure (2003) J Cell Biol 161:839-843; Isacke, C. M. and H. Yarwood (2002) Int J Biochem Cell Biol 34:718-721; Jothy, S. (2003) Clin Exp Metastasis 20:195-201; Naor et al. (2002) Crit. Rev Clin Lab Sci 39:527-579; Ponta, H., L. Sherman, and P. A. Herrlich (2003) Nat Rev Mol Cell Biol 4:33-45; Yasuda et al. (2002) Histol Histopathol 17:945-950). CD44 is known to colocalize with uPAR (Laube, F. (2000) Anticancer Res. 20:5045-5048) and MT1-MMP (Mori et al. (2002) EMBO J. 21:3949-3959). MT1-MMP forms a complex with TIMP-1 and MMP-2. Activation of the latent proMMP-2 involves its binding to the cell surface MT1-MMP-TIMP-2 complex with subsequent cleavage of proMMP-2 by TIMP-2-free adjacent MT1-MMP. This is followed by autolytic maturation of the activation intermediate and the release of the mature MMP-2 species from cell surfaces into the extracellular milieu (Strongin et al. (1995) J Biol Chem 270:5331-5338; Zucker et al. (1998) J Biol Chem 273:1216-1222). CD44 also binds MMP-9 (Yu, Q. and I. Stamenkovic (1999) Genes Dev. 13:35-48; Yu, Q. and I. Stamenkovic (2000) Genes Dev. 14:163-176). Consistent with our model, MT1-MMP, MMP-2, uPAR, EMMPRIN and CD44 are all localized in lipid rafts on the cell surface (Annabi et al. (2001) Biochem J 353:547-553; Laube, F. (2000) Anticancer Res. 20:5045-5048; Oliferenko et al. (1999) J. Cell Biol. 146:843-854; Puyraimond et al. (2001) Exp Cell Res 262:28-36; Staffler et al. (2003) J Immunol 171:1707-1714; Stahl, A. and B. M. Mueller (1995) J Cell Biol 129: 335-344). Collectively these data support the concept of a proteolytic hub as a specialized lipid raft subdomain of the cell surface. Constituents of the proteolytic hub that can be reasonably inferred at this time from a variety of colocalization studies are p11, uPAR, EMMPRIN, CD44 and MT1-MMP.

Regulation of Cell Surface Proteinase Activity by p11

Dramatic differences in the gelatin zymography profiles of both the p11 knock-down HT1080 and colorectal cancer cells were observed (FIG. 25). Readdition of p11 to the p11 knock-down colorectal cancer cells restored the MMP levels to that of vector control cells (except for a single activity band). Clearly, the role of p11 in the regulation of the gelatinase activity is complex. For example the data presented in FIG. 25, right panel, examines the gelatinase profile of colorectal cells incubated in the absence of plasminogen. It was observed that the p11 knock-down resulted in the loss of some gelatinase activity bands and the appearance of others. Additional data suggests that MMP-2 (66-62 kDa band on FIG. 25) is decreased. It was also very interesting that the readdition of p11 to the p11 knock-down cells partially restored the gelatinase profile to that of the vector control. This suggests that the p11 may interact with membrane proteins and this may be responsible for the ability of p11 to regulate gelatinase activity. This data further provides evidence for the first time that p11 is involved in the regulation of MMP levels by both plasmin-independent and dependent mechanisms. The data presented in the left panel for the HT1080 cells also confirms a plasmin-independent effect of p11 on gelatinase activity. Here, preliminary evidence suggests that MMP-9 (arrow, FIG. 25) is affected by p11 knockdown. When these cells are incubated with plasminogen, the gelatinase profile is more complex and the effects of p11 on other MMPs and other proteases exhibiting gelatinase activity are evident.

This p11 effect could be due to an influence on transcription, translation or protein secretion. It is also possible that the p11-enhanced plasmin production, in addition to the binding of plasmin to p11 thus localizing it in proximity to other proteinases, could result in the regulation of proteinase activity. Our observation that p11 binds EMMPRIN presents the possibility that the effects of p11 on MMP levels could be mediated in part by EMMPRIN, a known MMP inducer. Interestingly, it was also observed by zymography that serine proteinase activity (aprotinin-sensitive activity) was also decreased in the p11 knock-down cells. This 30 kDa serine proteinase activity was neither plasmin nor trypsin (as determined by Western blot analysis). Thus, it is reasonably possible that in addition to regulating uPA and plasmin activity, p11 is involved in the regulation of MMPs and other unidentified serine proteinases.

Role of p11 in Cellular Tumor Formation, Invasiveness and Metastasis

Tumor formation and metastasis requires the dissolution of the extracellular matrix and basement membranes and this remodeling event is due in part to the activity of proteolytic enzymes. The MMPs and plasmin are arguably the most important proteinases implicated in tumor cell dissemination and ECM remodeling. By binding plasminogen to surface protein receptors and converting it to plasmin, the cell can harness an enzyme with broad substrate recognition to perform the local proteolytic events necessary for tumor growth, invasion and metastasis. Furthermore, as discussed above, plasmin can activate several of the MMPs thus enhancing the types of ECM substrates that can be cleaved.

As various changes could be made in the above methods and compositions without departing from the scope of the invention, it is intended that all matter contained in the above description and sequence listing, and shown in the accompanying drawings shall be interpreted as illustrative and not in a limiting sense.

All references cited in this specification are hereby incorporated by reference. The discussion of references herein is intended merely to summarize the assertions made by their authors and no admission is made that any reference constitutes prior art. Applicants reserve the right to challenge the accuracy and pertinence of the cited references.

What is claimed is:

1. A method of reducing the development of cancer, the method comprising administering to a cancer cell a therapeutically effective amount of a composition that modulates the activity of a p11 protein, wherein the composition comprises a small interfering RNA specific to p11 wherein the small interfering RNA is comprised of a sequence selected from the group of nucleic acid sequences consisting of SEQ ID NO:18-SEQ ID NO:144.

2. The method of claim 1, wherein the small interfering RNA is comprised of a sequence selected from the group of nucleic acid sequences consisting of SEQ ID NO:18-SEQ ID NO:24.

3. The method of claim 1, wherein the small interfering RNA is comprised of a sequence selected from the group of nucleic acid sequences consisting of SEQ ID NO:22 and SEQ ID NO:24.

4. A method of inhibiting the growth of a tumor, the method comprising administering to a cancer cell a composition that modulates the activity of a p11 protein, wherein the composition comprises a small interfering RNA specific to p11 wherein the small interfering RNA is comprised of a sequence selected from the group of nucleic acid sequences consisting of SEQ ID NO:18-SEQ ID NO:144.

5. The method of claim 4, wherein the small interfering RNA is comprised of a sequence selected from the group of nucleic acid sequences consisting of SEQ ID NO:18-SEQ ID NO:24.

6. The method of claim 4, wherein the small interfering RNA is comprised of a sequence selected from the group of nucleic acid sequences consisting of SEQ ID NO:22 and SEQ ID NO:24.

7. A method of inhibiting cell invasion through an extracellular matrix, the method comprising disrupting the interaction of cell surface p11 with the extracellular matrix wherein the small interfering RNA is comprised of a sequence selected from the group of nucleic acid sequences consisting of SEQ ID NO:18-SEQ ID NO:144.

8. The method of claim 7, wherein the interaction of cell surface p11 with a matrix metalloprotease is disrupted.

9. The method of claim 7, wherein the interaction of cell surface p11 with the extracellular matrix may be disrupted by decreasing cell surface p11.

10. The method of claim 7, wherein the interaction of cell surface p11 with the extracellular matrix may be disrupted by blocking cell surface p11.

11. The method of claim 7, wherein cell surface p11 may be decreased by administering a composition to the cell to decrease p11 surface expression.

12. The method of claim 11, wherein the composition comprises a small interfering RNA specific to p11.

13. The method of claim 12, wherein the small interfering RNA is comprised of a sequence selected from the group of nucleic acid sequences consisting of SEQ ID NO:18-SEQ ID NO:24.

14. The method of claim 12, wherein the small interfering RNA is comprised of a sequence selected from the group of nucleic acid sequences consisting of SEQ ID NO:22 and SEQ ID NO:24.

* * * * *

SEQUENCE LISTING

<160> NUMBER OF SEQ ID NOS: 160

<210> SEQ ID NO 1
<211> LENGTH: 791
<212> TYPE: PRT
<213> ORGANISM: Homo sapiens

<400> SEQUENCE: 1

```
Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
                85                  90                  95

Ser Lys Thr Lys Asn Gly Ile Thr Cys Gln Lys Trp Ser Ser Thr Ser
            100                 105                 110

Pro His Arg Pro Arg Phe Ser Pro Ala Thr His Pro Ser Glu Gly Leu
        115                 120                 125

Glu Glu Asn Tyr Cys Arg Asn Pro Asp Asn Asp Pro Gln Gly Pro Trp
    130                 135                 140

Cys Tyr Thr Thr Asp Pro Glu Lys Arg Tyr Asp Tyr Cys Asp Ile Leu
145                 150                 155                 160

Glu Cys Glu Glu Glu Cys Met His Cys Ser Gly Glu Asn Tyr Asp Gly
                165                 170                 175

Lys Ile Ser Lys Thr Met Ser Gly Leu Glu Cys Gln Ala Trp Asp Ser
            180                 185                 190

Gln Ser Pro His Ala His Gly Tyr Ile Pro Ser Lys Phe Pro Asn Lys
        195                 200                 205

Asn Leu Lys Lys Asn Tyr Cys Arg Asn Pro Asp Arg Glu Leu Arg Pro
    210                 215                 220

Trp Cys Phe Thr Thr Asp Pro Asn Lys Arg Trp Glu Leu Cys Asp Ile
225                 230                 235                 240

Pro Arg Cys Thr Thr Pro Pro Pro Ser Ser Gly Pro Thr Tyr Gln Cys
                245                 250                 255

Leu Lys Gly Thr Gly Glu Asn Tyr Arg Gly Asn Val Ala Val Thr Val
            260                 265                 270

Ser Gly His Thr Cys Gln His Trp Ser Ala Gln Thr Pro His Thr His
        275                 280                 285

Asn Arg Thr Pro Glu Asn Phe Pro Cys Lys Asn Leu Asp Glu Asn Tyr
    290                 295                 300

Cys Arg Asn Pro Asp Gly Lys Arg Ala Pro Trp Cys His Thr Thr Asn
305                 310                 315                 320

Ser Gln Val Arg Trp Glu Tyr Cys Lys Ile Pro Ser Cys Asp Ser Ser
                325                 330                 335

Pro Val Ser Thr Glu Gln Leu Ala Pro Thr Ala Pro Pro Glu Leu Thr
            340                 345                 350

Pro Val Val Gln Asp Cys Tyr His Gly Asp Gly Gln Ser Tyr Arg Gly
        355                 360                 365
```

-continued

```
Thr Ser Ser Thr Thr Thr Thr Gly Lys Lys Cys Gln Ser Trp Ser Ser
    370             375             380
Met Thr Pro His Arg His Gln Lys Thr Pro Glu Asn Tyr Pro Asn Ala
385             390             395             400
Gly Leu Thr Met Asn Tyr Cys Arg Asn Pro Asp Ala Asp Lys Gly Pro
            405             410             415
Trp Cys Phe Thr Thr Asp Pro Ser Val Arg Trp Glu Tyr Cys Asn Leu
        420             425             430
Lys Lys Cys Ser Gly Thr Glu Ala Ser Val Val Ala Pro Pro Pro Val
    435             440             445
Val Leu Leu Pro Asp Val Glu Thr Pro Ser Glu Glu Asp Cys Met Phe
450             455             460
Gly Asn Gly Lys Gly Tyr Arg Gly Lys Arg Ala Thr Thr Val Thr Gly
465             470             475             480
Thr Pro Cys Gln Asp Trp Ala Ala Gln Glu Pro His Arg His Ser Ile
            485             490             495
Phe Thr Pro Glu Thr Asn Pro Arg Ala Gly Leu Glu Lys Asn Tyr Cys
        500             505             510
Arg Asn Pro Asp Gly Asp Val Gly Gly Pro Trp Cys Tyr Thr Thr Asn
    515             520             525
Pro Arg Lys Leu Tyr Asp Tyr Cys Asp Val Pro Gln Cys Ala Ala Pro
530             535             540
Ser Phe Asp Cys Gly Lys Pro Gln Val Glu Pro Lys Lys Cys Pro Gly
545             550             555             560
Arg Val Val Gly Gly Cys Val Ala His Pro His Ser Trp Pro Trp Gln
            565             570             575
Val Ser Leu Arg Thr Arg Phe Gly Met His Phe Cys Gly Gly Thr Leu
        580             585             590
Ile Ser Pro Glu Trp Val Leu Thr Ala Ala His Cys Leu Glu Lys Ser
    595             600             605
Pro Arg Pro Ser Ser Tyr Lys Val Ile Leu Gly Ala His Gln Glu Val
610             615             620
Asn Leu Glu Pro His Val Gln Glu Ile Glu Val Ser Arg Leu Phe Leu
625             630             635             640
Glu Pro Thr Arg Lys Asp Ile Ala Leu Leu Lys Leu Ser Ser Pro Ala
            645             650             655
Val Ile Thr Asp Lys Val Ile Pro Ala Cys Leu Pro Ser Pro Asn Tyr
        660             665             670
Val Val Ala Asp Arg Thr Glu Cys Phe Ile Thr Gly Trp Gly Glu Thr
    675             680             685
Gln Gly Thr Phe Gly Ala Gly Leu Leu Lys Glu Ala Gln Leu Pro Val
690             695             700
Ile Glu Asn Lys Val Cys Asn Arg Tyr Glu Phe Leu Asn Gly Arg Val
705             710             715             720
Gln Ser Thr Glu Leu Cys Ala Gly His Leu Ala Gly Gly Thr Asp Ser
            725             730             735
Cys Gln Gly Asp Ser Gly Gly Pro Leu Val Cys Phe Glu Lys Asp Lys
        740             745             750
Tyr Ile Leu Gln Gly Val Thr Ser Trp Gly Leu Gly Cys Ala Arg Pro
    755             760             765
Asn Lys Pro Gly Val Tyr Val Arg Val Ser Arg Phe Val Thr Trp Ile
770             775             780
Glu Gly Val Met Arg Asn Asn
```

-continued

```
        785                 790

<210> SEQ ID NO 2
<211> LENGTH: 319
<212> TYPE: PRT
<213> ORGANISM: Homo sapiens

<400> SEQUENCE: 2

Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
130                 135                 140

Arg Val Tyr Lys Glu Met Tyr Lys Thr Asp Leu Glu Lys Asp Ile Ile
145                 150                 155                 160

Glu Asp Gly Ser Val Ile Asp Tyr Glu Leu Ile Asp Gln Asp Ala Arg
                165                 170                 175

Asp Leu Tyr Asp Ala Gly Val Lys Arg Lys Gly Thr Asp Val Pro Lys
            180                 185                 190

Trp Ile Ser Ile Met Thr Glu Arg Ser Val Pro His Leu Gln Lys Val
        195                 200                 205

Phe Asp Arg Tyr Lys Ser Tyr Ser Pro Tyr Asp Met Leu Glu Ser Ile
210                 215                 220

Arg Lys Glu Val Lys Gly Asp Leu Glu Asn Ala Phe Leu Asn Leu Val
225                 230                 235                 240

Gln Cys Ile Gln Asn Lys Pro Leu Tyr Phe Ala Asp Arg Leu Tyr Asp
                245                 250                 255

Ser Met Lys Gly Lys Gly Thr Arg Asp Lys Val Leu Ile Arg Ile Met
            260                 265                 270

Val Ser Arg Ser Glu Val Asp Met Leu Lys Ile Arg Ser Glu Phe Lys
        275                 280                 285

Arg Lys Tyr Gly Lys Ser Leu Tyr Tyr Tyr Ile Gln Gln Asp Thr Lys
    290                 295                 300

Gly Asp Tyr Gln Lys Ala Leu Leu Tyr Leu Cys Gly Gly Asp Asp
305                 310                 315

<210> SEQ ID NO 3
<211> LENGTH: 97
<212> TYPE: PRT
<213> ORGANISM: Homo sapiens

<400> SEQUENCE: 3

Met Pro Ser Gln Met Glu His Ala Met Glu Thr Met Met Phe Thr Phe
1               5                   10                  15
```

```
His Lys Phe Ala Gly Asp Lys Gly Tyr Leu Thr Lys Glu Asp Leu Arg
            20                  25                  30

Val Leu Met Glu Lys Glu Phe Pro Gly Phe Leu Glu Asn Gln Lys Asp
        35                  40                  45

Pro Leu Ala Val Asp Lys Ile Met Lys Asp Leu Asp Gln Cys Arg Asp
    50                  55                  60

Gly Lys Val Gly Phe Gln Ser Phe Phe Ser Leu Ile Ala Gly Leu Thr
65                  70                  75                  80

Ile Ala Cys Asn Asp Tyr Phe Val Val His Met Lys Gln Lys Gly Lys
                85                  90                  95

Lys

<210> SEQ ID NO 4
<211> LENGTH: 6
<212> TYPE: PRT
<213> ORGANISM: Artificial Sequence
<220> FEATURE:
<223> OTHER INFORMATION: Homo sapiens

<400> SEQUENCE: 4

Trp Cys Gly Pro Cys Lys
1               5

<210> SEQ ID NO 5
<211> LENGTH: 291
<212> TYPE: DNA
<213> ORGANISM: Artificial Sequence
<220> FEATURE:
<223> OTHER INFORMATION: Homo sapiens

<400> SEQUENCE: 5
cttctttccc ttctgcttca tgtgtactac aaaatagtca ttgcatgcaa tggtgaggcc      60
cgcaattagg gaaagaagc tctggaagcc cactttgcca tctctacact ggtccaggtc     120
cttcattatt tgtccacag ccagagggtc tttttgattt ccaaaaatc cagggaactc      180 cttttccatg agtactctca ggtcctcctt tgttaagtag cctttatccc cagcgaattt     240
gtgaaatgta aacatcatgg tttccatggc gtgttccatt tgagatggca t             291

<210> SEQ ID NO 6
<211> LENGTH: 291
<212> TYPE: DNA
<213> ORGANISM: Homo sapiens

<400> SEQUENCE: 6
atgccatctc aaatggaaca cgccatggaa accatgatgt ttacatttca caaattcgct      60
ggggataaag gctacttaac aaaggaggac ctgagagtac tcatggaaaa ggagttccct     120
ggatttttgg aaaatcaaaa agaccctctg gctgtggaca aataatgaa ggacctggac      180 cagtgtagag atgcaaagt gggcttccag agcttctttt ccctaattgc gggcctcacc     240
attgcatgca atgactattt tgtagtacac atgaagcaga agggaaagaa g              291

<210> SEQ ID NO 7
<211> LENGTH: 391
<212> TYPE: PRT
<213> ORGANISM: Homo sapiens

<400> SEQUENCE: 7

Lys Val Tyr Leu Ser Glu Cys Lys Thr Gly Asn Gly Lys Asn Tyr Arg
1               5                  10                  15
```

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
 50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Cys Met His Cys Ser Gly Glu Asn
                85                  90                  95

Tyr Asp Gly Lys Ile Ser Lys Thr Met Ser Gly Leu Glu Cys Gln Ala
                100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
        130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
                180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
        210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala Ser Val Val Ala Pro
        355                 360                 365

Pro Pro Val Val Leu Leu Pro Asp Val Glu Thr Pro Ser Glu Glu Asp
370                 375                 380

Cys Met Phe Gly Asn Gly Lys
385                 390

<210> SEQ ID NO 8
<211> LENGTH: 394
<212> TYPE: PRT
<213> ORGANISM: Homo sapiens

<400> SEQUENCE: 8

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
                20                  25                  30

Ser Thr Ser Pro His Arg Pro Arg Phe Ser Pro Ala Thr His Pro Ser
            35                  40                  45

Glu Gly Leu Glu Glu Asn Tyr Cys Arg Asn Pro Asp Asn Asp Pro Gln
50                      55                  60

Gly Pro Trp Cys Tyr Thr Thr Asp Pro Glu Lys Arg Tyr Asp Tyr Cys
65                  70                      75                  80

Asp Ile Leu Glu Cys Glu Glu Cys Met His Cys Ser Gly Glu Asn
                85                  90                      95

Tyr Asp Gly Lys Ile Ser Lys Thr Met Ser Gly Leu Glu Cys Gln Ala
                100                 105                 110

Trp Asp Ser Gln Ser Pro His Ala His Gly Tyr Ile Pro Ser Lys Phe
            115                 120                 125

Pro Asn Lys Asn Leu Lys Lys Asn Tyr Cys Arg Asn Pro Asp Arg Glu
            130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Ser Ser Gly Pro Thr
                165                 170                 175

Tyr Gln Cys Leu Lys Gly Thr Gly Glu Asn Tyr Arg Gly Asn Val Ala
                180                 185                 190

Val Thr Val Ser Gly His Thr Cys Gln His Trp Ser Ala Gln Thr Pro
            195                 200                 205

His Thr His Asn Arg Thr Pro Glu Asn Phe Pro Cys Lys Asn Leu Asp
210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
            275                 280                 285

Tyr Arg Gly Thr Ser Ser Thr Thr Thr Gly Lys Lys Cys Gln Ser
            290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
                340                 345                 350

Cys Asn Leu Lys Lys Cys Ser Gly Thr Glu Ala Ser Val Val Ala Pro
            355                 360                 365

Pro Pro Val Val Leu Leu Pro Asp Val Glu Thr Pro Ser Glu Glu Asp
        370                 375                 380

Cys Met Phe Gly Asn Gly Lys Gly Tyr Arg
385                 390

<210> SEQ ID NO 9
<211> LENGTH: 26
<212> TYPE: DNA
<213> ORGANISM: Artificial Sequence
```

```
<220> FEATURE:
<223> OTHER INFORMATION: Homo sapiens

<400> SEQUENCE: 9
atgcggccgc atgccatctc aaatgg                                              26

<210> SEQ ID NO 10
<211> LENGTH: 24
<212> TYPE: DNA
<213> ORGANISM: Artificial Sequence
<220> FEATURE:
<223> OTHER INFORMATION: Homo sapiens

<400> SEQUENCE: 10
atagatctct acttctttcc cttc                                                24

<210> SEQ ID NO 11
<211> LENGTH: 24
<212> TYPE: DNA
<213> ORGANISM: Artificial Sequence
<220> FEATURE:
<223> OTHER INFORMATION: Homo sapiens

<400> SEQUENCE: 11
atagatctat gccatctcaa atgg                                                24

<210> SEQ ID NO 12
<211> LENGTH: 28
<212> TYPE: DNA
<213> ORGANISM: Artificial Sequence
<220> FEATURE:
<223> OTHER INFORMATION: Homo sapiens

<400> SEQUENCE: 12
atgcggccgc ctacttcttt cccttctg                                            28

<210> SEQ ID NO 13
<211> LENGTH: 21
<212> TYPE: DNA
<213> ORGANISM: Artificial Sequence
<220> FEATURE:
<223> OTHER INFORMATION: Homo sapiens

<400> SEQUENCE: 13
tctacactgg tccaggtcct t                                                   21

<210> SEQ ID NO 14
<211> LENGTH: 21
<212> TYPE: DNA
<213> ORGANISM: Artificial Sequence
<220> FEATURE:
<223> OTHER INFORMATION: Homo sapiens

<400> SEQUENCE: 14
agaagctctg gaagcccact t                                                   21

<210> SEQ ID NO 15
<211> LENGTH: 21
<212> TYPE: DNA
<213> ORGANISM: Artificial Sequence
<220> FEATURE:
<223> OTHER INFORMATION: Homo sapiens

<400> SEQUENCE: 15
agaagctctg gaagcccact t                                                   21
```

<210> SEQ ID NO 16
<211> LENGTH: 1199
<212> TYPE: DNA
<213> ORGANISM: Artificial Sequence
<220> FEATURE:
<223> OTHER INFORMATION: Homo sapiens

<400> SEQUENCE: 16

```
ggaactaaaa aagaacttta tttattgagg gcaaggggat gcaaacaata caaaaatcaa      60
aagcttatct ggtatttaac tttctttct ctgcttgtca aatgagagtt agatttatt      120
tttacatttg ctaagtgtcc tgatctgctc atgaaatcct tctatggggg aagctgtggg     180
gcagattcct taagcgaccc tttgggacaa ctcttatcag ggaggagcga actgctcatt     240
tctgcctact tctttccctt ctgcttcatg tgtactacaa aatagtcatt gcatgcaatg     300
gtgaggcccg caattaggga aaagaagctc tggaagccca ctttgccatc tctacactgg     360
tccaggtcct tcattatttt gtccacagcc agagggtctt tttgattttc caaaaatcca     420
gggaactcct tttccatgag tactctcagg tcctcctttg ttaagtagcc tttatcccca     480
gcgaatttgt gaaatgtaaa catcatggtt tccatggcgt gttccatttg agatggcatt     540
ttggtgtggt ccgttgaagc cttggccgag gcgcggcgga cgctgggcga gctgggcgag     600
ctggacgcgg ggcggagagg cgagcgcggc gggctgtgcg ccttccttag tacgtgcggc     660
gggtgggtag agggaggcgg cgcgggagcg ggaggagcct ggcgggcgct cggcagggcg     720
ctcccccagc cctgtctcct cccctcttc ctgccccga ctccccgac cccgggcgcg       780
cggcccacgc cctgccctcg ctcccggacc cgcctcgcag aggcctcgcc cgccccagac     840
agagcgttct tgtaaacttc tcttcagtag aaacggtcct gctctcgaat atttcagggc     900
atccccaccc tgagcctgcc cttcctctcg ggttttggttt tagaaagtgt acaaatcaaa     960
gaacccggcc gtcctgcggg tggggcacgc tggcgcagaa ccagaggtaa ccggctctgc    1020
ggccacctac gggtctagga attacttgct ggatgaccct gcaggagtg gcacgtggag     1080
tcctatcgac ctcagaggca ctatcagatt agccctagga ggtccgtctg ggggtctcgg    1140
cggcctgcgc cagtggaggg gcggcacctc cccagaagcc gggcttcccg ccccaccgg    1199
```

<210> SEQ ID NO 17
<211> LENGTH: 1199
<212> TYPE: DNA
<213> ORGANISM: Homo sapiens

<400> SEQUENCE: 17

```
ccggtggggc gggaagcccg gcttctgggg aggtgccgcc cctccactgg cgcaggccgc      60
cgagaccccc agacggacct cctagggcta atctgatagt gccctgagg tcgataggac      120
tccacgtgcc actccctgca gggtcatcca gcaagtaatt cctagacccg taggtggccg     180
cagagccggt tacctctggt tctgcgccag cgtgccccac ccgcaggacg gccgggttct     240
ttgatttgta cactttctaa aaccaaaccc gagaggaagg gcaggctcag ggtggggatg     300
ccctgaaata ttcgagagca ggaccgtttc tactgaagag aagtttacaa gaacgctctg     360
tctggggcgg gcgaggcctc tgcgaggcgg gtccgggagc gagggcaggg cgtgggccgc     420
gcgcccgggg tcgggggagt cgggggcagg aagaggggga ggagacaggg ctggggagc     480
gccctgccga gcgcccgcca ggctcctccc gctcccgcgc cgcctccctc tacccacccg     540
ccgcacgtac taaggaaggc gcacagcccg ccgcgctcgc ctctccgccc gcgtccagc     600
tcgcccagct cgcccagcgt ccgccgcgcc tcggccaagg cttcaacgga ccacaccaaa     660
atgccatctc aaatggaaca cgccatggaa accatgatgt ttacatttca caaattcgct     720
```

```
ggggataaag gctacttaac aaaggaggac ctgagagtac tcatggaaaa ggagttccct    780 ggattttgg aaaatcaaaa agaccctctg gctgtggaca aaataatgaa ggacctggac    840
cagtgtagag atggcaaagt gggcttccag agcttctttt ccctaattgc gggcctcacc    900
attgcatgca atgactattt tgtagtacac atgaagcaga agggaaagaa gtaggcagaa    960
atgagcagtt cgctcctccc tgataagagt tgtcccaaag ggtcgcttaa ggaatctgcc   1020
ccacagcttc ccccatagaa ggatttcatg agcagatcag gacacttagc aaatgtaaaa   1080
ataaaatcta actctcattt gacaagcaga gaaagaaaag ttaaatacca gataagcttt   1140 tgattttgt attgtttgca tccccttgcc ctcaataaat aaagttcttt tttagttcc    1199
```

<210> SEQ ID NO 18
<211> LENGTH: 21
<212> TYPE: DNA
<213> ORGANISM: Artificial Sequence
<220> FEATURE:
<223> OTHER INFORMATION: Homo sapiens

<400> SEQUENCE: 18
ggaccuggac caguguagau u                                              21

<210> SEQ ID NO 19
<211> LENGTH: 21
<212> TYPE: DNA
<213> ORGANISM: Artificial Sequence
<220> FEATURE:
<223> OTHER INFORMATION: Homo sapiens

<400> SEQUENCE: 19
uuccuggacc uggucacauc u                                              21

<210> SEQ ID NO 20
<211> LENGTH: 21
<212> TYPE: DNA
<213> ORGANISM: Artificial Sequence
<220> FEATURE:
<223> OTHER INFORMATION: Homo sapiens

<400> SEQUENCE: 20
gugggcuucc acagcuucuu u                                              21

<210> SEQ ID NO 21
<211> LENGTH: 21
<212> TYPE: DNA
<213> ORGANISM: Artificial Sequence
<220> FEATURE:
<223> OTHER INFORMATION: Homo sapiens

<400> SEQUENCE: 21
uucacccgaa ggugucgaag a                                              21

<210> SEQ ID NO 22
<211> LENGTH: 19
<212> TYPE: DNA
<213> ORGANISM: Artificial Sequence
<220> FEATURE:
<223> OTHER INFORMATION: Homo sapiens

<400> SEQUENCE: 22
gtgggcttcc agagcttct                                                 19

<210> SEQ ID NO 23
<211> LENGTH: 9

```
<212> TYPE: DNA
<213> ORGANISM: Artificial Sequence
<220> FEATURE:
<223> OTHER INFORMATION: Homo sapiens

<400> SEQUENCE: 23 tctcttgaa                                                                9

<210> SEQ ID NO 24
<211> LENGTH: 19
<212> TYPE: DNA
<213> ORGANISM: Artificial Sequence
<220> FEATURE:
<223> OTHER INFORMATION: Homo sapiens

<400> SEQUENCE: 24
gcgcgctttg taggattcg                                                    19

<210> SEQ ID NO 25
<211> LENGTH: 22
<212> TYPE: DNA
<213> ORGANISM: Artificial Sequence
<220> FEATURE:
<223> OTHER INFORMATION: Homo sapiens

<400> SEQUENCE: 25
auauucgaga gcaggaccgu tt                                                22

<210> SEQ ID NO 26
<211> LENGTH: 22
<212> TYPE: DNA
<213> ORGANISM: Artificial Sequence
<220> FEATURE:
<223> OTHER INFORMATION: Homo sapiens

<400> SEQUENCE: 26 acguccugc ucucgaauau tt                                                 22

<210> SEQ ID NO 27
<211> LENGTH: 21
<212> TYPE: DNA
<213> ORGANISM: Artificial Sequence
<220> FEATURE:
<223> OTHER INFORMATION: Homo sapiens

<400> SEQUENCE: 27
ggcuucaacg gaccacacct t                                                 21

<210> SEQ ID NO 28
<211> LENGTH: 21
<212> TYPE: DNA
<213> ORGANISM: Artificial Sequence
<220> FEATURE:
<223> OTHER INFORMATION: Homo sapiens

<400> SEQUENCE: 28 ggguguggucc guugaagcct t                                                21

<210> SEQ ID NO 29
<211> LENGTH: 21
<212> TYPE: DNA
<213> ORGANISM: Artificial Sequence
<220> FEATURE:
<223> OTHER INFORMATION: Homo sapiens

<400> SEQUENCE: 29
uauucgagag caggaccgut t                                                 21
```

<210> SEQ ID NO 30
<211> LENGTH: 21
<212> TYPE: DNA
<213> ORGANISM: Artificial Sequence
<220> FEATURE:
<223> OTHER INFORMATION: Homo sapiens

<400> SEQUENCE: 30
acgguccugc ucucgaauat t                                    21

<210> SEQ ID NO 31
<211> LENGTH: 21
<212> TYPE: DNA
<213> ORGANISM: Artificial Sequence
<220> FEATURE:
<223> OTHER INFORMATION: Homo sapiens

<400> SEQUENCE: 31
auauucgaga gcaggaccgt t                                    21

<210> SEQ ID NO 32
<211> LENGTH: 21
<212> TYPE: DNA
<213> ORGANISM: Artificial Sequence
<220> FEATURE:
<223> OTHER INFORMATION: Homo sapiens

<400> SEQUENCE: 32
cgguccugcu cucgaauaut t                                    21

<210> SEQ ID NO 33
<211> LENGTH: 21
<212> TYPE: DNA
<213> ORGANISM: Artificial Sequence
<220> FEATURE:
<223> OTHER INFORMATION: Homo sapiens

<400> SEQUENCE: 33
gagaaguuua caagaacgct t                                    21

<210> SEQ ID NO 34
<211> LENGTH: 21
<212> TYPE: DNA
<213> ORGANISM: Artificial Sequence
<220> FEATURE:
<223> OTHER INFORMATION: Homo sapiens

<400> SEQUENCE: 34
gcguucuugu aaacuucuct t                                    21

<210> SEQ ID NO 35
<211> LENGTH: 21
<212> TYPE: DNA
<213> ORGANISM: Artificial Sequence
<220> FEATURE:
<223> OTHER INFORMATION: Homo sapiens

<400> SEQUENCE: 35
gacggccggg uucuuugaut t                                    21

<210> SEQ ID NO 36
<211> LENGTH: 21
<212> TYPE: DNA
<213> ORGANISM: Artificial Sequence
<220> FEATURE:
<223> OTHER INFORMATION: Homo sapiens

```
<400> SEQUENCE: 36
cucaaagaac ccggccguct t                                              21

<210> SEQ ID NO 37
<211> LENGTH: 20
<212> TYPE: DNA
<213> ORGANISM: Artificial Sequence
<220> FEATURE:
<223> OTHER INFORMATION: Homo sapiens

<400> SEQUENCE: 37
ggcuucaacg gaccacactt                                                20

<210> SEQ ID NO 38
<211> LENGTH: 20
<212> TYPE: DNA
<213> ORGANISM: Artificial Sequence
<220> FEATURE:
<223> OTHER INFORMATION: Homo sapiens

<400> SEQUENCE: 38
gugugguccg uugaagcctt                                                20

<210> SEQ ID NO 39
<211> LENGTH: 21
<212> TYPE: DNA
<213> ORGANISM: Artificial Sequence
<220> FEATURE:
<223> OTHER INFORMATION: Homo sapiens

<400> SEQUENCE: 39
augccaucuc aauggaact t                                               21

<210> SEQ ID NO 40
<211> LENGTH: 21
<212> TYPE: DNA
<213> ORGANISM: Artificial Sequence
<220> FEATURE:
<223> OTHER INFORMATION: Homo sapiens

<400> SEQUENCE: 40
guuccauuug agauggcaut t                                              21

<210> SEQ ID NO 41
<211> LENGTH: 20
<212> TYPE: DNA
<213> ORGANISM: Artificial Sequence
<220> FEATURE:
<223> OTHER INFORMATION: Homo sapiens

<400> SEQUENCE: 41
auucgagagc aggaccgutt                                                20

<210> SEQ ID NO 42
<211> LENGTH: 20
<212> TYPE: DNA
<213> ORGANISM: Artificial Sequence
<220> FEATURE:
<223> OTHER INFORMATION: Homo sapiens

<400> SEQUENCE: 42
acgguccugc ucucgaautt                                                20

<210> SEQ ID NO 43
<211> LENGTH: 22
```

<212> TYPE: DNA
<213> ORGANISM: Artificial Sequence
<220> FEATURE:
<223> OTHER INFORMATION: Homo sapiens

<400> SEQUENCE: 43
auggaacacg ccauggaaac tt                                            22

<210> SEQ ID NO 44
<211> LENGTH: 22
<212> TYPE: DNA
<213> ORGANISM: Artificial Sequence
<220> FEATURE:
<223> OTHER INFORMATION: Homo sapiens

<400> SEQUENCE: 44
guuuccaugg cguguuccau tt                                            22

<210> SEQ ID NO 45
<211> LENGTH: 21
<212> TYPE: DNA
<213> ORGANISM: Artificial Sequence
<220> FEATURE:
<223> OTHER INFORMATION: Homo sapiens

<400> SEQUENCE: 45
guuuacaaga acgcucugut t                                             21

<210> SEQ ID NO 46
<211> LENGTH: 21
<212> TYPE: DNA
<213> ORGANISM: Artificial Sequence
<220> FEATURE:
<223> OTHER INFORMATION: Homo sapiens

<400> SEQUENCE: 46
acatagcguu cuuguaaact t                                             21

<210> SEQ ID NO 47
<211> LENGTH: 21
<212> TYPE: DNA
<213> ORGANISM: Artificial Sequence
<220> FEATURE:
<223> OTHER INFORMATION: Homo sapiens

<400> SEQUENCE: 47
gccauggaaa ccaugaugut t                                             21

<210> SEQ ID NO 48
<211> LENGTH: 21
<212> TYPE: DNA
<213> ORGANISM: Artificial Sequence
<220> FEATURE:
<223> OTHER INFORMATION: Homo sapiens

<400> SEQUENCE: 48
acaucauggu uuccauggct t                                             21

<210> SEQ ID NO 49
<211> LENGTH: 22
<212> TYPE: DNA
<213> ORGANISM: Artificial Sequence
<220> FEATURE:
<223> OTHER INFORMATION: Homo sapiens

<400> SEQUENCE: 49
ggacggccgg guucuuugau tt                                            22

<210> SEQ ID NO 50
<211> LENGTH: 22
<212> TYPE: DNA
<213> ORGANISM: Artificial Sequence
<220> FEATURE:
<223> OTHER INFORMATION: Homo sapiens

<400> SEQUENCE: 50
aucaaagaac ccggccgucc tt                                              22

<210> SEQ ID NO 51
<211> LENGTH: 21
<212> TYPE: DNA
<213> ORGANISM: Artificial Sequence
<220> FEATURE:
<223> OTHER INFORMATION: Homo sapiens

<400> SEQUENCE: 51
guuucuacug aagagaagut t                                               21

<210> SEQ ID NO 52
<211> LENGTH: 21
<212> TYPE: DNA
<213> ORGANISM: Artificial Sequence
<220> FEATURE:
<223> OTHER INFORMATION: Homo sapiens

<400> SEQUENCE: 52
acuucucuuc aguagaaact t                                               21

<210> SEQ ID NO 53
<211> LENGTH: 22
<212> TYPE: DNA
<213> ORGANISM: Artificial Sequence
<220> FEATURE:
<223> OTHER INFORMATION: Homo sapiens

<400> SEQUENCE: 53
gagaaguuua caagaacgcu tt                                              22

<210> SEQ ID NO 54
<211> LENGTH: 22
<212> TYPE: DNA
<213> ORGANISM: Artificial Sequence
<220> FEATURE:
<223> OTHER INFORMATION: Homo sapiens

<400> SEQUENCE: 54
agcguucuug uaaacuucuc tt                                              22

<210> SEQ ID NO 55
<211> LENGTH: 20
<212> TYPE: DNA
<213> ORGANISM: Artificial Sequence
<220> FEATURE:
<223> OTHER INFORMATION: Homo sapiens

<400> SEQUENCE: 55
auauucgaga gcaggacctt                                                 20

<210> SEQ ID NO 56
<211> LENGTH: 20
<212> TYPE: DNA
<213> ORGANISM: Artificial Sequence
<220> FEATURE:
<223> OTHER INFORMATION: Homo sapiens -continued

<400> SEQUENCE: 56
gguccugcuc ucgaauautt                                         20

<210> SEQ ID NO 57
<211> LENGTH: 21
<212> TYPE: DNA
<213> ORGANISM: Artificial Sequence
<220> FEATURE:
<223> OTHER INFORMATION: Homo sapiens

<400> SEQUENCE: 57
gguucuuuga uuuguacact t                                       21

<210> SEQ ID NO 58
<211> LENGTH: 21
<212> TYPE: DNA
<213> ORGANISM: Artificial Sequence
<220> FEATURE:
<223> OTHER INFORMATION: Homo sapiens

<400> SEQUENCE: 58
guguacaaau caaagaacct t                                       21

<210> SEQ ID NO 59
<211> LENGTH: 21
<212> TYPE: DNA
<213> ORGANISM: Artificial Sequence
<220> FEATURE:
<223> OTHER INFORMATION: Homo sapiens

<400> SEQUENCE: 59
gaaaccauga uguuuacaut t                                       21

<210> SEQ ID NO 60
<211> LENGTH: 21
<212> TYPE: DNA
<213> ORGANISM: Artificial Sequence
<220> FEATURE:
<223> OTHER INFORMATION: Homo sapiens

<400> SEQUENCE: 60
auguaaacau caugguuuct t                                       21

<210> SEQ ID NO 61
<211> LENGTH: 22
<212> TYPE: DNA
<213> ORGANISM: Artificial Sequence
<220> FEATURE:
<223> OTHER INFORMATION: Homo sapiens

<400> SEQUENCE: 61
guuuacaaga acgcucuguc tt                                      22

<210> SEQ ID NO 62
<211> LENGTH: 22
<212> TYPE: DNA
<213> ORGANISM: Artificial Sequence
<220> FEATURE:
<223> OTHER INFORMATION: Homo sapiens

<400> SEQUENCE: 62
gacagagcgu ucuuguaaac tt                                      22

<210> SEQ ID NO 63
<211> LENGTH: 21

```
<212> TYPE: DNA
<213> ORGANISM: Artificial Sequence
<220> FEATURE:
<223> OTHER INFORMATION: Homo sapiens

<400> SEQUENCE: 63
accaugaugu uuacauuuct t                                              21

<210> SEQ ID NO 64
<211> LENGTH: 21
<212> TYPE: DNA
<213> ORGANISM: Artificial Sequence
<220> FEATURE:
<223> OTHER INFORMATION: Homo sapiens

<400> SEQUENCE: 64
gaaauguaaa caucauggut t                                              21

<210> SEQ ID NO 65
<211> LENGTH: 22
<212> TYPE: DNA
<213> ORGANISM: Artificial Sequence
<220> FEATURE:
<223> OTHER INFORMATION: Homo sapiens

<400> SEQUENCE: 65
auauucgaga gcaggaccgu tt                                             22

<210> SEQ ID NO 66
<211> LENGTH: 22
<212> TYPE: DNA
<213> ORGANISM: Artificial Sequence
<220> FEATURE:
<223> OTHER INFORMATION: Homo sapiens

<400> SEQUENCE: 66
acgguccugc ucucgaauau tt                                             22

<210> SEQ ID NO 67
<211> LENGTH: 21
<212> TYPE: DNA
<213> ORGANISM: Artificial Sequence
<220> FEATURE:
<223> OTHER INFORMATION: Homo sapiens

<400> SEQUENCE: 67
uauucgagag caggaccgut t                                              21

<210> SEQ ID NO 68
<211> LENGTH: 21
<212> TYPE: DNA
<213> ORGANISM: Artificial Sequence
<220> FEATURE:
<223> OTHER INFORMATION: Homo sapiens

<400> SEQUENCE: 68
acgguccugc ucucgaauat t                                              21

<210> SEQ ID NO 69
<211> LENGTH: 21
<212> TYPE: DNA
<213> ORGANISM: Artificial Sequence
<220> FEATURE:
<223> OTHER INFORMATION: Homo sapiens

<400> SEQUENCE: 69
auauucgaga gcaggaccgt t                                              21
```

<210> SEQ ID NO 70
<211> LENGTH: 21
<212> TYPE: DNA
<213> ORGANISM: Artificial Sequence
<220> FEATURE:
<223> OTHER INFORMATION: Homo sapiens

<400> SEQUENCE: 70
cgguccugcu cucgaauaut t                                              21

<210> SEQ ID NO 71
<211> LENGTH: 21
<212> TYPE: DNA
<213> ORGANISM: Artificial Sequence
<220> FEATURE:
<223> OTHER INFORMATION: Homo sapiens

<400> SEQUENCE: 71
gagaaguuua caagaacgct t                                              21

<210> SEQ ID NO 72
<211> LENGTH: 21
<212> TYPE: DNA
<213> ORGANISM: Artificial Sequence
<220> FEATURE:
<223> OTHER INFORMATION: Homo sapiens

<400> SEQUENCE: 72
gcguucuugu aaacuucuct t                                              21

<210> SEQ ID NO 73
<211> LENGTH: 21
<212> TYPE: DNA
<213> ORGANISM: Artificial Sequence
<220> FEATURE:
<223> OTHER INFORMATION: Homo sapiens

<400> SEQUENCE: 73
gacggccggg uucuuugaut t                                              21

<210> SEQ ID NO 74
<211> LENGTH: 21
<212> TYPE: DNA
<213> ORGANISM: Artificial Sequence
<220> FEATURE:
<223> OTHER INFORMATION: Homo sapiens

<400> SEQUENCE: 74
aucaaagaac ccggccguct t                                              21

<210> SEQ ID NO 75
<211> LENGTH: 20
<212> TYPE: DNA
<213> ORGANISM: Artificial Sequence
<220> FEATURE:
<223> OTHER INFORMATION: Homo sapiens

<400> SEQUENCE: 75
auucgagagc aggaccgutt                                                20

<210> SEQ ID NO 76
<211> LENGTH: 20
<212> TYPE: DNA
<213> ORGANISM: Artificial Sequence
<220> FEATURE:
<223> OTHER INFORMATION: Homo sapiens

```
<400> SEQUENCE: 76
acgguccugc ucucgaautt                                               20

<210> SEQ ID NO 77
<211> LENGTH: 21
<212> TYPE: DNA
<213> ORGANISM: Artificial Sequence
<220> FEATURE:
<223> OTHER INFORMATION: Homo sapiens

<400> SEQUENCE: 77
guuuacaaga acgcucugut t                                             21

<210> SEQ ID NO 78
<211> LENGTH: 21
<212> TYPE: DNA
<213> ORGANISM: Artificial Sequence
<220> FEATURE:
<223> OTHER INFORMATION: Homo sapiens

<400> SEQUENCE: 78
acagagcguu cuuguaaact t                                             21

<210> SEQ ID NO 79
<211> LENGTH: 22
<212> TYPE: DNA
<213> ORGANISM: Artificial Sequence
<220> FEATURE:
<223> OTHER INFORMATION: Homo sapiens

<400> SEQUENCE: 79
ggacggccgg guucuuugau tt                                            22

<210> SEQ ID NO 80
<211> LENGTH: 22
<212> TYPE: DNA
<213> ORGANISM: Artificial Sequence
<220> FEATURE:
<223> OTHER INFORMATION: Homo sapiens

<400> SEQUENCE: 80
aucaaagaac ccggccgucc tt                                            22

<210> SEQ ID NO 81
<211> LENGTH: 21
<212> TYPE: DNA
<213> ORGANISM: Artificial Sequence
<220> FEATURE:
<223> OTHER INFORMATION: Homo sapiens

<400> SEQUENCE: 81
guuucuacug aagagaagut t                                             21

<210> SEQ ID NO 82
<211> LENGTH: 21
<212> TYPE: DNA
<213> ORGANISM: Artificial Sequence
<220> FEATURE:
<223> OTHER INFORMATION: Homo sapiens

<400> SEQUENCE: 82
acuucucuuc aguagaaact t                                             21

<210> SEQ ID NO 83
<211> LENGTH: 22
```

```
<212> TYPE: DNA
<213> ORGANISM: Artificial Sequence
<220> FEATURE:
<223> OTHER INFORMATION: Homo sapiens

<400> SEQUENCE: 83
gagaaguuua caagaacgcu tt                                              22

<210> SEQ ID NO 84
<211> LENGTH: 22
<212> TYPE: DNA
<213> ORGANISM: Artificial Sequence
<220> FEATURE:
<223> OTHER INFORMATION: Homo sapiens

<400> SEQUENCE: 84
agcguucuug uaaacuucuc tt                                              22

<210> SEQ ID NO 85
<211> LENGTH: 20
<212> TYPE: DNA
<213> ORGANISM: Artificial Sequence
<220> FEATURE:
<223> OTHER INFORMATION: Homo sapiens

<400> SEQUENCE: 85
auauucgaga gcaggacctt                                                 20

<210> SEQ ID NO 86
<211> LENGTH: 20
<212> TYPE: DNA
<213> ORGANISM: Artificial Sequence
<220> FEATURE:
<223> OTHER INFORMATION: Homo sapiens

<400> SEQUENCE: 86
gguccugcuc ucgaauautt                                                 20

<210> SEQ ID NO 87
<211> LENGTH: 21
<212> TYPE: DNA
<213> ORGANISM: Artificial Sequence
<220> FEATURE:
<223> OTHER INFORMATION: Homo sapiens

<400> SEQUENCE: 87
gguucuuuga uuuguacact t                                               21

<210> SEQ ID NO 88
<211> LENGTH: 21
<212> TYPE: DNA
<213> ORGANISM: Artificial Sequence
<220> FEATURE:
<223> OTHER INFORMATION: Homo sapiens

<400> SEQUENCE: 88
guguacaaau caaagaacct t                                               21

<210> SEQ ID NO 89
<211> LENGTH: 22
<212> TYPE: DNA
<213> ORGANISM: Artificial Sequence
<220> FEATURE:
<223> OTHER INFORMATION: Homo sapiens

<400> SEQUENCE: 89
guuuacaaga acgcucuguc tt                                              22
```

```
<210> SEQ ID NO 90
<211> LENGTH: 22
<212> TYPE: DNA
<213> ORGANISM: Artificial Sequence
<220> FEATURE:
<223> OTHER INFORMATION: Homo sapiens

<400> SEQUENCE: 90
gacagagcgu ucuuguaaac tt                                              22

<210> SEQ ID NO 91
<211> LENGTH: 20
<212> TYPE: DNA
<213> ORGANISM: Artificial Sequence
<220> FEATURE:
<223> OTHER INFORMATION: Homo sapiens

<400> SEQUENCE: 91
acggccgggu ucuuugautt                                                 20

<210> SEQ ID NO 92
<211> LENGTH: 20
<212> TYPE: DNA
<213> ORGANISM: Artificial Sequence
<220> FEATURE:
<223> OTHER INFORMATION: Homo sapiens

<400> SEQUENCE: 92
aucaaagaac ccggccgutt                                                 20

<210> SEQ ID NO 93
<211> LENGTH: 21
<212> TYPE: DNA
<213> ORGANISM: Artificial Sequence
<220> FEATURE:
<223> OTHER INFORMATION: Homo sapiens

<400> SEQUENCE: 93
guucuuugau uuguacacut t                                               21

<210> SEQ ID NO 94
<211> LENGTH: 21
<212> TYPE: DNA
<213> ORGANISM: Artificial Sequence
<220> FEATURE:
<223> OTHER INFORMATION: Homo sapiens

<400> SEQUENCE: 94
aguguacaaa ucaaagaact t                                               21

<210> SEQ ID NO 95
<211> LENGTH: 22
<212> TYPE: DNA
<213> ORGANISM: Artificial Sequence
<220> FEATURE:
<223> OTHER INFORMATION: Homo sapiens

<400> SEQUENCE: 95
ggguucuuug auuuguacac tt                                              22

<210> SEQ ID NO 96
<211> LENGTH: 22
<212> TYPE: DNA
<213> ORGANISM: Artificial Sequence
<220> FEATURE:
<223> OTHER INFORMATION: Homo sapiens
```

<400> SEQUENCE: 96
guguacaaau caaagaaccc tt                                                22

<210> SEQ ID NO 97
<211> LENGTH: 22
<212> TYPE: DNA
<213> ORGANISM: Artificial Sequence
<220> FEATURE:
<223> OTHER INFORMATION: Homo sapiens

<400> SEQUENCE: 97
gguucuuuga uuuguacacu tt                                                22

<210> SEQ ID NO 98
<211> LENGTH: 22
<212> TYPE: DNA
<213> ORGANISM: Artificial Sequence
<220> FEATURE:
<223> OTHER INFORMATION: Homo sapiens

<400> SEQUENCE: 98
aguguacaaa ucaaagaacc tt                                                22

<210> SEQ ID NO 99
<211> LENGTH: 20
<212> TYPE: DNA
<213> ORGANISM: Artificial Sequence
<220> FEATURE:
<223> OTHER INFORMATION: Homo sapiens

<400> SEQUENCE: 99
guucuuugau uuguacactt                                                   20

<210> SEQ ID NO 100
<211> LENGTH: 20
<212> TYPE: DNA
<213> ORGANISM: Artificial Sequence
<220> FEATURE:
<223> OTHER INFORMATION: Homo sapiens

<400> SEQUENCE: 100
guguacaaau caaagaactt                                                   20

<210> SEQ ID NO 101
<211> LENGTH: 21
<212> TYPE: DNA
<213> ORGANISM: Artificial Sequence
<220> FEATURE:
<223> OTHER INFORMATION: Homo sapiens

<400> SEQUENCE: 101
ggaagggcag gcucagggut t                                                 21

<210> SEQ ID NO 102
<211> LENGTH: 21
<212> TYPE: DNA
<213> ORGANISM: Artificial Sequence
<220> FEATURE:
<223> OTHER INFORMATION: Homo sapiens

<400> SEQUENCE: 102
acccugagcc ugcccuucct t                                                 21

<210> SEQ ID NO 103
<211> LENGTH: 21

```
<212> TYPE: DNA
<213> ORGANISM: Artificial Sequence
<220> FEATURE:
<223> OTHER INFORMATION: Homo sapiens

<400> SEQUENCE: 103
agacggaccu ccuagggcut t                                              21

<210> SEQ ID NO 104
<211> LENGTH: 21
<212> TYPE: DNA
<213> ORGANISM: Artificial Sequence
<220> FEATURE:
<223> OTHER INFORMATION: Homo sapiens

<400> SEQUENCE: 104
agcccuagga gguccgucut t                                              21

<210> SEQ ID NO 105
<211> LENGTH: 23
<212> TYPE: DNA
<213> ORGANISM: Artificial Sequence
<220> FEATURE:
<223> OTHER INFORMATION: Homo sapiens

<400> SEQUENCE: 105
acguacuaag gaaggcgcac acg                                            23

<210> SEQ ID NO 106
<211> LENGTH: 23
<212> TYPE: DNA
<213> ORGANISM: Artificial Sequence
<220> FEATURE:
<223> OTHER INFORMATION: Homo sapiens

<400> SEQUENCE: 106
ggugugcgcc uuccuuagua cgu                                            23

<210> SEQ ID NO 107
<211> LENGTH: 23
<212> TYPE: DNA
<213> ORGANISM: Artificial Sequence
<220> FEATURE:
<223> OTHER INFORMATION: Homo sapiens

<400> SEQUENCE: 107
agacggaccu ccuagggcua auc                                            23

<210> SEQ ID NO 108
<211> LENGTH: 23
<212> TYPE: DNA
<213> ORGANISM: Artificial Sequence
<220> FEATURE:
<223> OTHER INFORMATION: Homo sapiens

<400> SEQUENCE: 108
gauuagcccu aggagguccg ucu                                            23

<210> SEQ ID NO 109
<211> LENGTH: 23
<212> TYPE: DNA
<213> ORGANISM: Artificial Sequence
<220> FEATURE:
<223> OTHER INFORMATION: Homo sapiens

<400> SEQUENCE: 109
cagacggacc uccuagggcu aau                                            23
```

<210> SEQ ID NO 110
<211> LENGTH: 23
<212> TYPE: DNA
<213> ORGANISM: Artificial Sequence
<220> FEATURE:
<223> OTHER INFORMATION: Homo sapiens

<400> SEQUENCE: 110
auuagcccua ggagguccgu cug                                              23

<210> SEQ ID NO 111
<211> LENGTH: 23
<212> TYPE: DNA
<213> ORGANISM: Artificial Sequence
<220> FEATURE:
<223> OTHER INFORMATION: Homo sapiens

<400> SEQUENCE: 111
acggaccucc uagggcuaau cug                                              23

<210> SEQ ID NO 112
<211> LENGTH: 23
<212> TYPE: DNA
<213> ORGANISM: Artificial Sequence
<220> FEATURE:
<223> OTHER INFORMATION: Homo sapiens

<400> SEQUENCE: 112
cagauuagcc cuaggagguc cgu                                              23

<210> SEQ ID NO 113
<211> LENGTH: 23
<212> TYPE: DNA
<213> ORGANISM: Artificial Sequence
<220> FEATURE:
<223> OTHER INFORMATION: Homo sapiens

<400> SEQUENCE: 113
gcacguacua aggaaggcgc aca                                              23

<210> SEQ ID NO 114
<211> LENGTH: 23
<212> TYPE: DNA
<213> ORGANISM: Artificial Sequence
<220> FEATURE:
<223> OTHER INFORMATION: Homo sapiens

<400> SEQUENCE: 114
ugugcgccuu ccuuaguacg ugc                                              23

<210> SEQ ID NO 115
<211> LENGTH: 23
<212> TYPE: DNA
<213> ORGANISM: Artificial Sequence
<220> FEATURE:
<223> OTHER INFORMATION: Homo sapiens

<400> SEQUENCE: 115
aaccaaaccc gagaggaagg gca                                              23

<210> SEQ ID NO 116
<211> LENGTH: 23
<212> TYPE: DNA
<213> ORGANISM: Artificial Sequence
<220> FEATURE:
<223> OTHER INFORMATION: Homo sapiens

```
<400> SEQUENCE: 116
ugcccuuccu cucggguuug guu                                        23

<210> SEQ ID NO 117
<211> LENGTH: 23
<212> TYPE: DNA
<213> ORGANISM: Artificial Sequence
<220> FEATURE:
<223> OTHER INFORMATION: Homo sapiens

<400> SEQUENCE: 117
gacggaccuc cuagggcuaa ucu                                        23

<210> SEQ ID NO 118
<211> LENGTH: 23
<212> TYPE: DNA
<213> ORGANISM: Artificial Sequence
<220> FEATURE:
<223> OTHER INFORMATION: Homo sapiens

<400> SEQUENCE: 118
agauuagccc uaggaggucc guc                                        23

<210> SEQ ID NO 119
<211> LENGTH: 23
<212> TYPE: DNA
<213> ORGANISM: Artificial Sequence
<220> FEATURE:
<223> OTHER INFORMATION: Homo sapiens

<400> SEQUENCE: 119
aaaccaaacc cgagaggaag ggc                                        23

<210> SEQ ID NO 120
<211> LENGTH: 23
<212> TYPE: DNA
<213> ORGANISM: Artificial Sequence
<220> FEATURE:
<223> OTHER INFORMATION: Homo sapiens

<400> SEQUENCE: 120
gcccuuccuc ucggguuugg uuu                                        23

<210> SEQ ID NO 121
<211> LENGTH: 23
<212> TYPE: DNA
<213> ORGANISM: Artificial Sequence
<220> FEATURE:
<223> OTHER INFORMATION: Homo sapiens

<400> SEQUENCE: 121
cggaccuccu agggcuaauc uga                                        23

<210> SEQ ID NO 122
<211> LENGTH: 23
<212> TYPE: DNA
<213> ORGANISM: Artificial Sequence
<220> FEATURE:
<223> OTHER INFORMATION: Homo sapiens

<400> SEQUENCE: 122
ucagauuagc ccuaggaggu ccg                                        23

<210> SEQ ID NO 123
<211> LENGTH: 23
```

```
<212> TYPE: DNA
<213> ORGANISM: Artificial Sequence
<220> FEATURE:
<223> OTHER INFORMATION: Homo sapiens

<400> SEQUENCE: 123
aauuccuaga cccguaggug gcc                                              23

<210> SEQ ID NO 124
<211> LENGTH: 23
<212> TYPE: DNA
<213> ORGANISM: Artificial Sequence
<220> FEATURE:
<223> OTHER INFORMATION: Homo sapiens

<400> SEQUENCE: 124
ggccaccuac ggucuagga auu                                               23

<210> SEQ ID NO 125
<211> LENGTH: 23
<212> TYPE: DNA
<213> ORGANISM: Artificial Sequence
<220> FEATURE:
<223> OTHER INFORMATION: Homo sapiens

<400> SEQUENCE: 125
cacguacuaa ggaaggcgca cag                                              23

<210> SEQ ID NO 126
<211> LENGTH: 23
<212> TYPE: DNA
<213> ORGANISM: Artificial Sequence
<220> FEATURE:
<223> OTHER INFORMATION: Homo sapiens

<400> SEQUENCE: 126
cugugcgccu uccuuaguac gug                                              23

<210> SEQ ID NO 127
<211> LENGTH: 23
<212> TYPE: DNA
<213> ORGANISM: Artificial Sequence
<220> FEATURE:
<223> OTHER INFORMATION: Homo sapiens

<400> SEQUENCE: 127
ucgauaggac uccacgugcc acu                                              23

<210> SEQ ID NO 128
<211> LENGTH: 23
<212> TYPE: DNA
<213> ORGANISM: Artificial Sequence
<220> FEATURE:
<223> OTHER INFORMATION: Homo sapiens

<400> SEQUENCE: 128
aguggcacgu ggaguccuau cga                                              23

<210> SEQ ID NO 129
<211> LENGTH: 23
<212> TYPE: DNA
<213> ORGANISM: Artificial Sequence
<220> FEATURE:
<223> OTHER INFORMATION: Homo sapiens

<400> SEQUENCE: 129
ugaaauauuc gagagcagga ccg                                              23
```

```
<210> SEQ ID NO 130
<211> LENGTH: 23
<212> TYPE: DNA
<213> ORGANISM: Artificial Sequence
<220> FEATURE:
<223> OTHER INFORMATION: Homo sapiens

<400> SEQUENCE: 130
cgguccugcu cucgaauauu uca                                               23

<210> SEQ ID NO 131
<211> LENGTH: 23
<212> TYPE: DNA
<213> ORGANISM: Artificial Sequence
<220> FEATURE:
<223> OTHER INFORMATION: Homo sapiens

<400> SEQUENCE: 131
ggaccuccua gggcuaaucu gau                                               23

<210> SEQ ID NO 132
<211> LENGTH: 23
<212> TYPE: DNA
<213> ORGANISM: Artificial Sequence
<220> FEATURE:
<223> OTHER INFORMATION: Homo sapiens

<400> SEQUENCE: 132
aucagauuag cccuaggagg ucc                                               23

<210> SEQ ID NO 133
<211> LENGTH: 23
<212> TYPE: DNA
<213> ORGANISM: Artificial Sequence
<220> FEATURE:
<223> OTHER INFORMATION: Homo sapiens

<400> SEQUENCE: 133
ugaggucgau aggacuccac gug                                               23

<210> SEQ ID NO 134
<211> LENGTH: 23
<212> TYPE: DNA
<213> ORGANISM: Artificial Sequence
<220> FEATURE:
<223> OTHER INFORMATION: Homo sapiens

<400> SEQUENCE: 134
cacguggagu ccuaucgacc uca                                               23

<210> SEQ ID NO 135
<211> LENGTH: 23
<212> TYPE: DNA
<213> ORGANISM: Artificial Sequence
<220> FEATURE:
<223> OTHER INFORMATION: Homo sapiens

<400> SEQUENCE: 135
gcaggaccgu uucuacugaa gag                                               23

<210> SEQ ID NO 136
<211> LENGTH: 23
<212> TYPE: DNA
<213> ORGANISM: Artificial Sequence
<220> FEATURE:
<223> OTHER INFORMATION: Homo sapiens
```

```
<400> SEQUENCE: 136
cucuucagua gaaacggucc ugc                                          23

<210> SEQ ID NO 137
<211> LENGTH: 23
<212> TYPE: DNA
<213> ORGANISM: Artificial Sequence
<220> FEATURE:
<223> OTHER INFORMATION: Homo sapiens

<400> SEQUENCE: 137
gaaauauucg agagcaggac cgu                                          23

<210> SEQ ID NO 138
<211> LENGTH: 23
<212> TYPE: DNA
<213> ORGANISM: Artificial Sequence
<220> FEATURE:
<223> OTHER INFORMATION: Homo sapiens

<400> SEQUENCE: 138
acgguccugc ucucgaauau uuc                                          23

<210> SEQ ID NO 139
<211> LENGTH: 23
<212> TYPE: DNA
<213> ORGANISM: Artificial Sequence
<220> FEATURE:
<223> OTHER INFORMATION: Homo sapiens

<400> SEQUENCE: 139
ucugaggucg auaggacucc acg                                          23

<210> SEQ ID NO 140
<211> LENGTH: 23
<212> TYPE: DNA
<213> ORGANISM: Artificial Sequence
<220> FEATURE:
<223> OTHER INFORMATION: Homo sapiens

<400> SEQUENCE: 140
cguggaguaa uaucgaccuc aga                                          23

<210> SEQ ID NO 141
<211> LENGTH: 23
<212> TYPE: DNA
<213> ORGANISM: Artificial Sequence
<220> FEATURE:
<223> OTHER INFORMATION: Homo sapiens

<400> SEQUENCE: 141
ccagcaagua auccuagac ccg                                           23

<210> SEQ ID NO 142
<211> LENGTH: 23
<212> TYPE: DNA
<213> ORGANISM: Artificial Sequence
<220> FEATURE:
<223> OTHER INFORMATION: Homo sapiens

<400> SEQUENCE: 142
cgggucuagg aauuacuugc ugg                                          23

<210> SEQ ID NO 143
<211> LENGTH: 23
```

```
<212> TYPE: DNA
<213> ORGANISM: Artificial Sequence
<220> FEATURE:
<223> OTHER INFORMATION: Homo sapiens

<400> SEQUENCE: 143
agugccucug aggucgauag gac                                               23

<210> SEQ ID NO 144
<211> LENGTH: 23
<212> TYPE: DNA
<213> ORGANISM: Artificial Sequence
<220> FEATURE:
<223> OTHER INFORMATION: Homo sapiens

<400> SEQUENCE: 144
guccuaucga ccucagaggc acu                                               23

<210> SEQ ID NO 145
<211> LENGTH: 18
<212> TYPE: DNA
<213> ORGANISM: Artificial Sequence
<220> FEATURE:
<223> OTHER INFORMATION: Homo sapiens

<400> SEQUENCE: 145
ttccatttga gatggcat                                                     18

<210> SEQ ID NO 146
<211> LENGTH: 18
<212> TYPE: DNA
<213> ORGANISM: Artificial Sequence
<220> FEATURE:
<223> OTHER INFORMATION: Homo sapiens

<400> SEQUENCE: 146
tccatttgag atggcatt                                                     18

<210> SEQ ID NO 147
<211> LENGTH: 18
<212> TYPE: DNA
<213> ORGANISM: Artificial Sequence
<220> FEATURE:
<223> OTHER INFORMATION: Homo sapiens

<400> SEQUENCE: 147
ccatttgaga tggcattt                                                     18

<210> SEQ ID NO 148
<211> LENGTH: 18
<212> TYPE: DNA
<213> ORGANISM: Artificial Sequence
<220> FEATURE:
<223> OTHER INFORMATION: Homo sapiens

<400> SEQUENCE: 148
catttgagat ggcatttt                                                     18

<210> SEQ ID NO 149
<211> LENGTH: 18
<212> TYPE: DNA
<213> ORGANISM: Artificial Sequence
<220> FEATURE:
<223> OTHER INFORMATION: Homo sapiens

<400> SEQUENCE: 149
atttgagatg gcattttg                                                     18
```

<210> SEQ ID NO 150
<211> LENGTH: 18
<212> TYPE: DNA
<213> ORGANISM: Artificial Sequence
<220> FEATURE:
<223> OTHER INFORMATION: Homo sapiens

<400> SEQUENCE: 150
tttgagatgg cattttgg                                                 18

<210> SEQ ID NO 151
<211> LENGTH: 18
<212> TYPE: DNA
<213> ORGANISM: Artificial Sequence
<220> FEATURE:
<223> OTHER INFORMATION: Homo sapiens

<400> SEQUENCE: 151
ttgagatggc attttggt                                                 18

<210> SEQ ID NO 152
<211> LENGTH: 18
<212> TYPE: DNA
<213> ORGANISM: Artificial Sequence
<220> FEATURE:
<223> OTHER INFORMATION: Homo sapiens

<400> SEQUENCE: 152
tgagatggca ttttggtg                                                 18

<210> SEQ ID NO 153
<211> LENGTH: 18
<212> TYPE: DNA
<213> ORGANISM: Artificial Sequence
<220> FEATURE:
<223> OTHER INFORMATION: Homo sapiens

<400> SEQUENCE: 153
gagatggcat tttggtgt                                                 18

<210> SEQ ID NO 154
<211> LENGTH: 18
<212> TYPE: DNA
<213> ORGANISM: Artificial Sequence
<220> FEATURE:
<223> OTHER INFORMATION: Homo sapiens

<400> SEQUENCE: 154
agatggcatt ttggtgtg                                                 18

<210> SEQ ID NO 155
<211> LENGTH: 18
<212> TYPE: DNA
<213> ORGANISM: Artificial Sequence
<220> FEATURE:
<223> OTHER INFORMATION: Homo sapiens

<400> SEQUENCE: 155
gatggcattt tggtgtgg                                                 18

<210> SEQ ID NO 156
<211> LENGTH: 17
<212> TYPE: DNA
<213> ORGANISM: Artificial Sequence
<220> FEATURE:
<223> OTHER INFORMATION: Homo sapiens

```
<400> SEQUENCE: 156 atggcattttt ggtgtgg                                                        17

<210> SEQ ID NO 157
<211> LENGTH: 18
<212> TYPE: DNA
<213> ORGANISM: Artificial Sequence
<220> FEATURE:
<223> OTHER INFORMATION: Homo sapiens

<400> SEQUENCE: 157
ggtttccatg gcgtgttc                                                        18

<210> SEQ ID NO 158
<211> LENGTH: 18
<212> TYPE: DNA
<213> ORGANISM: Artificial Sequence
<220> FEATURE:
<223> OTHER INFORMATION: Homo sapiens

<400> SEQUENCE: 158
tttgtgaatg taaacatc                                                        18

<210> SEQ ID NO 159
<211> LENGTH: 18
<212> TYPE: DNA
<213> ORGANISM: Artificial Sequence
<220> FEATURE:
<223> OTHER INFORMATION: Homo sapiens

<400> SEQUENCE: 159
cctttgttaa gtagcctt                                                        18

<210> SEQ ID NO 160
<211> LENGTH: 18
<212> TYPE: DNA
<213> ORGANISM: Artificial Sequence
<220> FEATURE:
<223> OTHER INFORMATION: Homo sapiens

<400> SEQUENCE: 160
ctttgccatc tctacact                                                        18
```